US008158340B2

(12) United States Patent
O'Malley

(10) Patent No.: US 8,158,340 B2
(45) Date of Patent: Apr. 17, 2012

(54) METHODS FOR DETECTING CONFORMATIONAL CHANGES IN BIOENTITIES

(75) Inventor: Shawn M. O'Malley, Horseheads, NY (US)

(73) Assignee: Corning Incorporated, Corning, NY (US)

( * ) Notice: Subject to any disclaimer, the term of this patent is extended or adjusted under 35 U.S.C. 154(b) by 248 days.

(21) Appl. No.: 11/586,363

(22) Filed: Oct. 25, 2006

(65) Prior Publication Data

US 2007/0148670 A1 Jun. 28, 2007

Related U.S. Application Data

(60) Provisional application No. 60/755,011, filed on Dec. 28, 2005.

(51) Int. Cl.
*C12Q 1/00* (2006.01)
*C12Q 1/68* (2006.01)
*C12M 1/34* (2006.01)
*G01N 33/566* (2006.01)
*G01N 33/53* (2006.01)

(52) U.S. Cl. .......... 435/4; 435/6.1; 435/287.1; 436/501; 436/804

(58) Field of Classification Search .................. None
See application file for complete search history.

(56) References Cited

U.S. PATENT DOCUMENTS

| 5,585,277 | A | 12/1996 | Bowie et al. | 436/518 |
|---|---|---|---|---|
| 5,679,582 | A | 10/1997 | Bowie et al. | 436/518 |
| 5,863,762 | A | 1/1999 | Buratowski et al. | 435/69.1 |
| 6,300,067 | B1 | 10/2001 | Buratowski et al. | 435/6 |
| 6,331,392 | B1 | 12/2001 | Laing et al. | 435/6 |
| 6,503,721 | B2 | 1/2003 | Arenas et al. | 435/6 |
| 6,569,628 | B2 | 5/2003 | Laing et al. | 435/6 |
| 6,576,430 | B1 | 6/2003 | Hsieh et al. | 435/7.1 |
| 7,349,080 | B2 * | 3/2008 | Aklian | 356/128 |
| 2002/0031778 | A1 | 3/2002 | Laing et al. | 435/6 |
| 2002/0055123 | A1 | 5/2002 | Pakula et al. | 435/7.1 |
| 2002/0064793 | A1 | 5/2002 | Arenas et al. | 435/6 |
| 2003/0017481 | A1 | 1/2003 | Golub et al. | 435/6 |
| 2004/0009495 | A1 | 1/2004 | O'Malley et al. | 435/6 |
| 2004/0191765 | A1 | 9/2004 | Mozdy et al. | 435/5 |

FOREIGN PATENT DOCUMENTS

| WO | 97/20952 | 6/1997 |
|---|---|---|
| WO | 97/36925 | 10/1997 |
| WO | 97/37230 | 10/1997 |
| WO | 00/03727 | 1/2000 |

OTHER PUBLICATIONS

Merriam-Webster on-line dictionary, definition for "Conformation." Accesed Jan. 14, 2010.*
K. Groves et al., "Catalytic Unfolding and Proteolysis of Cytochrome c Induced by Synthetic Binding Agents", Journal of American Chemical Society, 2004, vol. 126, pp. 12833-12842.
C.J. Shelton et al., "Enzymatic and Chemical Footprinting of Anthracycline Antitumor Antibodies and Related Saccharide Side Chains", Biochemistry, 1996, vol. 35, pp. 7974-7982.
J.E. Gestwicki et al., "Using Receptor Conformational Change to Detect Low Molecular Weight Analytes by Surface Plasmon Resonance", Anal. Chem., 2001, vol. 73, pp. 5732-5737.
H. Sota et al., "Detection of Conformational Changes in an Immobilized Protein Using Surface Plasmon Resonance", Anal. Chem., 1998, vol. 70, pp. 2019-2024.
S. Chah et al., Denaturation and Renaturation of Self-Assembled Yeast Iso-1-cytochrome c and Au, Anal. Chem., 2004, vol. 76, pp. 2112-2117.
O.A. Raitman et al., "Integration of Polyaniline/Poly(acrylic acid) Films and Redox Enzymes on Electrode Supports : An in Situ Electrochemical/Surface Plasmon Resonance Study of the Bioelectrocatalyzed Oxidation of Glucose or Lactate in the Integrated Bioelectrocatalytic System", Journal of American Chemical Society, 2002, vol. 124, pp. 6487-6496.
C. Park et al., "Pulse proteolysis: A simple method for quantitative determination of protein stability and ligand binding", Nature Methods, vol. 2, No. 3, Mar. 2005, pp. 207-212.
S. Chah et al., "Gold Nanoparticles as a Colorimetric Sensor for Protein Conformational Changes", Chemistry & Biology, vol. 12, Mar. 2005, pp. 323-328.
D. Moazed et al., "Specific Protection of 16 S rRNA by Translational Initiation Factors", J. Mol. Biol., 1995, vol. 248, pp. 207-210.
D.B. Jones et al., Screening protein refolding using surface plasmon resonance, Proteomics, 2004, vol. 4, pp. 1007-1013.
V.R. Juárez-González et al., "Directed Evolution, Phage Display and Combination of Evolved Mutants: A Strategy to Recover the Neutralization Properties of the scFv Version of BCF2 a Neutralizing Monoclonal Antibody Specific to Scorpion Toxin Cn2", J. Mol. Biol., 2005, vol. 346, pp. 1287-1297.
S. Yamaguchi et al., "Measuring Adsorption of a Hydrophobic Probe with a Surface Plasmon Resonance Sensor to Monitor Conformational Changes in Immoblized Proteins", Biotechnol. Prog., 2003, vol. 19, pp. 1348-1354.
J.K. Myers et al., "Denaturant m values and heat capacity changes: relation to changes in accessible surface areas of protein unfolding", Protein Science, 1995, vol. 4, pp. 2138-2148.
T.T. Waldron et al., "Stabilization of Proteins by Ligand Binding: Application to Drug Screening and Determination of Unfolding Energetics", Biochemistry, 2003, vol. 42, pp. 5058-5064.
P.J. O'Brien et al., "Catalytic promiscuity and the evolution of new enzymatic activities", Chemistry & Biology, Apr. 1999, vol. 6, pp. R91-R105.
C.M. Overall et al., "Protease degradomics: mass spectrometry discovery of protease substrates and the CLIP-CHIP, a dedicated DNA microarray of all human proteases and inhibitors", Biol. Chem., vol. 385, Jun. 2004, pp. 493-504.
S.W. Lee et al., "Regulation of Muscle Protein Degradation: Coordinated Control of Apoptotic and Ubiquitin-Proteasome Systems by Phosphatidylinositol 3 Kinase", J. Am. Soc. Nephrol., vol. 15, 2004, pp. 1537-1545.
S. Cal et al., "Polyserase-1, a human polyprotease with the ability to generate independent serine protease domains from a single translation product", PNAS, Aug. 5, 2003, vol. 100, No. 16, pp. 9185-9190.
C.M. Overall, "Dilating the degradome: matrix metalloproteinase 2 (MMP-2) cuts to the heart of the matter", Biochem. J., 2004, vol. 383, e5-e7.

(Continued)

*Primary Examiner* — Bradley L Sisson
(74) *Attorney, Agent, or Firm* — John L. Haack

(57) ABSTRACT

Described herein are methods for detecting conformational changes in bioentities.

8 Claims, 22 Drawing Sheets

OTHER PUBLICATIONS

Carver, Theodore E., et al, "Decrypting the Biochemical Function of an Essential Gene from *Streptococcus pneumoniae* Using ThermoFluor® Technology", The Journal of Biological Chemistry, vol. 280, No. 12, issue of Mar. 25, pp. 11704-11712, (Mar. 25, 2005).

Young, Tracy A., et al., "Comparison of Proteolytic Susceptibility in Phosphoglycerate Kinases from Yeast and *E. coli*-Modulation of Conformational Ensembles Without Altering Structure or Stability", Journal of Molecular Biology, (2007), 368, 1438-1447.

Fang et al. "Optical Biosensors for monitoring Dynamic Mass Redistribution in Living Cells Meditated by Epidermal Growth Factor Receptor Activaton", Eng in Med. and Bio 27th Annual Conf., 2005, p. 1-4, IEEE.

\* cited by examiner

Trypsin digestion of Human serum albumin with and without warfarin (308 Dalton drug)

% Crosslinking as function of Glutaraldehyde Molarity

DMSO effect on XL (10% Glutaraldehyde)

% XL as function of denaturant [Gnd]

% Crosslinking Urea effect for H.S.A.

Effect of NaCl on % XL of H.S.A.

XL% for MgCl2 effect on H.S.A.

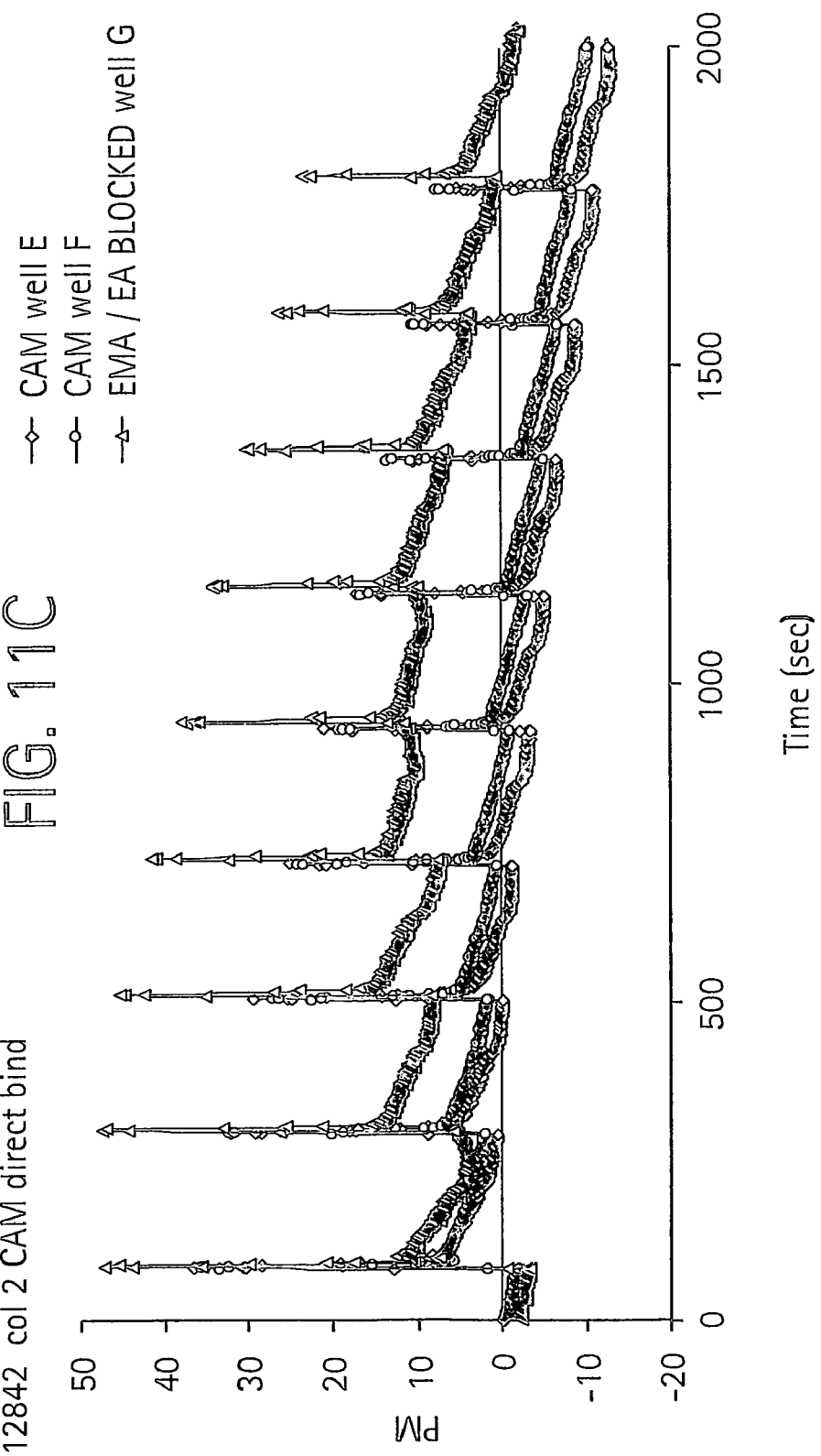

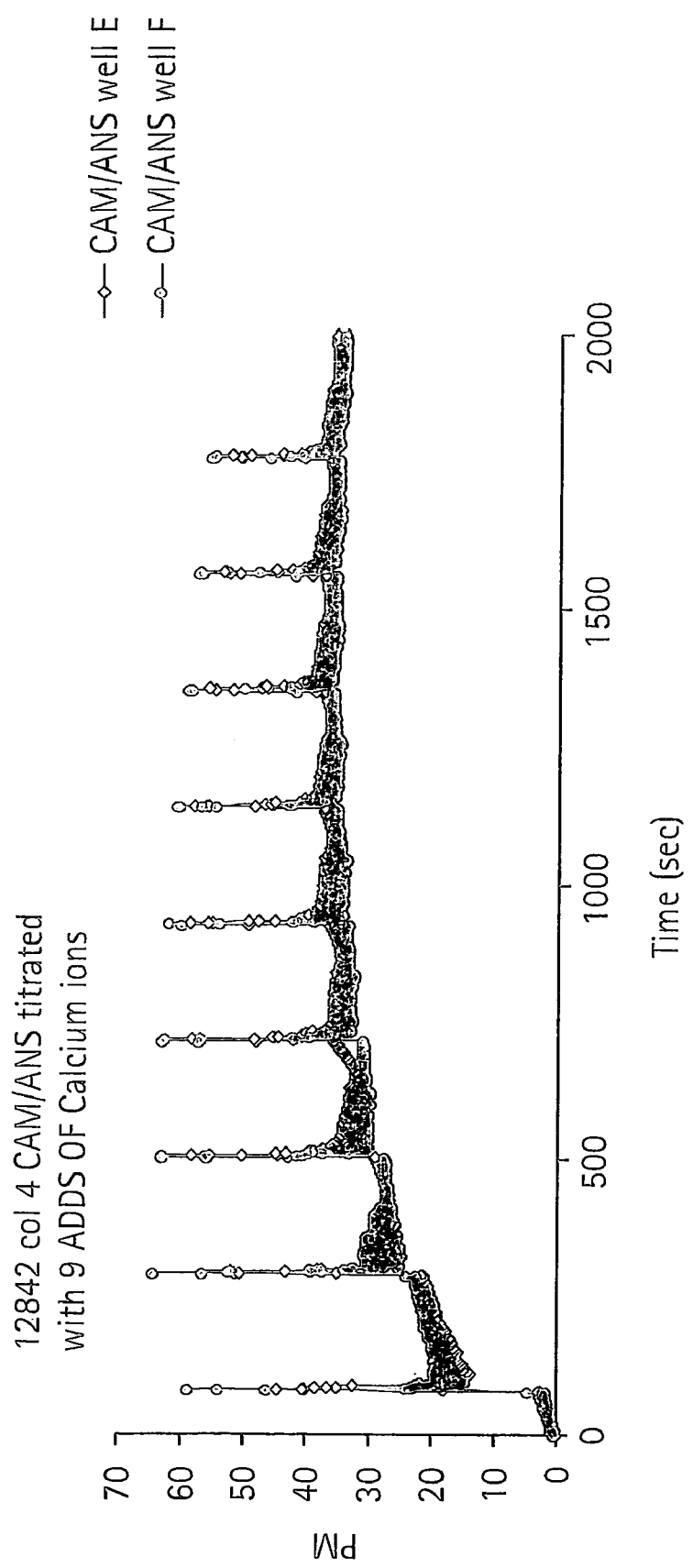

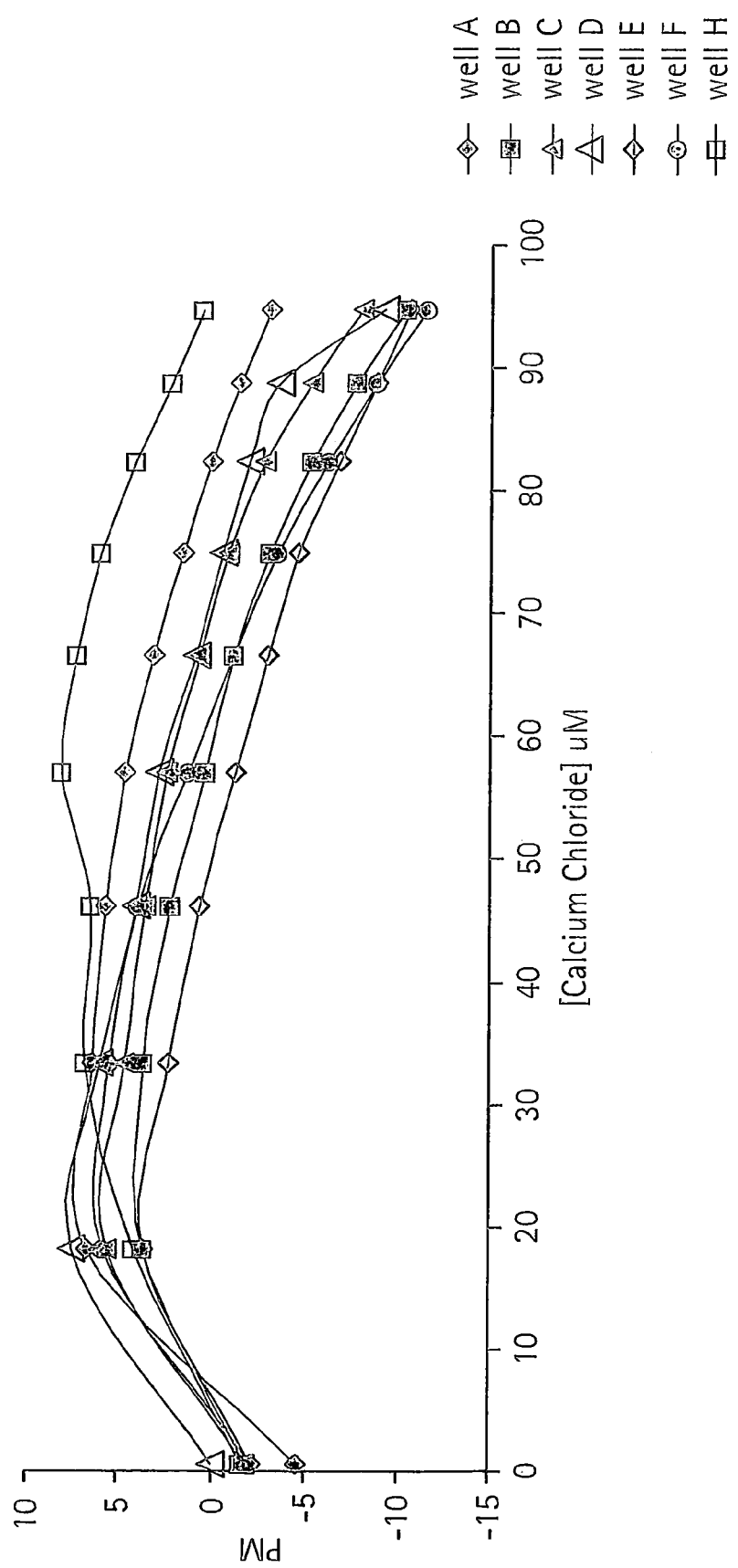

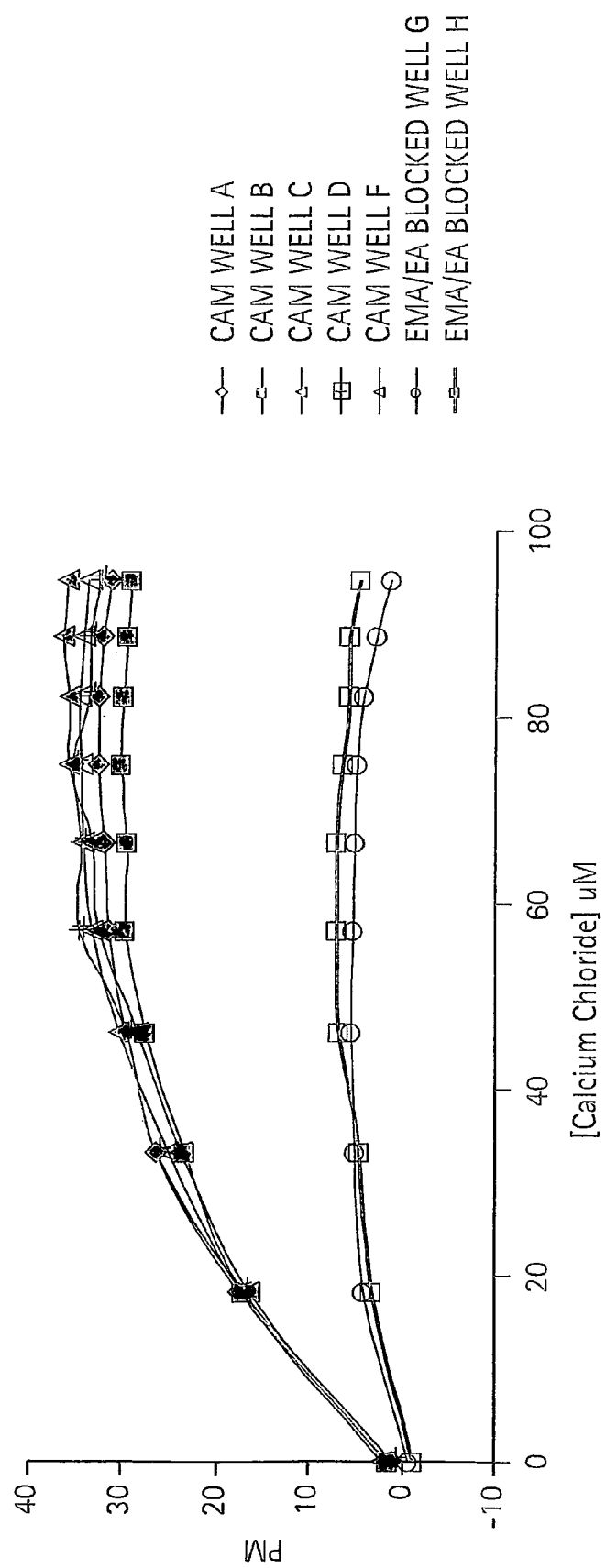

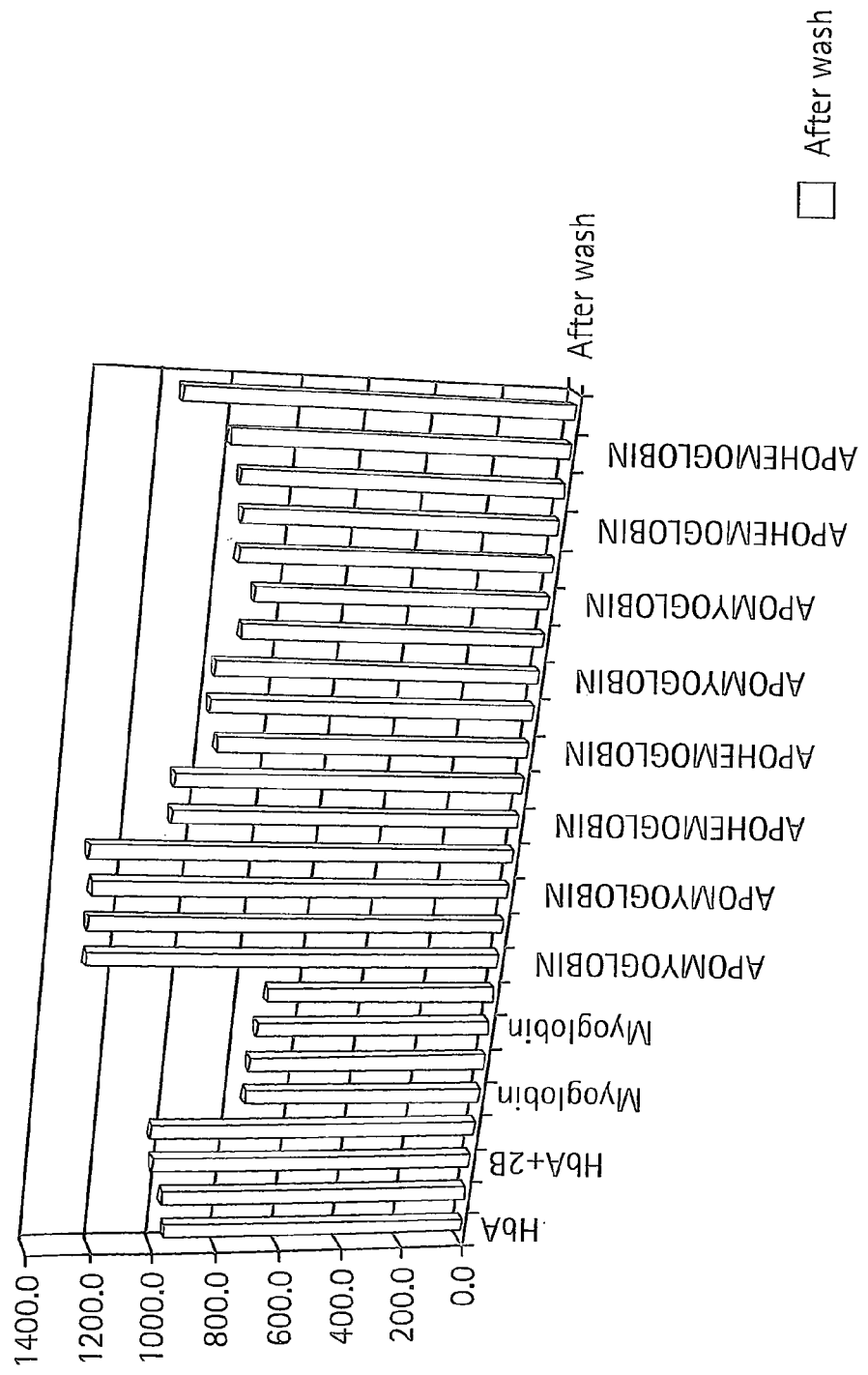

Heme insertion into Apomyoglobin

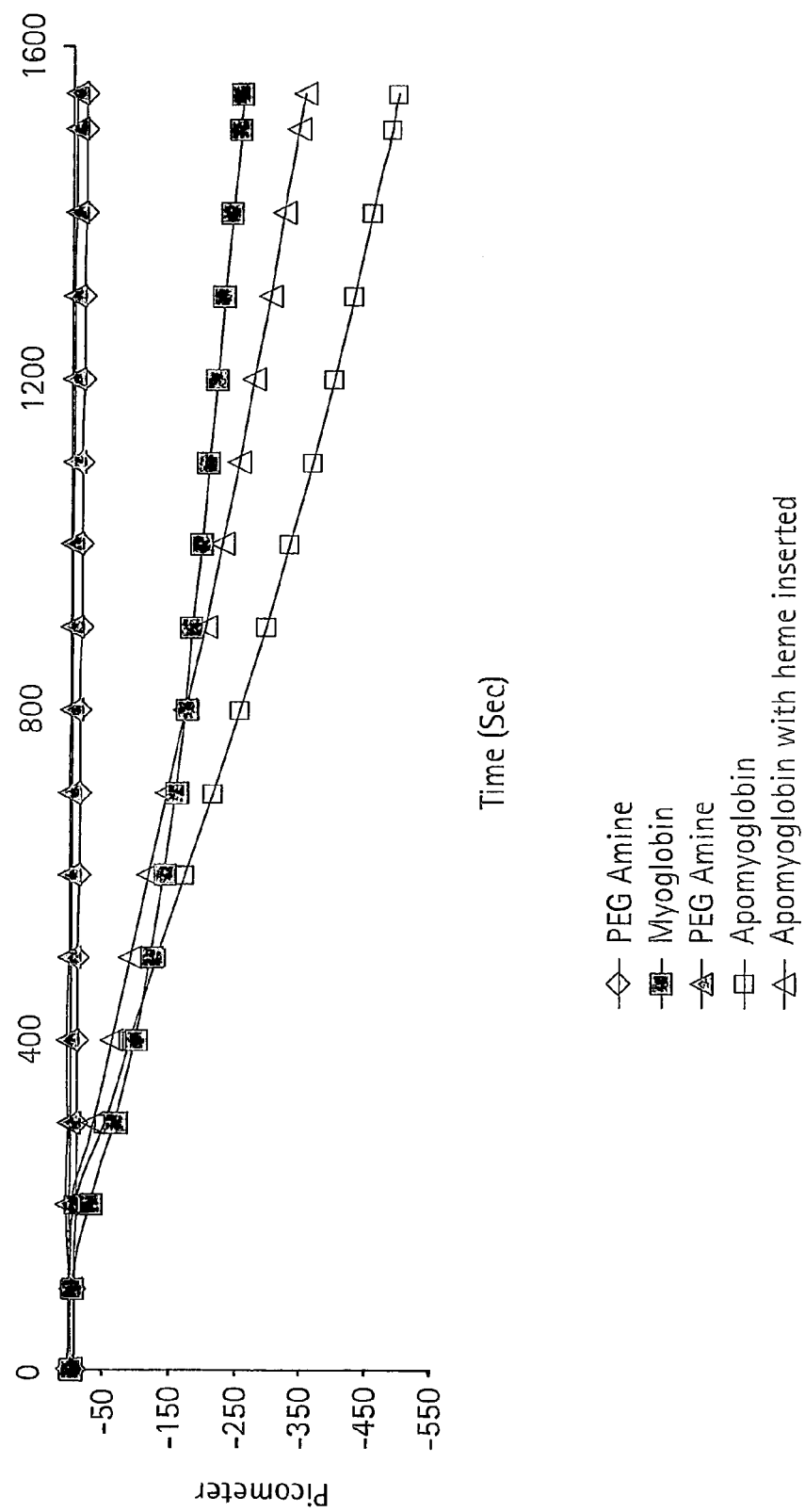

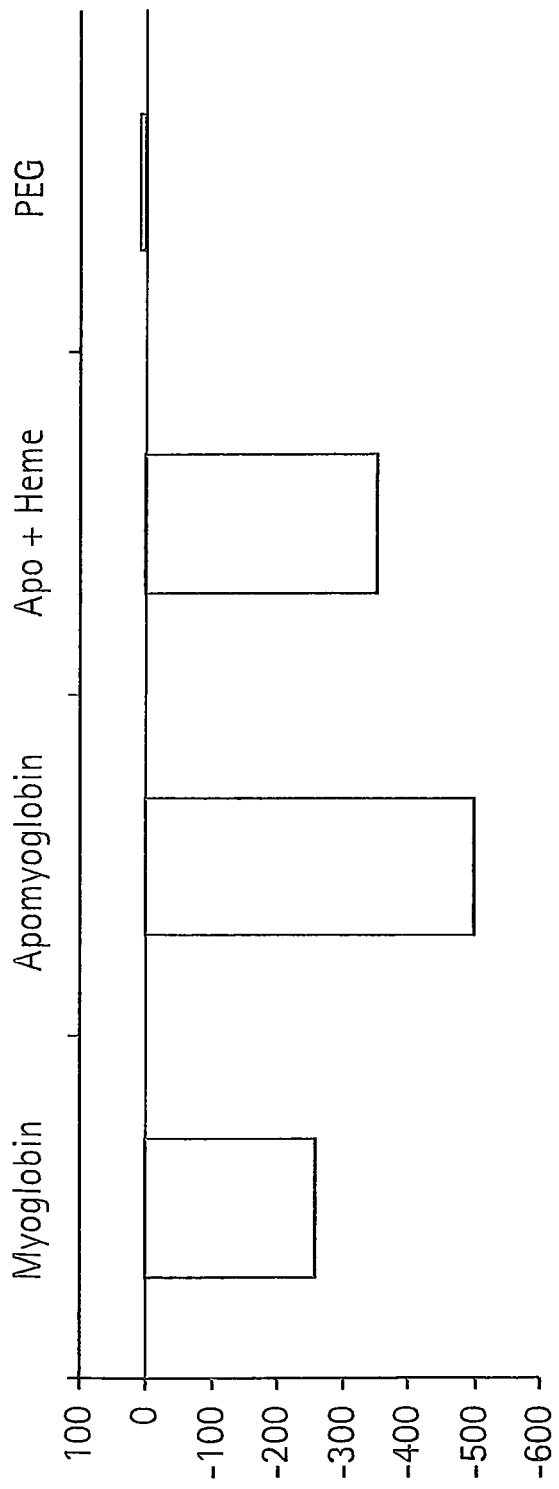

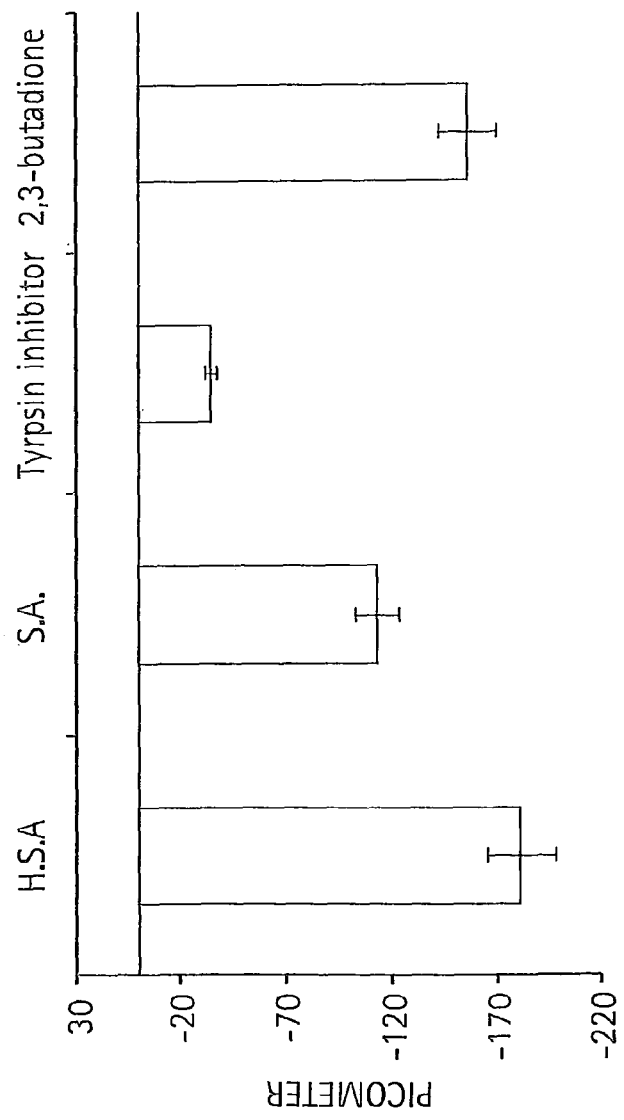

METHODS FOR DETECTING CONFORMATIONAL CHANGES IN BIOENTITIES

CLAIMING BENEFIT OF PRIOR FILED U.S. APPLICATION

This application claims the benefit of U.S. Provisional Application Ser. No. 60/755,011, filed on Dec. 28, 2005. The content of the prior document and the entire disclosure of publications, patents, and patent documents mentioned herein are incorporated by reference.

BACKGROUND

Information about the topology or conformation of a bioentity can be very useful as a diagnostic or research tool. For example, mis-folded conformational states of a bioentity can be a determinant of a disease state (e.g. prions). Conformational assays have been performed on either a single molecule or between two or more interacting molecules. Intrinsic conformational flexibility of bioentities is well documented in the literature and has been used in the prior art as a screening tool for drug discovery. Other indirect bind screening tools exist such as displacement assays coupled with mass spectroscopy as well as capillary electrophoresis are known.

Biosensors that measure changes in refractive index provide an attractive option for detecting conformational changes in bioentities, particularly changes in conformation induced by a ligand that has an affinity for the bioentity. However, in some cases the molecular weight of the ligand of interest may not be sufficient to provide a direct bind response (e.g. binders below 250 Dalton). Therefore, indirect methods that enable detection of low molecular weight ligand binders on refractive index detecting systems would be of great value. In addition, stereo-specific conformational changes between the two interacting molecules or within a single molecule may be critical in understanding the mechanism of action of the bioentity or ligand that has an affinity for the bioentity.

Described herein are methods for detecting conformational changes in bioentities. The methods involve the use of evanescent detection as a way for detecting conformational changes in a bioentity or changes that occur when the bioentity interacts with another molecule that induces a conformational change in the bioentity. The methods can be use by themselves or in combination with other with other detection platforms. The methods described herein can be a useful tool in research and provide valuable structural information of bioentities that current detection methods cannot easily provide.

SUMMARY

Described herein are methods for detecting conformational changes in bioentities. The advantages of the materials, methods, and articles described herein will be set forth in part in the description which follows, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE DRAWINGS

The accompanying drawings, which are incorporated in and constitute a part of this specification, illustrate several aspects described below. It will be appreciated that these drawings depict only typical embodiments of the materials, articles, and methods described herein and are therefore not to be considered limiting of their scope.

FIG. 13 shows the direct binding of calcium ions with CAM, where little to no binding between the calcium ions and CAM can be observed.

FIG. 14 shows the conformational change of CAM due to calcium ions in the presence of ANS.

FIG. 15 shows the immobilization of heme containing and apoheme proteins on an Epic™ biosensor.

FIG. 18 shows traces for trypsin digestion of myoglobin, apomyoglobin, apomyoglobin with heme, and PEG.

FIG. 19 is a bar graph for trypsin digestion of myoglobin, apomyoglobin, apomyoglobin with heme, and PEG.

FIG. 20 is a bar graph showing trypsin digestion of H.S.A. in the presence of trypsin inhibitor and chemical modification of H.S.A with 2,3-butadione.

DETAILED DESCRIPTION

Figure 1:
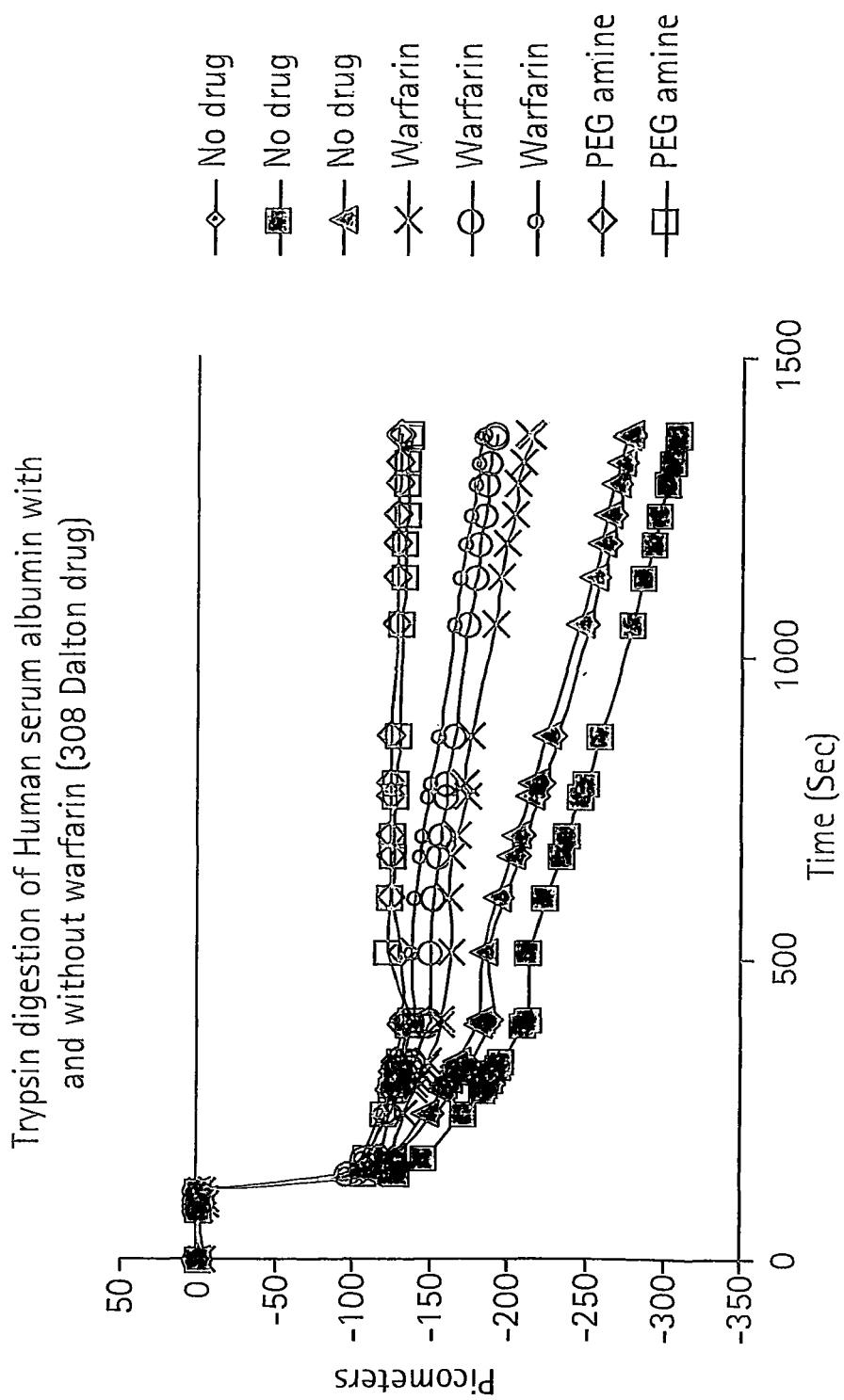
FIG. 1 shows the average of five time traces for trypsin digestion of human serum albumin on the biosensor surface.

Before the present materials, articles, and/or methods are disclosed and described, it is to be understood that the aspects described below are not limited to specific compounds, synthetic methods, or uses as such may, of course, vary. It is also to be understood that the terminology used herein is for the purpose of describing particular aspects only and is not intended to be limiting.

In this specification and in the claims that follow, reference will be made to a number of terms that shall be defined to have the following meanings:

Throughout this specification, unless the context requires otherwise, the word "comprise," or variations such as "comprises" or "comprising," will be understood to imply the inclusion of a stated integer or step or group of integers or steps but not the exclusion of any other integer or step or group of integers or steps.

It must be noted that, as used in the specification and the appended claims, the singular forms "a," "an" and "the"

include plural referents unless the context clearly dictates otherwise. Thus, for example, reference to "a pharmaceutical carrier" includes mixtures of two or more such carriers, and the like.

"Optional" or "optionally" means that the subsequently described event or circumstance can or cannot occur, and that the description includes instances where the event or circumstance occurs and instances where it does not.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed, then "less than or equal to 10" as well as "greater than or equal to 10" is also disclosed. It is also understood that throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

The term "attached" as used herein is any chemical interaction between two components or compounds. The type of chemical interaction that can be formed will vary depending upon the starting materials that are selected and reaction conditions. Examples of attachments described herein include, but are not limited to, covalent or non-covalent (e.g., electrostatic, ionic, hydrogen, or hydrophobic bonding) binding.

Disclosed are compounds, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a number of different binding molecules and bioentities are disclosed and discussed, each and every combination and permutation of the polymer and bioentity are specifically contemplated unless specifically indicated to the contrary. Thus, if a class of molecules A, B, and C are disclosed as well as a class of molecules D, E, and F and an example of a combination molecule, A-D is disclosed, then even if each is not individually recited, each is individually and collectively contemplated. Thus, in this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. This concept applies to all aspects of this disclosure including, but not limited to, steps in methods of making and using the disclosed compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

I. Introduction

Described herein are methods for detecting conformational changes in bioentities. In certain aspects, the methods described herein involve immobilizing one or more bioentities on the surface of a biosensor and detecting a change in refractive index when the conformation of the bioentity changes. In other aspects, the methods described herein can also be used to indirectly assess conformational changes in agents not immobilized on the sensor. For example, alterations in the digesting agents either through chemical or associative interaction may be indirectly assayed by functional degradation or denaturation performance on the biosensor. The conformation of the bioentity can be altered or changed using a number of techniques that will be described below. The methods described herein permit the detection of conformational changes in bioentities that are not easily possible by other methods. In various aspects, the assays are label independent assays.

II. Biosensors

The biosensors useful herein can detect a change in refractive index. The biosensor is generally composed of a medium that permits the passage of light. In one aspect, the biosensor can measure changes in evanescent refractive index. The biosensors can directly measure a change in refractive index or, in the alternative, the change in refractive index can be extrapolated from data produced by the biosensor. The biosensors described herein can be composed of one or more different layers of material, where the materials can change or alter (i.e., refract) the direction of light when it passes from one layer to next. When a bioentity such as, for example a protein or oligonucleotide is immobilized on the surface of the biosensor, the refractive index near the interface between the bioentity and the surface of the biosensor changes, which can be readily detected. The term "refractive index" is defined as the ratio of the velocity of a specific radiation in a vacuum to its velocity in a given medium. When changes occur at the immobilized bioentity, they will provide a specific change in refractive index at the surface of the biosensor. Thus, it is possible to use the biosensor with the immobilized bioentity as a tool for detecting similar or identical changes to the bioentity. Examples of changes to the immobilized bioentity that influence the refractive index will be discussed below.

In one aspect, the biosensor comprises a glass substrate with a layer of gold deposited on the surface of the substrate, a glass substrate with a layer of hafnium oxide, a grating coupled biosensor, a Fabry Perot cavity sensor, a zero-mode waveguide, a fluorescence enhanced SPR biosensor, a nanometer or micrometer cantilever biosensor, an impedance based electrode detection, or a high Q whispering mode gallery cavity resonator.

In another aspect, the biosensor comprises a glass substrate comprising an outer surface, wherein a first polymer is adjacent to the outer surface of the glass substrate. In various aspects, a first polymer comprising one or more functional groups that can bind a bioentity to the biosensor can be used. The "functional group" on the first polymer or any polymer described herein permits or facilitates the immobilization of the bioentity to the surface of the biosensor. One or more electrophilic groups present on the first polymer layer can form a covalent bond with a bioentity. Alternatively, one or more groups can be present on the first polymer so that a non-covalent bond can be formed with the bioentity.

The first polymer can be water-soluble or water-insoluble depending upon the technique used to attach the first polymer to the biosensor. The first polymer can be either linear or non-linear. For example, when the first polymer is non-linear, the first polymer is a dendritic polymer. The first polymer can be a homopolymer or a copolymer.

In a further aspect, the first polymer comprises at least one amine-reactive group. The term "amine-reactive group" is any group that is capable of reacting with an amine group to form a new covalent bond. The amine can be a primary, secondary, or tertiary amine. In a further aspect, the amine-reactive group comprises an ester group, an epoxide group, or an aldehyde group. In a further aspect, the amine-reactive group is an anhydride group.

In a further aspect, the first polymer comprises a copolymer derived from maleic anhydride and a first monomer. In this aspect, the amount of maleic anhydride in the first polymer is from 5% to 50%, 5% to 45%, 5% to 40%, 5% to 35%, 5% to 30%, 5% to 25%, 10% to 50%, 15% to 50%, 20% to 50%, 25% to 50%, or 30% to 50% by stoichiometry (i.e., molar amount) of the first monomer. In one aspect, the first monomer selected improves the stability of the maleic anhydride group in the first polymer. In another aspect, the first monomer reduces nonspecific binding of the bioentity to the substrate. In a further aspect, the amount of maleic anhydride in the first polymer is about 50% by stoichiometry of the first monomer. In another aspect, the first monomer comprises styrene, tetradecene, octadecene, methyl vinyl ether, triethylene glycol methyl vinyl ether, butylvinyl ether, divinylbenzene, ethylene, acrylamide, dimethylacrylamide, pyrolidone, a polymerizable oligo(ethylene glycol) or oligo(ethylene oxide), or a combination thereof.

In a further aspect, the first polymer comprises, poly(vinyl acetate-maleic anhydride), poly(styrene-co-maleic anhydride), poly(isobutylene-alt-maleic anhydride), poly(maleic anhydride-alt-1-octadecene), poly(maleic anhydride-alt-1-tetradecene), poly(maleic anhydride-alt-methyl vinyl ether), poly(triethyleneglycol methyvinyl ether-co-maleic anhydride), poly(ethylene-alt-maleic anhydride), or a combination thereof.

In another aspect, the first polymer can be a polymer that interacts with the immobilized bioentity. For example, polyaniline/poly(acrylic acid) (the first polymer) can behave as an electrocatalyst for the oxidation of NADH (the bioentity) (see Raitman et al., *J. Am. Chem. Soc.* (2002), 124, 6487-6496.). Thus, the first polymer can be selected to change the properties (e.g., steric, electronic, etc.) of the bioentity upon immobilization.

The amount of first polymer attached to the biosensor can vary depending upon among other things the selection the first polymer and the bioentity that is to be immobilized. In one aspect, the first polymer comprises at least one monolayer. In another aspect, the first polymer has a thickness of about 10 Å to about 2,000 Å. In a further aspect, the thickness of the first polymer has a lower endpoint of 10 Å, 20 Å, 40 Å, 60 Å, 80 Å, 100 Å, 150 Å, 200 Å, 300 Å, 400 Å, or 500 Å and an upper endpoint of 750 Å, 1,000 Å, 1,250 Å, 1,500 Å, 1,750 Å, or 2,000 Å, where any lower endpoint can be combined with any upper endpoint to form the thickness range.

The first polymer can be attached to the biosensor using techniques known in the art. For example, the biosensor can be dipped in a solution of the first polymer. In another aspect, the first polymer-can be sprayed, vapor deposited, screen-printed, or robotically pin printed or stamped on the biosensor. The amine reactivity can be chemically quenched by the addition of non-ligand binding amine containing compounds such as ethanolamine.

In certain aspects, the first polymer can be attached to the biosensor with the use of a tie layer. For example, the biosensor has a tie layer covalently bonded to the biosensor surface. It is also contemplated that a different tie layer compound can be attached to the substrate by other means in combination with a tie layer compound that is covalently bonded to the substrate. For example, one tie layer compound can be covalently bonded to the biosensor and a second tie layer compound can be electrostatically bonded to the biosensor. In a further aspect, when the tie layer is electrostatically bonded to the biosensor, the compound used to make the tie layer is positively charged and the outer surface of the biosensor is treated such that a net negative charge exists so that tie layer compound and the outer surface of the biosensor form an electrostatic bond.

In a further aspect, the outer surface of the biosensor can be derivatized so that there are groups capable of forming a covalent bond with the tie layer compound. The tie layer can be directly or indirectly covalently bonded to the biosensor. In the case when the tie layer is indirectly bonded to the substrate, a linker possessing groups that can covalently attach to both the biosensor and the tie layer compound can be used. Examples of linkers include, but are not limited to, an ether group, a polyether group, a polyamine, or a polythioether. If a linker is not used, and the tie layer compound is covalently bonded to the biosensor, this is referred to as direct covalent attachment.

In a further aspect, the tie layer is derived from a compound comprising one or more reactive functional groups that can react with the first polymer. The phrase "derived from" with respect to the tie layer is defined herein as the resulting residue or fragment of the tie layer compound when it is attached to the substrate. The functional groups permit the attachment of the first polymer to the tie layer. In a further aspect, the functional groups of the tie layer compound comprises an amino group, a thiol group, a-hydroxyl group, a carboxyl group, an acrylic acid, an organic and inorganic acid, an ester, an anhydride, an aldehyde, an epoxide, their derivatives or salts thereof, or a combination thereof. In a further aspect, the tie layer is derived from a straight or branched-chain aminosilane, aminoalkoxysilane, aminoalkylsilane, aminoarylsilane, aminoaryloxysilane, or a derivative or salt thereof. In a further aspect, the tie layer is derived from 3-aminopropyl trimethoxysilane, N-(beta-aminoethyl)-3-aminopropyl trimethoxysilane, N-(beta-aminoethyl)-3-aminopropyl triethoxysilane, N'-(beta-aminoethyl)-3-aminopropyl methoxysilane, or aminopropylsilsesquixoxane.

The tie layer can be attached to any of the biosensors described herein using techniques known in the art. For example, the biosensor can be dipped in a solution of the tie compound. In a further aspect, the tie compound can be sprayed, vapor deposited, in situ plasma synthesis of a polymer, screen printed, or robotically pin printed or stamped on the biosensor. This could be done either on a fully assembled biosensor or on a bottom insert (e.g., prior to attachment of the bottom insert to a holey plate to form a microplate).

In one aspect, the biosensor comprises the Epic™ biosensor manufactured by Corning, Inc., which is glass substrate with poly(ethylene-alt-maleic anhydride) coated on the surface of the substrate. The Epic™ system is a nanometer scale featured optical waveguide composed of glass surface coated with a nanometer scale featured polymer and high index materials such a niobium oxide or tantalum pentoxide. In other aspects, the biosensor is a Biacore carboxydextran hydrogel or the HTS biosystems sensor.

III. Bioentities

It is contemplated that one or more different bioentities can be immobilized to the substrate to produce a variety of biological sensors. The immobilization of the bioentity can involve covalent or non-covalent attachment (i.e., electrostatic, dipole-dipole, ionic, hydrogen bonding, hydrophobic, adsorption, and the like) of the bioentity to the surface of the biosensor. Immobilization can involve cross-linking agents. In one aspect, when a first polymer is present on the surface of the biosensor, the bioentity can be covalently or non-covalently attached to the first polymer.

Examples of bioentities useful herein include, but are not limited to, a natural, synthetic or modified oligonucleotide, a natural or modified nucleotide or nucleoside, a nucleic acid (DNA) or (RNA) or fragment thereof, a peptide comprising natural or modified amino acid, an antibody, a drug, a hapten, a biological ligand, a chelate, an aptamer, a lipid, a saccharide, a small molecule, a metabolite, a Ubiquitin-proteasome system (UPS), a lectin, a modified polysaccharide, a synthetic composite macromolecule, a functionalized nanostructure, a synthetic polymer, a fluorophore, a ubiquitin conjugated or poly ubiquitin conjugated protein, an affinity purified protein extract, a cell free in vitro translated protein, a chromophore, a lipid, a vesicle, a biopolymeric complex, a bioinorganic structure, chemically modified proteins or peptide (e.g., modified with phenylisothiocyanate), an organometallic complex, a ribosome, an immuno-precipitate, a tissue, a carbohydrate, an organelle, a molecular chaperone protein, a lysate or extract thereof, a virus, a cofactor, a protein-nucleic acid complex, a complex sugar, a membrane protein (e.g., GPCRs), a cell, a small molecule (e.g., a pharmaceutical drug), or a mixture thereof.

In one aspect, the bioentity can be a protein. For example, the protein can include a peptide, fragments of a protein or peptide, a membrane-bound protein, a nuclear protein, a purified protein, or an extract mixture. The protein can be of any length, and can include one or more amino acids or variants thereof. The protein(s) can be fragmented, such as by protease digestion, prior to analysis. A protein sample to be analyzed can also be subjected to fractionation or separation to reduce the complexity of the samples. Fragmentation and fractionation can also be used together in the same assay. Such fragmentation and fractionation can simplify and extend the analysis of the proteins.

In yet another aspect, the bioentity for immobilization can be made through cell free synthesis techniques. For example, cell free protein translation can provide the experimental source of protein to be immobilized for the methods described herein. It is contemplated that in vitro folding assays using molecular chaperone studies could be designed around in vitro protein synthesis. Similarly, other agents which may modulate the synthesis of the nascent folded protein can include, but are not limited to, peptides, miniature proteins, peptide nucleic acids, small organic compounds, ions, inorganic structures and drugs. The in vitro translated proteins can contain fusion tags and tags that allow easeful high affinity capture on a biosensor. Examples of such tags include, but are not limited to, hexa-histidine, GST, RNA and the like.

In a further aspect, the bioentity is a virus. Examples of viruses include, but are not limited to, Herpes simplex virus type-1, Herpes simplex virus type-2, Cytomegalovirus, Epstein-Barr virus, Varicella-zoster virus, Human herpesvirus 6, Human herpesvirus 7, Human herpesvirus 8, Variola virus, Vesicular stomatitis virus, Hepatitis A virus, Hepatitis B virus, Hepatitis C virus, Hepatitis D virus, Hepatitis E virus, Rhinovirus, Coronavirus, Influenza virus A, Influenza virus B, Measles virus, Polyomavirus, Human Papilomavirus, Respiratory syncytial virus, Adenovirus, Coxsackie virus, Dengue virus, Mumps virus, Poliovirus, Rabies virus, Rous sarcoma virus, Yellow fever virus, Ebola virus, Marburg virus, Lassa fever virus, Eastern Equine Encephalitis virus, Japanese Encephalitis virus, St. Louis Encephalitis virus, Murray Valley fever virus, West Nile virus, Rift Valley fever virus, Rotavirus A, Rotavirus B, Rotavirus C, Sindbis virus, Simian Immunodeficiency cirus, Human T-cell Leukemia virus type-1, Hantavirus, Rubella virus, Simian immunodeficiency virus, Human immunodeficiency virus type-1, Vaccinia virus, SARS virus, Human Immunodeficiency virus type-2, lentivirus, baculovirus, adeno-associated virus, or any strain or variant thereof.

In yet another aspect, the immobilized bioentity can be the subject of subsequent functional assays, wherein the bioentity either to be immobilized or already immobilized is subjected to a process or reaction that provides an expected functional modification which is then assayed on the biosensor. For example, if an immobilized protein is subjected to a cellular extract that causes phosphorylation, then the addition of phosphates to the immobilized bioentity may cause conformational changes that can be assayed on the biosensor by the methods described herein. Conversely, dephosphorylation (for example by alkaline phosphatase) can be assayed by monitoring the loss of phosphate groups on a biosensor surface. The mass shifts can be observed through phosphate recognition by an anti-phosphate antibody. As dephosphorylation proceeds, a reduction in phosphate binding on the surface is detected. Competitive assays are also possible using such a system. In this case, agents that alter expected digestion profiles on a surface can be added and compared to control reactions.

In a further aspect, the bioentity comprises a nucleic acid. The nucleic acid can be an oligonucleotide, deoxyribonucleic acid (DNA) or a fragment thereof, ribonucleic acid (RNA) or a fragment thereof, or peptide nucleic acid (PNA), a chimeric nucleic acid such as a DNA-RNA, or a fragment thereof. The nucleic acid can be a nucleic acid from any source, such as a nucleic acid obtained from cells in which it occurs in nature, recombinantly produced nucleic acid, or chemically synthesized nucleic acid. For example, the nucleic acid can be cDNA or genomic DNA or DNA synthesized to have the nucleotide sequence corresponding to that of naturally-occurring DNA. The nucleic acid can also be a mutated or altered form of nucleic acid (e.g., DNA that differs from a naturally occurring DNA by an alteration, deletion, substitution or addition of at least one nucleic acid residue) or nucleic acid that does not occur in nature. In certain aspects, methylated DNA can be used. Modified bases such as locked nucleic acids, biotinylated, methylated, photocleavable nucleic acids, phosphorothioate bases, and spiegelmers can be used. In addition, hybridized admixtures of these modified nucleic acid structures with naturally occurring nucleic acid structures may be used. These hybridized admixtures can be used to impart specific denaturation or degradation properties or specific capture properties on the biosensor. These nucleic acid structures can be chemically or enzymatically extended either in situ on the sensor or offline. Some examples of enzymatic extension can include ligation, recombination, polymerase chain extension, TdT terminal transferase extension and the like without limitation.

In a further aspect, the nucleic acid can be present in a vector such as an expression vector (e.g., a plasmid or viral-based vector). In a further aspect, the vector is a chromosomally integrated vector. The nucleic acids useful herein can be linear or circular and can be of any size. In a further aspect, the nucleic acid can be single or double stranded DNA or RNA.

In a further aspect, the nucleic acid can be a functional nucleic acid. Functional nucleic acids are nucleic acid molecules that have a specific function, such as binding a target molecule or catalyzing a specific reaction. Functional nucleic acid molecules can be divided into the following categories, which are not meant to be limiting. For example, functional nucleic acids include antisense molecules, aptamers, ribozymes, triplex forming molecules, RNAi, and external guide sequences. The functional nucleic acid molecules can act as affectors, inhibitors, modulators, and stimulators of a specific activity possessed by a target molecule, or the functional-nucleic acid molecules can possess a de novo activity independent of any other molecules.

Functional nucleic acids can be a small gene fragment that encodes dominant-acting synthetic genetic elements (SGEs), e.g., molecules that interfere with the function of genes from which they are derived (antagonists) or that are dominant constitutively active fragments (agonists) of such genes. SGEs can include, but are not limited to, polypeptides, inhibitory antisense RNA molecules, ribozymes, nucleic acid decoys, and small peptides. The small gene fragments and SGE libraries disclosed in U.S. Patent Publication No. 2003/0228601, which is incorporated by reference, can be used herein.

The functional nucleic acids of the present method can function to inhibit the function of an endogenous gene at the level of nucleic acids, e.g., by an antisense or decoy mechanism, or by encoding a polypeptide that is inhibitory through a mechanism of interference at the protein level, e.g., a dominant negative fragment of the native protein. Alternatively, certain functional nucleic acids can function to potentiate (including mimicking) the function of an endogenous gene by encoding a polypeptide which retains at least a portion of the bioactivity of the corresponding endogenous gene, and may in particular instances be constitutively active.

Functional nucleic acid molecules can interact with any macromolecule, such as DNA, RNA, polypeptides, or carbohydrate chains. Often functional nucleic acids are designed to interact with other nucleic acids based on sequence homology between the target molecule and the functional nucleic acid molecule. In other situations, the specific recognition between the functional nucleic acid molecule and the target molecule is not based on sequence homology between the functional nucleic acid molecule and the target molecule, but rather is based on the formation of tertiary structure that allows specific recognition to take place.

Antisense molecules are designed to interact with a target nucleic acid molecule through either canonical or non-canonical base pairing. The interaction of the antisense molecule and the target molecule is designed to promote the destruction of the target molecule through, for example, RNAseH mediated RNA-DNA hybrid degradation. Alternatively the antisense molecule is designed to interrupt a processing function that normally would take place on the target molecule, such as transcription or replication. Antisense molecules can be designed based on the sequence of the target molecule. Numerous methods for optimization of antisense efficiency by finding the most accessible regions of the target molecule exist. Exemplary methods would be in vitro selection experiments and DNA modification studies using DMS and DEPC. It is preferred that antisense molecules bind the target molecule with a dissociation constant (kd) less than or equal to $10^{-6 \, to \, -12}$. A representative sample of methods and techniques which aid in the design and use of antisense molecules can be found in the following non-limiting list of U.S. Pat. Nos. 5,135,917, 5,294,533, 5,627,158, 5,641,754, 5,691,317, 5,780,607, 5,786,138, 5,849,903, 5,856,103, 5,919,772, 5,955,590, 5,990,088, 5,994,320, 5,998,602, 6,005,095, 6,007,995, 6,013,522, 6,017,898, 6,018,042, 6,025,198, 6,033,910, 6,040,296, 6,046,004, 6,046,319, and 6,057,437.

Aptamers are molecules that interact with a target molecule, preferably in a specific way. Typically aptamers are small nucleic acids ranging from 15-50 bases in length that fold into defined secondary and tertiary structures, such as stem-loops or G-quartets. Aptamers can bind small molecules, such as ATP (U.S. Pat. No. 5,631,146) and theophiline (U.S. Pat. No. 5,580,737), as well as large molecules, such as reverse transcriptase (U.S. Pat. No. 5,786,462) and thrombin (U.S. Pat. No. 5,543,293). Aptamers can bind very tightly with kds from the target molecule of less than $10^{-12}$ M. It is preferred that the aptamers bind the target molecule with a kd less than $10^{-6 \, to \, -12}$. Aptamers can bind the target molecule with a very high degree of specificity. For example, aptamers have been isolated that have greater than a 10000 fold difference in binding affinities between the target molecule and another molecule that differ at only a single position on the molecule (U.S. Pat. No. 5,543,293). It is preferred that the aptamer have a kd with the target molecule at least 10, 100, 1000, 10,000, or 100,000 fold lower than the kd with a background binding molecule. It is preferred when doing the comparison for a polypeptide for example, that the background molecule be a different polypeptide. Representative examples of how to make and use aptamers to bind a variety of different target molecules can be found in the following non-limiting list of U.S. Pat. Nos. 5,476,766, 5,503,978, 5,631,146, 5,731,424, 5,780,228, 5,792,613, 5,795,721, 5,846,713, 5,858,660, 5,861,254, 5,864,026, 5,869,641, 5,958,691, 6,001,988, 6,011,020, 6,013,443, 6,020,130, 6,028,186, 6,030,776, and 6,051,698.

Ribozymes are nucleic acid molecules that are capable of catalyzing a chemical reaction, either intramolecularly or intermolecularly. Ribozymes are thus catalytic nucleic acids. It is preferred that the ribozymes catalyze intermolecular reactions. There are a number of different types of ribozymes that catalyze nuclease or nucleic acid polymerase type reactions which are based on ribozymes found in natural systems, such as hammerhead ribozymes (for example, but not limited to the following U.S. Pat. Nos. 5,334,711, 5,436,330, 5,616,466, 5,633,133, 5,646,020, 5,652,094, 5,712,384, 5,770,715, 5,856,463, 5,861,288, 5,891,683, 5,891,684, 5,985,621, 5,989,908, 5,998,193, 5,998,203, WO 9858058 by Ludwig and Sproat, WO 9858057 by Ludwig and Sproat, and WO 9718312 by Ludwig and Sproat) hairpin ribozymes (for example, but not limited to the following U.S. Pat. Nos. 5,631,115, 5,646,031, 5,683,902, 5,712,384, 5,856,188, 5,866,701, 5,869,339, and 6,022,962), and tetrahymena ribozymes (for example, but not limited to the following U.S. Pat. Nos. 5,595,873 and 5,652,107). There are also a number of ribozymes that are not found in natural systems, but which have been engineered to catalyze specific reactions de novo (for example, but not limited to the following U.S. Pat. Nos. 5,580,967, 5,688,670, 5,807,718, and 5,910,408). Preferred ribozymes cleave RNA or DNA substrates, and more preferably cleave RNA substrates. Ribozymes typically cleave nucleic acid substrates through recognition and binding of the target substrate with subsequent cleavage. This recognition is often based mostly on canonical or non-canonical base pair interactions. This property makes ribozymes particularly good candidates for target specific cleavage of nucleic acids because recognition of the target substrate is based on the target substrates sequence. Representative examples of how to make and use ribozymes to catalyze a variety of different reactions can be found in the following non-limiting list of U.S. Pat. Nos. 5,646,042, 5,693,535, 5,731,295, 5,811,300, 5,837,855, 5,869,253, 5,877,021, 5,877,022, 5,972,699, 5,972,704, 5,989,906, and 6,017,756.

Triplex forming functional nucleic acid molecules are molecules that can interact with either double-stranded or single-stranded nucleic acid. When triplex molecules interact with a target region, a structure called a triplex is formed, in which there are three strands of DNA forming a complex dependant on both Watson-Crick and Hoogsteen base-pairing. Triplex molecules are preferred because they can bind target regions with high affinity and specificity. It is preferred that the triplex forming molecules bind the target molecule with a kd less than 10-6, 10-8, 10-10, or 10-12. In other aspects, psoralen agents can be employed. Representative examples of how to make and use triplex forming molecules to bind a variety of different target molecules can be found in the following non-limiting list of U.S. Pat. Nos. 5,176,996, 5,645,985, 5,650,316, 5,683,874, 5,693,773, 5,834,185, 5,869,246, 5,874,566, and 5,962,426. Higher order nucleic acid based structures such as G tetrads, telomere like structures, toroidal DNAs, hairpins, D loops, bubble junctions, Holliday Junctions, pseudo knots, knots, borromean rings, pentamers, hexamers and the like are all capable of being evaluated on biosensors.

External guide sequences (EGSs) are molecules that bind a target nucleic acid molecule forming a complex, and this complex is recognized by RNase P, which cleaves the target molecule. EGSs can be designed to specifically target an RNA molecule of choice. RNAse P aids in processing transfer RNA (tRNA) within a cell. Bacterial RNAse P can be recruited to cleave virtually any RNA sequence by using an EGS that causes the target RNA:EGS complex to mimic the natural tRNA substrate. (WO 92/03566 by Yale, and Forster and Altman, Science 238:407-409 (1990)).

Similarly, eukaryotic EGS/RNAse P-directed cleavage of RNA can be utilized to cleave desired targets within eukarotic cells. (Yuan et al., Proc. Natl. Acad. Sci. USA 89:8006-8010 (1992); WO 93/22434 by Yale; WO 95/24489 by Yale; Yuan and Altman, EMBO J 14:159-168 (1995), and Carrara et al., Proc. Natl. Acad. Sci. (USA) 92:2627-2631 (1995)). Representative examples of how to make and use EGS molecules to facilitate cleavage of a variety of different target molecules can be found in the following non-limiting list of U.S. Pat. Nos. 5,168,053, 5,624,824, 5,683,873, 5,728,521, 5,869,248, and 5,877,162.

It is also understood that the disclosed nucleic acids can be RNA (e.g., for RNA interference (RNAi)). It is thought that RNAi involves a two-step mechanism for RNA interference: an initiation step and an effector step. For example, in the first step, input double-stranded (ds) RNA (siRNA) is processed into small fragments, such as 21-23-nucleotide "guide sequences." RNA amplification appears to be able to occur in whole animals. Typically then, the guide RNAs can be incorporated into a protein RNA complex which is cable of degrading RNA, the nuclease complex, which has been called the RNA-induced silencing complex (RISC). This RISC complex acts in the second effector step to destroy mRNAs that are recognized by the guide RNAs through base-pairing interactions. RNAi involves the introduction by any means of double stranded RNA into the cell that triggers events that cause the degradation of a target RNA. RNAi is a form of post-transcriptional gene silencing.

Disclosed are RNA hairpins that can act in RNAi. In one aspect, the RNAi agent can be small ribonucleic acid molecules (also referred to herein as interfering ribonucleic acids), i.e., oligoribonucleotides, that are present in duplex structures, e.g., two distinct oligoribonucleotides hybridized to each other or a single ribooligonucleotide that assumes a small hairpin formation to produce a duplex structure. By oligoribonucleotide is meant a ribonucleic acid that does not exceed about 100 nt in length, and typically does not exceed about 75 nt length, where the length in certain embodiments is less than about 70 nt. When the RNAi agent is a duplex structure of two distinct ribonucleic acids hybridized to each other, e.g., an siRNA, such as d-siRNA, the length of the duplex structure typically ranges from about 15 to 30 bp, usually from about 15 to 29 bp, where lengths between about 20 and 29 bps, e.g., 21 bp, 22 bp, can be used. Where the RNAi agent is a duplex structure of a single ribonucleic acid that is present in a hairpin formation, i.e., a shRNA, the length of the hybridized portion of the hairpin is typically the same as that provided above for the siRNA type of agent or longer by 4-8 nucleotides. The weight of the RNAi agents of this embodiment typically ranges from about 5,000 daltons to about 35,000 daltons, and in many embodiments is at least about 10,000 daltons and less than about 27,500 daltons, often less than about 25,000 daltons.

In certain aspects, instead of the RNAi agent being an interfering ribonucleic acid, e.g., an siRNA or shRNA as described above, the RNAi agent can encode an interfering ribonucleic acid, e.g., an shRNA, as described above. In other words, the RNAi agent can be a transcriptional template of the interfering ribonucleic acid. In these aspects, the transcriptional template can be a DNA that encodes the interfering ribonucleic acid.

RNAi has been shown to work in a number of cells, including mammalian cells. For work in mammalian cells it is preferred that the RNA molecules which will be used as targeting sequences within the RISC complex are shorter. For example, less than or equal to 50 or 40 or 30 or 29, 28, 27, 26, 25, 24, 23, 22, 21, 20, 19, 18, 17, 16, 15, 14, 13, 12, 11, or 10 nucleotides in length. These RNA molecules can also have overhangs on the 3' or 5' ends relative to the target RNA that is to be cleaved. These overhangs can be at least or less than or equal to 1, 2, 3, 4, 5, 6, 7, 8, 9, 10, 15, or 20 nucleotides long. RNAi works in mammalian stem cells, such as mouse ES cells.

For description of making and using RNAi molecules see See, e.g., Hammond et al., Nature Rev Gen 2: 110-119 (2001); Sharp, Genes Dev 15: 485-490 (2001), Waterhouse et al., Proc. Natl. Acad. Sci. USA 95(23): 13959-13964 (1998) all of which are incorporated herein by reference in their entireties and at least form material related to delivery and making of RNAi molecules. The RNAi agents disclosed in U.S. Published Application No. 2003/0228601 and International Publication No. WO2004/0798950, which are incorporated by reference with respect to the different RNAi agents, can also be used herein.

IV. Immobilization of Bioentity to Support

As discussed above, one or more bioentities can be immobilized to the biosensor. In various aspects, the bioentity can be directly immobilized to the surface of the biosensor, where the bioentity is in immediate contact with the surface of the biosensor. Alternatively, when a first polymer as described above is present on the surface of the biosensor, the bioentity is indirectly immobilized to the biosensor (i.e., the bioentity is not in direct contact with the biosensor). In other aspects, the bioentity can be directly and indirectly attached to the biosensor. The bioentity can be covalently attached to the biosensor or by a non-covalent interaction (e.g., electrostatic, ionic, hydrogen bonding, hydrophobic, adsorption, dipole-dipole, van der Waal, affinity captured and the like).

In the case of affinity capture, the affinity capture directed to the bioentity can be through aptamer or antibody capture. Alternatively, the affinity capture agent can be derived from a dynamic combinatorial library (DCL) or adaptive chemical networks. Dynamic combinatorial covalent ligand in the form of bi-dentate, tri-dentate or multi-dentate organo-metal ion coordinated self assemblies are also possible. The reversible assemblies can also be produced through metal ion coordination, imine bond formation, intramolecular rearrangement, disulfide bond formation or photo-crosslink formation. In addition, it is contemplated that these in situ self-assembly directed ligands on the biosensor surface may constitute drugs or putative drug targets in a drug screen.

In a further aspect, when the bioentity is a nucleic acid or protein, the nucleic acid or protein can be printed on the biosensor using techniques known in the art including, but not limited to, chemical conjugation, ionic or hydrophobic attachment, photocoupling, lithography, vapor deposition or affinity based techniques. The amount of bioentity that can be attached to the polymer layer can vary depending upon among other things, for example, the bioentity and the conformational change that is to be detected. In a further aspect, one or more different bioentities can be placed at different locations on the biosensor. In the case when different bioentities are used, the bioentities can be printed at the same time or different time. It is contemplated that the bioentity can be immobilized randomly or through oriented tags (e.g., GST, hexa-histidine, biotin, or a mixture thereof) on the biosensor. Affinity captured by an antibody or an aptamer is also contemplated.

In a further aspect, the spotting solution (i.e., ink) containing the bioentity also contains optional components such as, for example, an alkylene diol, a betaine, a detergent, a salt, or an aprotic solvent. The selection of components present in the ink formulation will vary and can be used to control spot size.

The term "alkylene diol" as used herein is any compound that possesses two hydroxyl groups and at least one $CH_2$ group. The alkylene diol can be branched or straight chain. In one aspect, the alkylene diol comprises the formula $HO(CH_2)_nOH$, wherein n is an integer of from 1, 2, 3, 4, 5, 6, 7, 8, 9, 10, 11, 12, 13, 14, 15, 16, 17, 18, 19, 20, 21, 22, 23, 24, or 25. In a further aspect, the alkylene diol comprises a straight chain compound such as, for example, methylene glycol, ethylene glycol, propylene glycol, butylene glycol, or a mixture thereof. In a further aspect, the alkylene diol comprises a branched compound such as, for example, isopropyl diol, isobutyl- and sec-butyl diol, neopentyl diol, and the like. In a further aspect, the alkylene diol is from 30 to 70% by volume of the composition. In another aspect, the alkylene diol is 30%, 35%, 40%, 45%, 50%, 55%, 60%, 65%, or 70% by volume of the composition, wherein any value can form a lower and upper endpoint. In one aspect, the alkylene diol is from 40 to 60% by volume of the composition.

Detergents useful herein include, but are not limited to, a surfactant. A "surfactant" as used herein is a molecule composed of hydrophilic and hydrophobic groups (i.e., an amphiphile). Suitable surfactants can be generally classified as ionic (anionic/cationic/dipolar) and nonionic. In a further aspect, polymeric surfactants, natural surfactants, silicon surfactants, fluorinated surfactants, oligomeric surfactants, dimeric surfactants, and the like, are suitable for the compositions and methods disclosed herein. In a further aspect, the surfactants disclosed in U.S. Pat. No. 6,849,426, which is incorporated by reference in its entirety, can be used herein.

In a further aspect, the detergent comprises an anionic surfactant. Any anionic surfactants known in the art can be used herein. In a further aspect, the anionic surfactant comprises an alkyl aryl sulfonate, an alkyl sulfate, or sulfated oxyethylated alkyl phenol. In a further aspect, the anionic surfactant can be an alkylbenzene sulfonate (detergent), a fatty acid based surfactant, a lauryl sulfate (e.g., a foaming agent), a di-alkyl sulfosuccinate (e.g., a wetting agent), a lignosulfonate (e.g., a dispersant), and the like, including mixtures thereof. In other examples, linear alkylbenzene sulphonic acid, sodium lauryl ether sulphate, alpha olefin sulphonates, phosphate esters, sodium sulphosuccinates, hydrotropes, and the like, including mixtures thereof, can be used. In a further aspect, the anionic surfactant comprises sodium dodecylbenzene sulfonate, sodium decylbenzene sulfonate, ammonium methyl dodecylbenzene sulfonate, ammonium dodecylbenzene sulfonate, sodium octadecylbenzene sulfonate, sodium nonylbenzene sulfonate, sodium dodecylnaphthalene sulfonate, sodium hetadecylbenzene sulfonate, potassium eicososyl naphthalene sulfonate, ethylamine undecylnaphthalene sulfonate, sodium docosylnaphthalene sulfonate, sodium octadecyl sulfate, sodium hexadecyl sulfate, sodium dodecyl sulfate, sodium nonyl sulfate, ammonium decyl sulfate, potassium tetradecyl sulfate, diethanolamino octyl sulfate, triethanolarnine octadecyl sulfate, amrnmonium nonyl sulfate, ammonium nonylphenoxyl tetraethylenoxy sulfate, sodium dodecylphenoxy triethyleneoxy sulfate, ethanolamine decylphenoxy tetraethyleneoxy sulfate, or potassium octylphenoxy triethyleneoxy sulfate.

In a further aspect, the detergent comprises a nonionic surfactant. Any nonionic surfactant can be used. Suitable nonionic surfactants do not ionize in aqueous solution, because their hydrophilic group is of a non-dissociable type, such as alcohol, phenol, ether, ester, or amide. They can be classified as ethers (e.g., polyhydric alcohols such as glycerin, sorbitole, sucrose, etc.), fatty acid esters (e.g., glycerin fatty acid ester, sorbitan fatty acid ester, sucrose fatty acid ester, etc.), esters (e.g., compounds made by applying, for example, ethylene oxide to a material having hydroxyl radicals such as high alcohol, alkyl-phenol, and the like), ether/esters (e.g., compounds made by applying, for example, the ethylene oxide to the fatty acid or polyhydric alcohol fatty acid ester, having both ester bond and ether bond in the molecule), and other types (e.g., the fatty acid alkanol-amide type or the alkylpolyglyceride type). Other suitable examples of nonionic surfactants can include, but are not limited to, alcohol ethoxylates and alkyl phenol ethyoxylates, fatty amine oxides, alkanolamides, ethylene oxide/propylene oxide block copolymers, alkyl amine ethoxylates, tigercol lubricants, etc. In a further aspect, the nonionic surfactant comprises the condensation product between ethylene oxide or propylene oxide with the propylene glycol, ethylene diamine, diethylene glycol, dodecyl phenol, nonyl phenol, tetradecyl alcohol, N-octadecyl diethanolamide, N-dodecyl monoethanolamide, polyoxyethylene sorbitan monooleate, or polyoxyethylene sorbitan monolaurate.

In a further aspect, the detergent comprises a cationic surfactant. Any cationic surfactant known in the art can be used herein. Suitable cationic surfactants included, but are not limited to, quaternary ammonium compounds, imidazolines, etc. Such cationic surfactants can be obtained commercially or can be prepared by methods known in the art. In a further aspect, the cationic surfactant comprises ethyl-dimethyl-stearyl ammonium chloride, benzyl-dimethyl-stearyl ammonium chloride, benzyldimethyl-stearyl ammonium chloride, trimethyl stearyl ammonium chloride, trimethylcetyl ammonium bromide, dimethylethyl dilaurylammonium chloride, dimethyl-propyl-myristyl ammonium chloride, or the corresponding methosulfate or acetate.

Other examples of suitable surfactant include natural surfactants, which can have their source from plant or animal organs. In another example, a bolaform surfactant can be used. A bolaform surfactant is a surfactant that has two hydrophilic head groups at opposite ends of a hydrophobic tail. In a further aspect, the detergent can be Tween-20 or Triton x-100.

In a further aspect, the detergent comprises an organic acid or the salt thereof. Examples of organic acids useful herein include saturated or unsaturated fatty acids. In one aspect, the organic acid comprises the formula $CH_3(CH_2)_mCO_2H$, wherein m is 1, 2, 3, 4, 5, 6, 7, 8, 9, 10, 11, 12, 13, 14, 15, 16, 17, 18, 19, 20, 21, 22, 23, 24, or 25, or the salt thereof. In a further aspect, the detergent comprises hexanoic acid, heptenoic acid, octanoic acid, nonanoic acid, decanoic acid, or the salt thereof. In one aspect, when the detergent comprises an organic acid such as, for example, octanoic acid, the amount of organic acid can be 0.005%, 0.01%, 0.02%, 0.03%, 0.04%, 0.05%, 0.06%, 0.07%, 0.08%, 0.09%, 0.10%, 0.15%, 0.20%, or 0.25% by volume of the composition, where nay value can form a lower and upper endpoint of the concentration range. In a further aspect, the amount of organic acid is from 0.05% to 0.10% by volume of the composition.

It is contemplated that mixtures of surfactants can also be used herein.

It is contemplated that the spotting solution or ink containing the bioentity can include a salt. In a further aspect, the salt can be an organic salt, an inorganic salt, or a mixture thereof. In a further aspect, the organic salt comprises a citrate. In a further aspect, the inorganic salt comprises NaCl, KCl, $MgCl_2$, LiCl, or a mixture thereof. In another aspect, the salt comprises a mixture of NaCl and sodium citrate.

The pH of the ink can also vary depending upon among other things the selection of starting materials and the bioentity to be spotted, which can be readily determined by one of ordinary skill in the art. In certain aspects, immobilization of the bioentity can be performed at a pH below the isoelectric point of the bioentity to be immobilized. In a further aspect, the spotting composition comprises an alkaline pH or acidic pH. In another aspect, the pH is greater than 7.0. In a further aspect, the pH is 2.0, 3.0, 3.5, 4.0, 4.5, 5.0, 5.5, 6.0, 6.5, 7.0, 8.0, 8.5, 9.0, 9.5, 10.0, 10.5, 11.0, 11.5, 12.0, 12.5, or 13, where any pH value can form a lower and upper end-point for a pH range. The pH of the ink can be adjusted by adding bases such as, for example, hydroxides, carbonates, phosphates, and the like.

The ink can also contain solvents that can reduce the rate of evaporation of water once the bioentity has been spotted on the support. Examples of solvents useful herein include, but are not limited to, dimethylsulfoxide, polyethylene glycol, ethylene glycol, glycerol, or dextran.

In a further aspect, the bioentity can be deposited on (i.e., immobilized to) the support by immersing the tip of a pin into the composition comprising the bioentity; removing the tip from the composition, wherein the tip comprises the composition; and transferring the composition to the support. This aspect can be accomplished, for example, by using a typographic pin array. The depositing step can be carried out using an automated, robotic printer. Such robotic systems are available commercially from, for example, Intelligent Automation Systems (IAS), Cambridge, Mass. Alternatively, non-contact printing such as piezoelectric deposition arrayers can be used. All these arraying methods can be used to achieve high-density microarrays of the same bioentity or a plurality of different bioentities.

The pin can be solid or hollow. The tips of solid pins are generally flat, and the diameter of the pins determines the volume of fluid that is transferred to the substrate. Solid pins having concave bottoms can also be used. In one aspect, to permit the printing of multiple arrays with a single sample loading, hollow pins that hold larger sample volumes than solid pins and therefore allow more than one array to be printed from a single loading can be used. Hollow pins include printing capillaries, tweezers and split pins. An example of a preferred split pen is a micro-spotting pin that TeleChem International (Sunnyvale, Calif.) has developed. In one aspect, pins made by Point Tech can be used herein. The spotting solutions described herein can be used in a number of commercial spotters including, but not limited to, Genetix and Biorobotics spotters.

In another aspect, during or after the immobilization of the bioentity to the biosensor, the immobilization can be performed under humid conditions. This can help control spot size, reduce evaporation of water present in the ink, and reduce printing runs.

In various aspects, when a first polymer is present on the biosensor, a blocking agent is attached to-the first polymer. Depending upon the bioentity selected, inadequate blocking can lead to high levels of non-specific binding to the surface of the biosensor, making analysis of results difficult if not impossible. Thus, in one aspect, one or more reactive sites present on the first polymer that are not attached to the bioentity can be reacted with a blocking agent to render the active site inactive. Here, the analyte will interact with the bioentity and not the first polymer, which leads to increased specific binding and better detection of the analyte.

In a further aspect, the blocking agent comprises at least one nucleophilic group, the first polymer comprises at least one electrophilic group, and the blocking agent is attached to the first polymer by a reaction between the electrophilic group and the nucleophilic group. In a further aspect, the blocking agent is covalently attached to the first polymer. For example, when the blocking agent comprises an amine group, it can react with an electrophilic group present on the first polymer (e.g., an epoxy, anhydride, ester group) to produce a covalent bond. In another aspect, when the blocking agent possesses a group that can be converted to a charged group (i.e., a salt), then the blocking agent can form an electrostatic bond with the first polymer.

In a further aspect, the blocking agent comprises 2-(2-aminoethoxy)ethanol, N,N-dimethyl ethylenediamine, ethanolamine, ethylenediamine, 4,7,10-trioxa-1,13-tridecanediamine, PEG amine, Tris hydrochloride, diethylaminoethyl-cellulose, diethylaminoethyl-cellulose amine, diethylaminoethyl-cellulose dextran, bovine serum albumin, chicken egg albumin, dry milk, pluronic or any combination thereof. In a further aspect, when the blocking agent is PEG amine, the PEG amine has a molecular weight of from 400 to 100,000 Da. In a further aspect, the blocking agent comprises 2-(2-aminoethoxy)ethanol or N,N-dimethyl ethylenediamine in a solution of pH from 7 to 10, 7 to 9, 7 to 8, 8 to 10, or 9 to 10. For example, the blocking agent can be in a solution of base such as, for example, sodium hydroxide or sodium borate.

Concentrations of the immobilized bioentity can be titrated for comprehensive kinetic analysis on the biosensor. Furthermore, solvent and modified substrates can be used to monitor reaction mechanisms. For example, isotopic solvents like deuterium oxide based buffers can be used to determine mechanistic information on the biosensor. Additionally, isotopically substituted substrates can be used in screens and mechanistic studies.

V. Induction of Conformational Changes

In general, bioentities in their natural state possess certain structures or conformations. In the presence of certain chemical or naturally-occurring agents, the conformation of the bioentity can change. The term "conformational change" is the change in structure of a bioentity from a pre-existing structure or conformation. The detection of conformational changes in bioentities can provide useful information as applied to research tools or diagnostics. For example, protein stability can be assessed through conformational state assays. Described below are several methods for the induction and detection of conformational changes in a bioentity.

a. Degradation

In one aspect, described herein is a method for detecting a conformational change in a bioentity, comprising:
a. immobilizing the bioentity on a first surface and second surface of a biosensor that can detect a change in refractive index, wherein a binding molecule is bound to the bioentity immobilized to the first surface of the biosensor, wherein the binding molecule is bound to the bioentity prior to or after immobilization;
b. exposing the immobilized components in step (a) to one or more degrading agents such that the immobilized bioentity on the first and second surface of the biosensor react with the degrading agent;
c. measuring the change in the refractive index of the immobilized bioentity on the first and second surface of the biosensor; and
d. comparing the refractive index of the immobilized bioentity on the first and second surface of the biosensor, wherein a difference in refractive index between the immobilized bioentity on the first surface and the immobilized bioentity on the second surface indicates a conformational change in the bioentity when the binding molecule is bound to the immobilized entity.

In the method described above, the ability of a binding molecule to influence the rate of degradation of the bioentity is examined. In one aspect, the binding molecule is any compound that can induce a conformational change in the bioentity. This method can be useful in screening various molecules that can change the conformation of the bioentity, where the rate of degradation can provide empirical information about the conformation change. In step (a), a binding molecule is bound to a bioentity immobilized on the surface (i.e., first surface) of the biosensor. In a control experiment, an immobilized bioentity is bound to the surface (i.e., second surface) of the biosensor with no binding molecule. It is contemplated that in all of the methods described herein, the first and second surface can be on the same biosensor or different biosensors. For example, when the biosensor is a microplate, the first and second surface can be within one well (i.e., intra-well) or two separate plates (i.e., inter-well).

In one aspect, the binding molecule can be a small molecule such as, for example, a pharmaceutical drug. In general, biosensors that can detect a change in refractive index cannot easily measure small changes in molecular weight when a small molecule (e.g., less than 300 Da) is bound or associated to the bioentity immobilized on the surface of the biosensor. Thus, in various aspects, the biosensors described herein can detect a conformational change of a bioentity when a binding molecule of molecular weight of less than 300, less than 275, less than 250, less than 225, less than 200, or less than 150 Da is bound to the immobilized bioentity. Examples of other binding molecules useful herein include, but are not limited to, an ion, a metabolite, a supramolecular assembly, a nanoparticle, a polymer, or a second bioentity. In one aspect, a second binding molecule is bound to the immobilized bioentity on the first surface, wherein the second binding molecule occupies a specific location on the immobilized bioentity. In this aspect, the addition of the second binding molecule can be used to determine whether or not degradation is active site related.

Alternatively, the biosensors as described herein can be used to detect conformational changes of a bioentity from a binding molecule produced from a previous reaction. In this aspect, the biosensor is used to assay the existence of a newly formed chemical from a prior reaction. It is contemplated that the prior reaction may have been performed either offline to the biosensor or while in the presence of the biosensor. Thus, in this aspect, the biosensor is used as a diagnostic or indicator for the presence of a particular molecule (i.e., binding molecule).

It is known in the art that enzyme fragmentation compliment can be used to provide a very sensitive high throughput screen for a number of intracellular functional GPCR assays. In these cases, screens are developed in which an inactive fragment of a lytic enzyme such as a protease or any digesting enzyme is allowed to combine with a complimenting fragment that renders the complex active. It is contemplated that these same assay designs may be assayed on a biosensor. The two fragments are referred to as enzyme donor and enzyme acceptor. The receiving enzyme fragment is termed the enzyme acceptor. The fragment that completes enzyme activity and is used as a probe is termed an enzyme donor. The enzyme donor fragments that induce complementation and activation of the lytic enzyme are then conjoined to element for screening. The elements for screening may be a drug or metabolite that is covalently conjugated to the enzyme fragment that completes the lytic activity of the enzyme. Alternatively, the elements for screening can be genetically fused through recombination to the enzyme fragment that completes the lytic activity. Competition assays can be developed between the enzyme donor and endogenous non-labeled materials such as metabolites. For example, cyclic AMP can be covalently conjugated to an enzyme donor. When cyclic AMP from a cell lysate is added to the CAMP labeled enzyme donor fragment it will result in an attenuation of digestion performance. On a biosensor this attenuation is measured over time.

The binding molecule can be bound to the bioentity using techniques known in the art. For example, the biosensor with the immobilized bioentity can be exposed to a solution containing the binding molecule. As used herein, the term "exposing" is defined as an instance of exposure by close physical contact of at least one substance to another substance. This definition applied throughout all of the methods described herein. The interaction between the binding molecule and the bioentity can result in a covalent bond or a non-covalent interaction (e.g., electrostatic, ionic, hydrogen bonding, dipole-dipole, van der Waal, and the like).

After the binding molecule is bound to the immobilized bioentity, the biosensor is exposed to a degrading agent. The terms "degrading" or "degradation" as used herein are defined as any process that results in the reduction of initial mass of a bioentity. The degrading agents described herein can modulate (i.e., increase, decrease) the rate of degradation. The degrading agent can react with the bioentity in a number of ways depending upon the selection of the degrading agent and the bioentity. In one aspect, the degrading agent can be used to cleave one or more bonds (e.g., covalent or non-covalent) present in the bioentity.

In one aspect, the degrading agent comprises one or more chemical compounds, one or more enzymes, or a combination of one or more chemical compounds and enzymes. Examples of chemical compounds include, but are not limited to, an oxygen radical, a hydroxyl radical, a superoxide anionic oxygen radical, an acid, or a base. Other examples of chemical compounds include, but are not limited to, CNBr, trifluoroacetic acid, or magnesium chloride. In other aspects, the degrading agent comprises an enzyme, wherein the enzyme comprises an extracellular protease, a metalloproteinase, a natural or synthetic protease (e.g., endopeptidases, exopeptidases, sulfhydryl proteases such as papain, metallopeptidases such as leucine aminopeptidases, carboxypeptidases), a natural or synthetic nuclease (e.g., a ribozyme)), a glucosidase, a lipase, an amylase, a galactosidase, a maltase, an ammonia lyase, a decarboxylase, a phosphorylase, a phosphodiesterase, a dioxygenase, a hydroxylase, a cholinesterase, a Ubiquitin-proteasome system (UPS), or a mixture thereof. In another aspect, the enzyme is a nucleic acid enzyme, where a variety of specific nucleases with a great diversity in sequence restriction digest sites as well as polarity of digestion can be used. Examples of nucleic acid enzymes are available from New England Biolabs. In another aspect, the enzyme comprises trypsin, chymotrypsin, DNAse I, proteinase K, papain, pepsin, Lys C, Asp N, exonuclease III, Eco RI, BAM HI, RNase H, RNAse A, RNAse T1, or RNase V1. It is also contemplated that the degrading agent can be in the form of energy such as heat, electromagnetic energy such as X-ray, radiation, UV-visible, electrolysis, ion beam, or photolysis. Depending upon the bioentity that is selected, two or more enzymes or chemical compounds may be required in order to promote a conformational change in the bioentity. Here, multiple enzymes and/or chemical compounds may be required to produce a distinct degradation pattern.

The degrading step (b) can be optionally performed in the presence of a degrading catalyst. The term "degrading catalyst" is any compound that can modulate (i.e., increase or decrease) the rate of degradation of the bioentity but is not consumed in the reaction. It is contemplated that the degrading catalyst can be used in combination with the degrading agent or be used as the degrading agent itself. Examples of degrading catalysts include, but are not limited to, a surfactant, a denaturant, a metalloorganic complex, an ion, a metabolite, a peptide, a peptide nucleic acid, a protein, a lipid, a carbohydrate or a mixture thereof. In one aspect, a copper porphyrin can be used as the degrading catalyst. Examples of degrading catalysts useful herein include those synthesized in Groves et al., *J. Am. Chem. Soc.*, 2004, 126, 12833-12842.

It is contemplated that any conformationally altered ligand-bioentity complex can be further confirmed or characterized through secondary analysis such as peptide digest mapping, deuterium exchange studies, Michaelis-Menten kinetic studies, circular dichroism, intrinsic fluorescence analysis, competition studies with fluorescence polarization assays and the like. In addition, the effects that a ligand or putative ligand may have on the digesting agent may be analyzed using a known non-binding agent or through kinetic analysis using fluorescent assays or absorbance assays. For example, rhodamine 110, bis-(CBZ-L-isoleucyl-L-prolyl-L-arginine amide), dihydrochloride (BZiPAR, Invitrogen Inc.) may be used in fluorescence assays with trypsin and a putative ligand. Similarly, $N_\alpha$-benzoyl-L-arginine ethyl ester hydrochloride (BAEE) may also be used for spectrophotometric assays with trypsin and other proteases.

In one aspect, prior to exposing the immobilized bioentity and the bound binding molecule to the degrading agent, a degrading modulator can be added. In certain circumstances, it may be desirable to modulate (i.e., increase or decrease) the rate of degradation. Examples of degrading modulators include, but are not limited to, protease, nuclease or amylase inhibitors or enhancers. In one aspect, the degrading modulator can be a degrading inhibitor or competing ligand to inhibit the rate of degradation. Methods for screening (e.g., high-throughput) degrading modulators will be discussed below.

In another aspect, prior to exposing the immobilized bioentity with the degrading agent, at least one group on the immobilized-bioentity is modified with a modifying agent in order to increase or decrease the rate of degrading of the bioentity. As will be discussed below, the modification of the bioentity involves the use of different types of compounds depending upon the desired increase or decrease in rate of degradation. The modification of the bioentity can be performed (1) prior to immobilization on the biosensor, or (2) after immobilization but prior to or after exposure of the immobilized bioentity to the binding molecule.

In one aspect, the modifying agent comprises a crosslinking agent. Crosslinking agents are compounds that when covalently or non-covalently attached to the bioentity reduce the rate of degradation by crosslinking or attaching to different sections of the bioentity. The crosslinkers can possess one or more different groups capable of interacting with various groups present on the bioentity (i.e., homofunctional or heterofunctional). The number of groups present on the crosslinking agent can also vary. For example, when the bioentity is a protein, the crosslinking agent can possess two or more groups that can interact with various amino acids and prevent unfolding (i.e., a conformational change) of the protein. In addition, hetero-bifunctional cross-linking agents can vary through distance between reactive end groups. These lengths of separation between cross-linking groups can provide specific steric or structurally relevant properties. Examples of crosslinking agent useful herein include, but are not limited to, (N-(4-maleimidobutyryloxy)succinimide-N-succinimidyl-4-maleimidobutyrate), (sulfosuccinimidyl-4-N-maleimidomethyl cyclohexane-1-carboxylate), (1-ethyl-3-[3-dimethylaminopropyl]carbodiimide hydrochloride), psoralen, glutaraldehyde, or a mixture thereof. In another aspect, the crosslinking agent is photoactivated.

In another aspect, the modifying agent comprises a chemical agent that reduces the rate of degrading. One or more groups present on the bioentity can be reacted with a chemical agent so that the molecular weight of the bioentity can be increased. By increasing the molecular weight of the bioentity, when the bioentity undergoes a conformational change, the conformational change can be more readily detected by the biosensor due to the increase in molecular weight of the bioentity. For example, the bioentity may have hydroxyl, amino, or carboxylic acid groups that can react with a modifying agent to produce an ether group, a substituted amino or amide group, or ester group, respectively. The chemical modification of bioentities will be discussed in greater detail below.

In one aspect, described herein is a method for screening the ability of a binding molecule to change the conformation of a bioentity, comprising:

a. immobilizing the bioentity on a first surface and second surface of a biosensor that can detect a change in refractive index;

b. binding a binding molecule to the bioentity immobilized to the first surface of the biosensor;

c. exposing the immobilized components in step to one or more degrading agents such that the immobilized bioentity on the first and second surface of the biosensor react with the degrading agent;
d. measuring the change in the refractive index of the immobilized bioentity on the first and second surface of the biosensor; and
e. comparing the refractive index of the immobilized bioentity on the first and second surface of the biosensor, wherein a difference in refractive index between the immobilized bioentity on the first surface and the immobilized bioentity on the second surface indicates a conformational change when the binding molecule is bound to the immobilized bioentity.

As described above, the methods described herein can be used to screen a variety of binding molecules for their ability to induce a conformational change in a bioentity. For example, if a known drug (i.e., binding molecule) induces a specific conformational change in a particular biomolecule that is detected by the biosensor, then other binding molecules can be tested in order to induce a similar if not identical conformational change. Methods and techniques for detecting conformational changes in the immobilized bioentities will be discussed in detail below. Thus, the biosensors described herein can be a useful research tool in identifying binding molecules such as pharmaceutical drugs for treating or preventing diseases in a subject.

In another aspect, described herein is a method for determining the conformation of a diseased bioentity, comprising:
a. immobilizing a non-diseased bioentity on a first surface of a biosensor, immobilizing a diseased bioentity on a second surface of the biosensor, wherein the biosensor can detect a change in refractive index,
b. exposing the immobilized components in step (a) to one or more degrading agents such that the immobilized bioentity on the first and second surface of the biosensor react with the degrading agent;
c. measuring the change in the refractive index of the immobilized bioentity on the first and second surface of the biosensor; and
d. comparing the refractive index of the immobilized bioentity on the first and second surface of the biosensor, wherein a difference in refractive index between the immobilized bioentity on the first surface and the immobilized bioentity on the second surface indicates a conformational change in the diseased bioentity when compared to the non-diseased bioentity.

In general, it is desirable to determine whether or not a subject possesses a disease or is predisposed to a disease. Thus, if a conformation of a diseased bioentity is known, it can be used as a control to determine if a subject possesses the diseased bioentity. The term "diseased bioentity" is defined herein as any bioentity that directly causes a disease in a subject or predisposes the subject to a disease. A non-diseased bioentity is a bioentity that does not directly cause a disease in a subject or predispose the subject to a disease but can be converted to a diseased bioentity by changing the conformation of the non-diseased bioentity. For example, this method can be used to compare the native state of a protein relative to a protein that is extracted from a patient's serum. Many disease states are affected by mis-folded proteins such as prions in neurological diseases and ataxin-3 protein in Machado-Joseph disease.

Degradation and catabolism is a critical component of metabolism and normal cellular function. Many regulatory networks and pathways are affected by availability of functioning biological components. The collective degradation of all components or bioentities within a cell is called the degradome and constitutes a phenotypic signature. The substrate components can be RNA, DNA, carbohydrates, fats, proteins and the like. The degradation agents include, but not limited to, a lipase, a protease, a glycosylase, an extracellular protease, a metalloproteinase, a nuclease, a glucosidase, an amylase, a galactosidase, a maltase, an ammonia lyase, a decarboxylase, a phosphorylase, a phosphodiesterase, a dioxygenase, a hydroxylase, a cholinesterase and so on. All components, either the targets of digestion or the endogenous agents that cause digestion, are subject to "degradomic" studies on the biosensor. Degradation of these components can affect regulatory networks, susceptibility to viral infection, immune function and pathways. Accurate, high-throughput screening of the global degradome by a biosensor without the requirement of labels can provide a detailed survey of what degradation processes within a cell are dysfunctional and related to disease.

Some diseases can also be related to disruption in the degradation process either by alterations in the normal degrading bioentity or by alterations in the normal agent(s) that cause degradation. Alterations in either the substrate or the degrading agents can be in many forms including, but not limited to, misfolding, altered transport, post-translational modifications like methylation, phosphorylation, glycosylation, protein subunit assembly, isoforms and the like. In addition, exposure of a cell to external agents like a drug can cause a reaction process, which impacts the degradome and results in an altered digestion profile. This degradation profile can be correlated to other phenotypic signatures such as functional proteomic chips, metabolic chips (meta-chips), gene expression data, peptidomic profiles, metabolomic profiles, single nucleotide polymorphic profiles and the like. These degradation profiles can be diagnostic, prognostic or can yield therapeutic targets for subsequent drug development.

The immobilized bioentity as a substrate for degradation is but one possible source of disease. However, even the degrading agent itself can be a source of disease. It is also be possible for a degrading agent to act in a disease manor wherein through alteration such as alternative spliced isoforms or post-translational modification, the degrading agent losses its ability to degrade the appropriate substrate in a normal functioning manor. This failure can result in either an excessively rapid removal of a component in the cellular milieu or can result in an abnormal accumulation of a particular component. Again, this type of condition can be assayed on a biosensor. In this case, comparison between a "normal functioning" degrading agent and a degrading agent from a disease state can be tested for a common substrate on a biosensor. The degrading agents can be in the form of raw or purified extracts, lysates, electrophoretically or chromatographically or affinity purified degrading agents.

In another aspect, the conformation of a bioentity can be changed when the bioentity undergoes digestion. In one aspect, described herein is a method for detecting the conformation of a bioentity, comprising:
a. immobilizing the bioentity on a first surface and second surface of a biosensor that can detect a change in refractive index;
b. exposing the immobilized components in step (a) to one or more degrading catalysts such that the immobilized bioentity on the first and second surface of the biosensor react with the degrading catalyst;
c. measuring the change in the refractive index of the immobilized bioentity on the first and second surface of the biosensor; and d. comparing the refractive index of the immobilized bioentity on the first and second surface of the biosensor, wherein a difference in refractive index between the immobilized bioentity on the first surface and the immobilized bioentity on the second surface indicates a conformational change.

This method is referred to herein as catalytic digestion. Catalytic digestion involves the use of a degrading catalyst to modulate (i.e., increase or decrease) the digestion activity of a bioentity. In certain aspects, degrading catalyst is not consumed in the reaction. It is contemplated that the degrading catalyst can be used in the absence or presence of a degrading agent. Examples of degrading catalysts include, but are not limited to, a surfactant, a denaturant, a metalloorganic a complex, an ion, or a mixture thereof. In one aspect, a copper porphyrin can be used as the degrading catalyst. Examples of degrading catalysts useful herein include those synthesized in Groves et al., *J. Am. Chem. Soc.*, 2004, 126, 12833-12842. The degrading catalyst can also be obtained from a prior reaction, where upon production or release of the catalyst, the catalyst is assayed on the biosensor and compared to digestion reactions not containing degrading catalyst.

The degrading catalyst of such a system could be used to enable digestion where normal digestion is not possible. The catalysts can be used synergistically as an enhancement aid to detect small ligand binding events as would be performed during a drug digestion screen. Finally, the use of degrading catalysts can be used to profile conformational stability of a bioentity.

In another aspect, described herein is a method for detecting the conformation of a bioentity, comprising:
a. immobilizing the bioentity on a first surface and second surface of a biosensor that can detect a change in refractive index;
b. denaturing the immobilized bioentity on the first surface of the biosensor with one or more denaturing agents;
c. exposing the immobilized components to one or more degrading agents such that the immobilized bioentity on the first and second surface of the biosensor react with the degrading agent;
d. measuring the change in the refractive index of the immobilized bioentity on the first and second surface of the biosensor; and
e. comparing the refractive index of the immobilized bioentity on the first and second surface of the biosensor, wherein a difference in refractive index between the immobilized bioentity on the first surface and the immobilized bioentity on the second surface indicates a conformational change.

This method is referred to herein as pulse digestion. In one aspect, an immobilized bioentity is digested over a discrete time while in the presence of denaturing agent. In another aspect, the exposure time of the bioentity to the denaturing agent is controlled and the bioentity is exposed to a degrading agent after removal of the denaturing agent. In the pulse digestion method, the equilibrium of the conformation of the bioentity is "challenged" or shifted by the denaturant. After or during the "challenge" to the conformational state, the bioentity is then digested for a discrete controlled time period, where the digestion is monitored on a biosensor described herein. The amount of denaturing agent can be determined empirically in order to either control the number of wells required to run the assay or the number of wells to obtain the highest "resolution" of the transition event. The pulse digestion techniques described herein have numerous applications including, but not limited to, (1) detection of ligand binding, (2) detection of macromolecular interactions, or (3) detection of the physical state of the bioentity (i.e., detection of misfolded states of bioentities). Alternatively, the pulse digestion methods can be used to assay chemicals produced from a previous reaction and subsequently detected on the biosensor.

The biosensors described herein can also be used to evaluate digestion modulators (e.g., enhancers and inhibitors). In one aspect, described herein are methods for determining the ability of a compound to modulate the digestion of a bioentity, comprising:
a. immobilizing the bioentity on a first surface and second surface of a biosensor that can detect a change in refractive index;
b. admixing the compound with the immobilized bioentity on the first surface;
c. exposing the immobilized components to one or more degrading agents such that the immobilized bioentity on the first and second surface of the biosensor react with the degrading agent;
d. measuring the change in the refractive index of the immobilized bioentity on the first and second surface of the biosensor; and
e. comparing the refractive index of the immobilized bioentity on the first and second surface of the biosensor, wherein a difference in refractive index between the immobilized bioentity on the first surface and the immobilized bioentity on the second surface indicates whether or not the compound modulates digestion.

The digestion inhibitors could be directed against any lytic agent including, but not limited to, peptidases (e.g., Caspase assay), proteases, nucleases, glucuronidase, glucosidase, and the like. In another aspect, molecules that enhance digestion can be identified by biosensor-based screens. In another aspect, the potency of a digestion inhibitor can be evaluated against a degrading catalyst. In this aspect, a degrading catalyst is used to expose the bioentity to enhanced digestion, where the extent to which the inhibitor can prevent digestion is assayed. In another aspect, the digestion inhibitor can be evaluated using a denaturing agent as used in a pulse digestion assay. Here, the denaturing agent can be added prior to or during the addition of the degrading agent. Numerous digestion inhibitors can be evaluated using the techniques described herein. In yet another embodiment, cocktails of multiple digestion inhibitors can be evaluated for their collective potency through biosensor based digestion assays. Examples of such digestion inhibitors include, but are not limited to, a trypsin inhibitor, aprotin, EDTA, α-amylase inhibitor (type I and III), N-ethylmaleimide, 4-(2-aminoethyl)-benzene sulfonyl fluoride, benzamide, phosphoramide, leupeptin, chymostatin, bestatin, antipain, 6-aminohexanoic acid, verbascose, planteose, neomycin, or a mixture thereof.

b. Denaturation

In one aspect, described herein are methods for detecting a conformational change in a bioentity, comprising:
a. immobilizing the bioentity on a first surface and second surface of a biosensor that can detect a change in refractive index, wherein a binding molecule is bound to the bioentity immobilized to the first surface of the biosensor, wherein the biosensor is not a gold surface, wherein the binding molecule is bound to the bioentity prior to or after immobilization;
b. exposing the immobilized components in step (a) to one or more denaturing agents such that the immobilized bioentity on the first and second surface of the biosensor react with a denaturing agent;
c. measuring the change in the refractive index of the immobilized bioentity on the first and second surface of the biosensor; and d. comparing the refractive index of the immobilized bioentity on the first and second surface of the biosensor, wherein a difference in refractive index between the immobilized bioentity on the first surface and the immobilized bioentity on the second surface indicates a conformational change when the binding molecule is bound to the immobilized bioentity.

After the binding molecule is bound to the immobilized bioentity using the techniques described above, the biosensor is exposed to a denaturing agent. The terms "denaturing" or "denaturation" as used herein are defined as the disruption of structure of the bioentity and does not involve the cleavage of covalent bonds. For example, DNA exists in the natural state as double-stranded helical structure. Upon denaturation, the DNA is partially or completely converted to a single-stranded conformation. The denaturing agents described herein can modulate (i.e., increase, decrease) the rate of denaturation. The denaturing agent can react with the bioentity in a number of ways depending upon the selection of the denaturing agent and the bioentity. For example, the denaturing agent can increase electrostatic repulsions within the bioentity to cause the bioentity conformation to change. Alternatively, renaturing agents are agents that can facilitate renaturation of the bioentity, which can be desirable under certain circumstances.

In one aspect, the denaturing agent comprises a chemical compound, enzyme or energy source such as heat. In one aspect, the chemical compound comprises a salt, spermidine, a surfactant (e.g., anionic, nonionic, cationic, ampholytic surfactant), or a detergent. In another aspect, the chemical compound comprises urea, guanidinium HCl, sodium chloride, magnesium chloride, or sodium dodecyl sulfate. In another aspect, when the denaturing agent comprises an enzyme, the enzyme comprises a gyrase, helicase, or DNA topoisomerases I and III.

In one aspect, a high index solvent can be present during detection of the conformational change. Examples of high index solvents include, but are not limited to, dimethyl sulfoxide or glycerol. The amount of high index solvent that can be used will vary depending upon the solvent selected and the bioentity that is immobilized. The amount of high index solvent should not be excessive as it may not be possible to subtract out the bulk refractive index effect from a subtle denaturation effect. Bulk refractive index changes by the high index solvent can be referenced. Alternatively, wash steps can be used to reduce or remove excess high index solvents.

The denaturing agent may require time to equilibrate with the biosensor surface and immobilized bioentity. The duration of equilibration can be determined empirically, which will depend upon the solvent and denaturant selected. Monolayers or multilayers of denaturant can be formed on the biosensor surface. The formation of monolayers on the sensor may follow Brunauer-Emmet-Teller (BET) absorption behavior. The BET equation can be used to assess the extent of the denatured state of a biomolecule (see Yamaguchi et al., Biotechnol. Prog. 2003, 19, 1348-1354).

Similar to above, the immobilized bioentity can be modified with a crosslinking agent to reduce the rate of denaturation prior to exposure to the denaturing agent. As discussed above, the crosslinking agent can interact with two or more groups present on the bioentity and, thus, lock the bioentity in a particular conformation, which is resistant to denaturation. In another aspect, the bioentity can be modified with a denaturing modulator to modulate the rate of denaturation. It is contemplated that prior to exposure with the denaturing agent, the immobilized bioentity can be modified with an agent that can increase or decrease the rate-of-denaturation. Examples of denaturing modulators include, but are not limited to, a molecular chaperone, a peptide, a cofactor, DNA, RNA, PNA, a carbohydrate, a lipid, a membrane protein, or a mixture thereof.

In another aspect, prior to exposing the immobilized bioentity to the denaturing agent, a chemical agent that can undergo binding changes upon denaturation of the immobilized bioentity on the first and second surface of the biosensor prior to measuring the difference in refractive index can be added. In this aspect, a chemical agent that would not otherwise react (or would react to a lesser extent) with the immobilized bioentity, upon denaturation, the chemical agent then reacts with the denatured bioentity. In one aspect, the agent comprises a probe such as, for example, an associative hydrophobic probe, a surfactant, or a covalent reactive probe. Specific examples of chemical agents useful herein include, but are not limited to, 8-anilino-1-naphthalene-sulphonic acid, triton X-100, ethidium bromide, or glutaraldehyde. The use of probes to investigate conformational changes is addressed in greater detail below.

As described above, the methods described herein can be used to screen a variety of binding molecules for their ability to induce a conformational change in a bioentity. In one aspect, described herein is a method for screening the ability of a binding molecule to change the conformation of a bioentity, comprising:

a. immobilizing the bioentity on a first surface and second surface of a biosensor that can detect a change in refractive index;

b. binding a binding molecule to the bioentity immobilized to the first surface of the biosensor;

c. exposing the immobilized components in step to one or more denaturing agents such that the immobilized bioentity on the first and second surface of the biosensor react with the denaturing agent;

d. measuring the change in the refractive index of the immobilized bioentity on the first and second surface of the biosensor; and e. comparing the refractive index of the immobilized bioentity on the first and second surface of the biosensor, wherein a difference in refractive index between the immobilized bioentity on the first surface and the immobilized bioentity on the second surface indicates a conformational change when the binding molecule is bound to the immobilized bioentity.

C. Chemical Modification

As described above, one or more groups present on the immobilized bioentity can be modified with a modifying agent in order to increase the overall molecular weight of the immobilized bioentity. The increase in molecular weight can provide a measure of the availability of reactive functional groups on the immobilized bioentity. This availability provides a "covalent signature" of conformational state. The bioentity can be modified prior to and/or after immobilization on the biosensor. The modifying agent can form a covalent or non-covalent bond with the bioentity. The modifying agents can be selected by functional group reactivity, molecular weight, and steric properties such as, for example, distance of separation between reactive ends of a cross linking agent. The introduction of the chemical modifier is primarily for producing a detectable mass shift on a biosensor. However, the chemical itself may impart physical properties to the bioentity that are beyond just a mass shift. The chemical modifier can also impart either an electrostatic charge or steric effects, which are useful in subsequent assay methodology. Subsequent assay methodologies can include but are not limited to, ligand binding, macromolecular binding, protein subunit assembly, in situ polymerization, digestion, denaturation, surrogate binding assays, functional modification assays, enzymatic modifications, hapten binding and the like.

In addition, solvent characteristics can be selected to control the reaction properties. In some cases, concentration of cross-linker, reaction conditions and solvents conditions can cause non-specific cross linking agents like glutaraldehyde to self polymerize, thus skewing molecular weight sensitive signal. In other cases, solvent conditions can enhance or reduce chemical reactivity of functional groups. The modifying agent can also introduce a structure that is detectable by other detection techniques known in the art. Some examples would include hapten incorporation, fluorophore incorporation, chemiluminescence tags, tags which enable tyramide precipitation, DNA tags which allow amplification in situ and the like.

In one aspect, described herein is a method for detecting a conformational change in a bioentity, comprising:
a. immobilizing the bioentity on a first surface and second surface of a biosensor that can detect a change in refractive index, wherein at least one group in the bioentity immobilized to the first surface of the biosensor is modified with a modifying agent to increase the molecular weight of the immobilized bioentity, wherein the modification is performed prior to or after the bioentity is immobilized;
b. measuring the change in the refractive index of the immobilized bioentity on the first and second surface of the biosensor; and
c. comparing the refractive index of the immobilized bioentity on the first and second surface of the biosensor, wherein a difference in refractive index between the immobilized bioentity on the first surface and the immobilized bioentity on the second surface indicates a conformational change when the immobilized bioentity is modified.

The bioentity can be modified using techniques known in the art. In certain aspects, it may be desirable to wash the immobilized bioentity after modification. The washing step can (a) remove unbound modifying agent, (b) control the extent of the chemical reaction (modification) and (c) exchange initial buffer with another buffer that has a different bulk refractive index. It is also contemplated that a secondary chemical can be added to control or stop the chemical reaction between the immobilized bioentity on the biosensor and the modifying agent. Secondary chemicals can be added after chemical modification is done. The secondary chemicals contain functional groups that also react with the modifying agent but do not contribute to any detectable mass change on the surface since they are not immobilized. The addition of the secondary agent quenches any free modifying agent in an effort to control the amount of signal generated during a cross linking reaction.

In one aspect, proteins, amino acids or sets of amino acids can be selectively modified by a number of chemicals. Some protocols require denaturation for complete modification of those relevant amino acid residues while others are sufficiently through with just the native state. In other aspects, less selective perturbations of functional groups can involve pH shifts or ion concentration effects that modulate the electrostatic properties of the biomolecules. Techniques for modifying proteins are disclosed in Glazer, A. N., Delange, R. J. and Sigman, D. S. Laboratory Techniques in Biochemistry and Molecular Biology: Chemical Modification of Proteins, Elsevier Science & Technology Books, 1975. ISBN: 0444108114, which is incorporated by reference for its teachings with respect to chemical modifications of proteins. Table I provides examples of modifying agents useful herein for modifying proteins.

TABLE I

| Amino acid modification | Chemical for modification |
|---|---|
| amidation of primary amines ($NH_2$) | ethylacetimidate HCl |
| guanidination of α and ε $NH_2$ | 1-guanyl-3,5-dimethyl pyrazole |
| tyrosyl carbamylation | HNCO |
| to limit or restrict tryptic digestion trifluoroacetylation of $NH_2$ groups | ethylthioltrifluoroacetate (pH 10) |
| to selectively limit tryptic digestion to lysine, protect the lysine through citraconylation prior to butanedione reaction of arginine residues | 2,3-butanedione |
| thiol modification (Cysteine) | Ellman's reagent (DTNB) 5,5'-dithiobis (2-nitrobenzoate) 2-nitro-5-thiocyanobenzoate (NTCB) |
| iodination of tyrososine | HOI |
| nitration of tyrosine | tetranitromethane (TNM) |
| tryptophan | 2-(2-nitrophenylsulfenyl)-3-methyl-3-bromoindolenine (BNPS-skatole) N-bromosuccinimide formic acid 2-nitrophenylsulfenyl chloride |

Mass spectroscopy or other analytical techniques on the fragments of the bioentity (e.g. pre-post chemical modification via for example proteolytic digests) can be used to determine the exact location of covalent modification. In some cases, identification of the location of the modification by itself may be sufficient to identify ligand association. The chemical modification can be done either during or after the biochemical or chemical process. The secondary analytical detection methods can be used as supportive aids in confirming biosensor detected modifications for a screen. Comparisons between modifications done with known active site ligands are possible. In addition, hydrogen-deuterium exchange reactions could be used to offer detailed assessments of "within molecule" structural properties. Techniques such as, for example, mass spectrometry coupled with hydrogen exchange can aid in mapping the isotopic exchange effects. Desorption electrospray ionization mass spectrometry (DESI-ms) can also aid be used in yielding higher throughput detection.

In another aspect, a nucleic acid or carbohydrate can also be chemically modified. In one aspect, a nucleic acid structure is chemically modified at specific functional groups and assayed for its structure either in the absence or presence of a binding partner. An example is RNA in the ribosome. Examples of modifying agents for the modification of nucleic acids include, but are not limited to, Kethoxal, fotemustine, dimethylsulfate, or 4-(2'-bromoethyl phenol). Other examples of modifying agents include sulfo-EGS, (p-azidophenyl glyoxal monohydrate), (4-(p-azidosalacilamido)) butylamine, or (bis-sulfosuccinimidyl)suberate).

In another aspect, the modifying agent comprises a second bioentity. For examples, when the second bioentity is a hapten such as biotin or digoxygenin, the second bioentity can be reacted with a large molecular weight mass binder such as streptavidin, streptavidin coated onto a nanoparticle, or streptavidin conjugated to a nucleic acid structure, which is subsequently used in an in situ polymerization or precipitation reaction for signal amplification on the biosensor surface.

It is also contemplated that prior to or after modification of the bioentity, the bioentity can be degraded or denatured using any of the techniques described herein. For example, after modifying the immobilized bioentity, the immobilized bioentity can be degraded by a degrading agent such as, for example, an enzyme.

It is contemplated that the modifying agent can introduce additional properties to the immobilized bioentity besides increasing the molecular weight. For example, the modifying agent can modulate the electrostatic charge, polarity, hydrophobicity, solvent shell, ion shell, van Der waal forces, and the like of the immobilized bioentity. In one aspect, the modifying agent introduces a physical property to the immobilized bioentity useful to either multimodal detection-or subsequent reactions on the biosensor such as macromolecular assembly, ligand binding, surrogate binding, modulation of digestion or modulation of denaturation. For example, the modifying agent can be fluorescent, chemiluminescent or provide a novel new Raman band signature that could be used in multimodal detection.

Similar to above, the chemical modification of immobilized bioentities can be useful in screening the ability of bioentities to change the conformation of the bioentity. In one aspect, described herein is a method for screening the ability of a binding molecule to change the conformation of a bioentity, comprising:
b. immobilizing the bioentity on a first surface and second surface of a biosensor that can detect a change in refractive index, wherein at least one group in the bioentity immobilized to the first surface of the biosensor is modified with a modifying agent to increase the molecular weight of the immobilized bioentity, wherein the modification is performed prior to or after the bioentity is immobilized;
c. binding a binding molecule to the bioentity immobilized to the first surface of the biosensor;
d. measuring the change in the refractive index of the immobilized bioentity on the first and second surface of the biosensor; and
e. comparing the refractive index of the immobilized bioentity on the first and second surface of the biosensor, wherein a difference in refractive index between the immobilized bioentity on the first surface and the immobilized bioentity on the second surface indicates a conformational change when the binding molecule is bound to the immobilized bioentity.

The chemical modification of bioentities has numerous applications. In one aspect, the rate or extent of modification can be used as a means of detecting changes in conformation induced by recognition. In another application, chemical modification can be used to determine how a group of residues affects the binding between a binding molecule and the bioentity. Thirdly, chemical modification can be used to alter the reactivity of the immobilized target for subsequent degradation or denaturation reactions. In another aspect, chemical modification can limit digestion (e.g., enzymatic) to one or more components within a complex biomolecular species. In this aspect, one may want to observe either chemical reactivity or degradation of one molecule while it is complexed to an immobilized target protein. In order to observe degradation or reactivity events solely restricted to one of the-partner molecules, it may be desirable to "quench" the reactivity of the functional groups in the partner molecule. In one aspect, a first bioentity can be immobilized and allowed to completely react with a modifying agent. This results in a chemically inert anchor for building a macromolecular complex. After removing excess modifying agent, one or more bioentities can complexed to the biosensor. The complex can now be assayed for either chemical reactivity or selective degradation. In addition, the chemical modification can induce a susceptibility to subsequent chemical alterations such as seen in Edman degradation. Furthermore, the chemical modification can also be employed to the non-immobilized partner bioentity.

A quantitative measurement of the amount of chemical modification can be made on the biosensor. In this aspect, the amount of bioentity immobilized onto the biosensor prior to chemical modification can be measured. Then after allowing the modifying agent to react with the immobilized bioentity over a given time frame and within a given solution condition, the change in refractive index is measured. In the event that the modifying agent reacts with the attachment chemistry, the following precautions can be made. Subtraction or adjustment for non-specific chemical modification to the attachment chemistry is possible through control reactions. It can be determined if the chemical modifier reacts with the attachment chemistry on the sensor by measuring for mass shifts in absence of immobilized bioentity. Taking the ratio of the corrected amount of chemical modification done on the immobilized bioentity relative to the initial amount of immobilized bioentity will result in a calculated fractional amount of chemical modification. The fractional amount of modification can be converted to percentage of chemical modification by multiplying by 100. This percentage of chemical modification is a useful metric for comparing modulating conditions such as ligand binding, temperature changes, chemical denaturation, solvent changes and the like. When ligand effects are examined using chemical modification, it may be necessary to select chemical modifiers for specific functional group reactivity that is restricted to within the immobilized bioentity.

d. Surrogate Binding

In another aspect, one or more probes can be used to "sense" interactions and conformational transitions using the biosensors described herein. When the probe associates with the bioentity, the probe produces a distinct signal that can be detected by the biosensor and produce a signature of a specific type of interaction. Similarly, when the probe fails to associate with the immobilized bioentity, this can provide a signature of alteration in structure or conformational state of a bioentity.

In one aspect, described herein is a method for detecting a conformational change in a bioentity, comprising:
a. immobilizing the bioentity on a first surface and second surface of a biosensor that can detect a change in refractive index, wherein at least one group in the bioentity immobilized to the first surface of the biosensor is modified to increase the molecular weight of the immobilized bioentity, wherein the modification is performed prior to or after the bioentity is immobilized, wherein the biosensor is not a gold surface;
b. binding a probe to the bioentity immobilized to the first surface of the biosensor;
c. measuring the change in the refractive index of the immobilized bioentity on the first and second surface of the biosensor; and
d. comparing the refractive index of the immobilized bioentity on the first and second surface of the biosensor, wherein a difference in refractive index between the immobilized bioentity on the first surface and the immobilized bioentity on the second surface indicates a conformational change when the immobilized bioentity is modified.

The nature of the probe and the bioentity will dictate the type of interaction (covalent or non-covalent) that results between the two molecules. The association between the probe and the bioentity can be amphiphilic, hydrophobic (non-polar), ionic, stereo-specific (e.g. structural), affinity based, partitioning and the like. In certain aspects, hydrophobic probes can be useful in detecting folding transitions in bioentities by thermal or chemical denaturation.

In one aspect, the probe comprises an ion, a ligand, a small molecule, a hydrophobic probe, an amphiphilic probe, an aptamer, or an antibody, or a photoreactive probe, where the close association between the photoreactive probe and the bioentity results in photocrosslinkage. The probes useful herein can be label-independent (e.g., non-fluorescent) or a non-label-independent probe. In the case of non-label-independent probes, fluorescent compounds can be used. For example, Molecular Probes Inc. (now owned by Invitrogen) has a broad range of molecules that convey molecular interactions by fluorescence. Other inexpensive protein probes include, but are not limited to, India ink, coomassie blue, surfactants such as Triton X-100, ponseau S, and SDS.

In one aspect, the probe undergoes a physical perturbation through an externally supplied source of energy. For example, if the probe can absorb photons or electromagnetic energy at a different level than the immobilized bioentity, the probe may undergo physical changes that lead to dissociation of the probe from the bioentity. In one aspect, an ANS probe associated with calmodulin immobilized on the biosensor is exposed to a light source where only ANS absorbs the energy. In this aspect, the ANS may be able to photodissociate the surrogate ligand and provide a mass change sufficiently high enough for detection. Ultimately, the pulsed energy can be assigned to a particular conformational change when the probe was associated with the bioentity. Furthermore, the associative ligand can be either chemically cross-linkable or photo-cross-linkable (under certain photon wavelengths) to the immobilized bioentity. This can permit covalent retention of the associative surrogate agent.

In one aspect, the immobilized bioentity can be contacted with a degrading agent (e.g., chemical/enzymatic), a denaturation agent (e.g., chemical/enzymatic/thermal), a secondary probe, a degrading catalyst, an isotope solvent (e.g., deuterium exchange), digestion, or any combination thereof prior to or after binding (i.e., association) with the probe. Any of these reagents can produce a conformational change that in combination with the probe produce a detectable signal associated with the conformational change. For example, enzymatic dephosphylation (e.g. alkaline phosphatase) of an immobilized phosphate containing substrate is difficult to detect on a biosensor. However, the addition of an anti-phosphate antibody can provide sufficient mass recognition to make phosphorylation or dephosphorylation detectable on a biosensor. Affinity recognition as a surrogate binder can make detection of subtle digestion or degradation changes on a biosensor possible. Those knowledgeable in the art will recognize that a broad number of functional assays are possible through these techniques. In one aspect, a secondary probe can detect compound recognition on the biosensor either by direct binding or through indirect association with the portions of immobilized bioentity.

In other aspects, the methods described herein can detect the presence of one or more compounds in solution (e.g., a patient sample). In one aspect, described herein is a method for detecting the presence of a compound, comprising:
a. contacting the compound with a bioentity that binds the compound, wherein the bioentity is immobilized on the surface of a biosensor that can detect a change in refractive index;
b. measuring the change in the refractive index of the immobilized bioentity on the surface of the biosensor; and
c. comparing the refractive index produced in step (b) with a control, wherein the control comprises the refractive index produced by the compound and the immobilized bioentity, wherein if the two refractive indices are similar or identical, the compound is present.

The methods described herein can be used as secondary screens for assaying molecular events that have occurred "off line." For example, in one chemical or biochemical system, an assay or reaction that produces a by-product can be subsequently used on the biosensor in a conformational assay. The conformation of the bioentity can be assayed using any of the techniques described herein including, but not limited to (1) enzymatic or chemical digestion; (2) enzymatic, thermal, energy, or chemical denaturation; (3) associative binding probe assays such as hydrophobic, amphiphilic, affinity, ionic, stereo-specific association to an agent immobilized on a biosensor; (4) catalytic digestion; (5) pulse proteolysis; and (6) isotope solvent effects such as hydrogen-deuterium exchange mapping which involves conformational analysis with mass spectrometry.

In one aspect, a bioentity is immobilized onto the biosensor that undergoes a conformational change due to the binding of an ion. The ion induced conformational change can be assayed using any of the techniques described herein. The source of ions can be derived from a prior assay wherein the change in ion concentration is not assayed. For example, cells, chemical or biological systems can be exposed to a drug that induces the release or uptake of calcium ions. The change in ion concentration is subsequently measured on the biosensor. In one aspect, an example of calcium ion detection would be the use of ANS to bind calmodulin.

In another aspect, changes in the digestion signature can be used to measure the absence or presence of a digestion inhibitor that was produced from a prior reaction. In this aspect, cells or chemical/biological systems can be exposed to drugs that cause the system to release or uptake digestion inhibitors that can be measured on the biosensor. In other aspects, chemicals that undergo either enzymatic or chemical reactions and converted to inhibitors can be subsequently assayed on a biosensor for digestion effects. In a further aspect, chemicals that undergo a reaction causing the loss of inhibitor potential can be subsequently assayed on the biosensors described herein.

In another aspect, an initial process or reaction produces an agent that can be subsequently assayed on a biosensor using a denaturation process. The agent produced in the previous reaction causes a measurable change in the denaturation of the immobilized bioentity on the biosensor. Denaturation can be caused by chemical, enzymatic, thermal or energy exposure. For example, an assay is run where a ligand is produced from a previous cellular assay (e.g. a drug added to cells that causes the release or uptake of an agent), which is then exposed to a biosensor that has an immobilized bioentity that undergoes a measurable change detected by a denaturation profile.

The methods involve the use of a control, where the target compound to be detected has a particular or distinct signal or pattern produced by the biosensor. The pattern is particular to the compound and the conformational change the compound produces when exposed to the immobilized bioentity. For example, a known active site ligand can produce a distinctive signature. The signal produced by the target compound can be identical or similar to that of the control. In the case when the signal is not identical but similar to the control, it is possible that (1) other substances present in the sample (e.g., impurities) can alter the detectable signal, (2) that the ligand docking site is remote from a-control known active site ligand, or (3) that the ligand binds to the same active site in a slightly different way thus causing a conformational change different within the bioentity.

VI. Detection of Conformational Change

The biosensors used herein can detect a change in refractive index. Some conformational changes for bioentities occur through detectable mass changes, while other conformational changes may occur from rearrangement and folding effect that do not constitute a detectable mass change. Thus, when an immobilized bioentity undergoes a conformational change at the surface of the biosensor, detection may require either by direct or indirect assay of the refractive index alterations or modulations on the biosensor. For example, changes in molecular weight at the surface of the biosensor can change the refractive index of the biosensor surface. As discussed above, one or more groups present on the immobilized bioentity can be modified with larger groups so that the molecular weight of the immobilized bioentity increases sufficiently. Alternatively, when a degrading agent cleaves a portion of immobilized bioentity such that a portion of the bioentity is displaced from the surface of the biosensor, the overall molecular weight of the immobilized bioentity is reduced. The detectable change in refractive index can provide useful kinetic or endpoint information. For example, when an immobilized bioentity is exposed to a degrading agent, the rate of degradation can be monitored and quantified by monitoring the signal produced by the biosensor over time, where in general a reduction in signal corresponds to degradation of the immobilized bioentity (i.e., reduction in molecular weight).

In yet another aspect, the detection of a digestion process can be monitored or aided through loss of an associative complex. For example, the digestion of a small molecule by itself may not yield sufficient loss of mass to be reliably detectable on a biosensor. However, a high affinity ligand with enhanced molecular weight (such as an antibody) can be introduced that is directed toward a component of the immobilized agent, which is cleaved off the surface. As the cleavage process continues, a reduction in mass due to absence of recognition by the high affinity ligand can be observed. Either real time subsequent after digestion assays can be detected. Examples include, but are not limited to, (1) an immobilized phosphoylated substrate (2) an anti-phosphate antibody and (3) a phosphatase (alkaline phosphatase). Agents that can add a phosphate include kinases.

In certain aspects, the methods described herein involve label-independent detection or LID. Examples of LID include, but are not limited to, surface plasmon resonance, a resonant waveguide gratings (e.g. Corning Epic™ system), mass spectrometry, capillary electrophoresis, or Raman spectroscopy. The change in refractive index is monitored for polarization effects such as, for example, scattering or TE or TM mode resonance. It is contemplated that non-label-independent detection methods can be used alone or in combination with label-independent detection. Examples of non-label-independent detection include, but are not limited to, fluorescence, phosphorescence, chemilumenescence, bioluminescence, etc. and other techniques generally known to those skilled in the art. One or more different detection techniques can be used in combination with the biosensors used herein (i.e., multi-mode detection) such as, for example, fluorescence, chemiluminescence, mass spectroscopy, gel electrophoresis, HPLC, capillary electrophoresis, conductive biosensors, circular dichroism, microcalorimetry, differential scanning calorimetry, nuclear magnetic resonance, Fourier transform infrared spectroscopy, ultraviolet visible spectroscopy, electron spin resonance, or Raman spectroscopy.

In another aspect, a macro- or microfluidic interface can be used with the biosensor, which can control or aid in the observation of a conformational change. For example, a compound to be assayed can be introduced to the biosensor in a variety of ways, including direct air flow as well as fluid capture/flow. In other aspects, fluid (e.g., gas, aerosol, or liquid) flow across the biosensor is contemplated. Fluids can be introduced either with macro or micro-fluidic systems, and incorporate reagents for inducing conformational changes. In one aspect, a network of channels made up of a number of different macro or microstructures can be used, which can encourage efficient mixing of a sample to be assayed. For example, the biosensor is located within or below a micron-sized deep flow channel in which the sample solution and the reference solution flow side-by-side to one another over a sensing region of the biosensor 102. In another aspect, the air-fluid delivery system can include, but is not limited to, a funnel-shaped air sample collector, a replaceable filter, a network of macro or microchannels or passages, and a fan, air handler, or pump to draw air or liquid through the passages. The macro- and microfluidic devices disclosed in U.S. published application no. 20040191765, which is incorporated by reference, can be used herein. In another aspect, microfluidic interfaces manufactured by Biacore can be used herein.

VII. Assaying Biological Samples

As was discussed above, two or more different degrading, denaturing, digestion events and the like may be necessary to produce a particular signal for a conformational change. In certain aspects described herein, the agent that causes the conformational change can be added to the biosensor. In other aspects, cells contain molecules or compounds that can cause conformational changes of bioentities.

In one aspect, described herein is a method for assaying the proteolytic signature of a biological sample, comprising:
a. immobilizing a plurality of proteins or peptides on a first surface and second surface of a biosensor that can detect a change in refractive index;
b. exposing the immobilized proteins or peptides on the first surface to the sample, wherein the sample can induce a mass reduction of the immobilized protein or peptide through cleavage of a covalent bond;
c. measuring the difference in refractive index of the immobilized protein or peptide on the first and second surface of the biosensor; and
d. recording the difference in refractive index of the immobilized protein or peptide on the first and second surface of the biosensor.

This method is referred to herein as assaying the global proteolytic signature of a biological sample. The biological samples useful herein include, but are not limited to, cells, biological extracts, tissues, serums or plasmas. One of ordinary skill in the art will appreciate the necessary care required in handling sensitive biological samples as well as any of the agents described herein.

In one aspect, the biological sample (e.g., a cell) contains agents that can cause a host of proteolytic changes in the immobilized proteins or peptides. Using the biosensor, a proteolytic signature for a diversity of protein and peptide substrates can be obtained. The enzymatic agents that cause the digestion of these bioentities in the sample can provide these signatures either as a whole admixture or through purification of the digesting agents. Depending upon the assay to be performed, the identity of the protein or peptide can be the same or different. Thus, it is contemplated that a plurality of different proteins or peptides can be immobilized on the biosensor. For example, a plurality of different antibodies can be immobilized on a microarray that can interact with an epitope from a cell by affinity capture.

In other aspects, it is desirable to determine whether or not other agents or molecules present in the cell can induce degradative changes (e.g., digestion) in other bioentities besides proteins or peptides. For example, endogenous oligonucleotides (e.g., DNA, RNA), carbohydrates, sugars, lipids, and the like present in diseased cells induce conformational changes of bioentities present in the cell.

Thus, in one aspect, described herein is a method for assaying the degradome of a biological sample comprising:
a. immobilizing a plurality of bioentities on a first surface and second surface of a biosensor that can detect a change in refractive index;
b. exposing the immobilized bioentities on the first surface to the sample, wherein the biological sample can induce a reduction in the mass of the immobilized bioentities through cleavage of a chemical bonds;
c. measuring the difference in refractive index of the immobilized bioentities on the first and second surface of the biosensor; and
d. recording the difference in refractive index of the immobilized bioentities on the first and second surface of the biosensor.

In another aspect, described herein is method for assaying the degradome of a biological sample comprising:
(a) immobilizing a plurality of bioentities on a first surface through the use of one or more affinity capture-agents and second surface of a biosensor that can detect a referenced change in refractive index;
(b) exposing the affinity captured immobilized bioentities on the first surface to one or more known digestion-agents that will cause a known, expected or anticipated reduction in the mass of the immobilized bioentities through cleavage of one or more chemical bonds;
(c) measuring the difference in refractive index of the immobilized bioentities on the first and second surface of the biosensor; and
(d) recording the difference in refractive index of the immobilized bioentities on the first and second surface of the biosensor.

The term "degradome" is defined herein as the interaction between a set of compounds or molecules present in a cell that induces a mass reduction in a bioentity through the cleavage of chemical bonds over a particular time and the bioentities that are substrates for digestion. The bioentities that lose mass are termed substrates as in an enzymatic reaction. The bioentities that enzymatically cause the reduction in mass are termed the degrading agents. The informational study of processes pertaining to the degradome is termed degradomics. The degradome is a complex system. Post-translational modifications are possible for either the digesting enzymes or agents in the degradome or for the substrates that are acted upon. In addition, these complex mixtures can be different within a species or between different species. As a collective phenotypic measure the degradome can be informative for disease states, diagnostics, therapeutics, prognostics, systems biology, metabolic research, and molecular evolutionary theory within and between species. As will be discussed below, these methods are useful in diagnostics for monitoring diseased cells or cells predisposed to a particular disease.

In certain aspects, the methods described herein can be used on any type of cell or groups of cells known in the art. For instance the cells can be from a cultured cell line or a cell isolated from a subject (i.e. in vivo cell population). The cell can have any phenotypic property, status or trait. For instance, the cell may be a normal cell, a cancer cell, a genetically altered cell, etc. "Normal cells" as used herein refer to any cell, including but not limited to mammalian, bacterial, plant cells, that is a non-cancer cell, non-diseased, or a non-genetically engineered cell. Mammalian cells include but are not limited to mesenchymal, parenchymal, neuronal, endothelial, and epithelial cells. The cells can be extracted by physical selection using laser capture microdissection or cryo-capture techniques. Other techniques for cell or tissue collection or extraction can include chromatography, electrophoresis, affinity capture, flow cytometry and the like. A "genetically altered cell" as used herein refers to a cell that has been transformed with an exogenous nucleic acid. The cells can be exposed to the biosensor directly or processed (e.g., lysed) to extract or release one or more molecules or compounds from the cell that are to be assayed. Cell and tissue extracts such as serum, plasma, amniotic fluid, sputum, cerebral spinal fluid and the like are also possible subjects for analysis.

Cancers include, but are not limited to, basal cell carcinoma, biliary tract cancer; bladder cancer; bone cancer; brain and CNS cancer; breast cancer; cervical cancer; choriocarcinoma; colon and rectum cancer; connective tissue cancer; cancer of the digestive system; endometrial cancer; esophageal cancer; eye cancer; cancer of the head and neck; gastric cancer; intra-epithelial neoplasm; kidney cancer; larynx cancer; leukemia; liver cancer; lung cancer (e.g., small cell and non-small cell); lymphoma including Hodgkin's and non-Hodgkin's lymphoma; melanoma; myeloma; neuroblastoma; oral cavity cancer (e.g., lip, tongue, mouth, and pharynx); ovarian cancer; pancreatic cancer; prostate cancer; retinoblastoma; rhabdomyosarcoma; rectal cancer; renal cancer; cancer of the respiratory system; sarcoma; skin cancer; stomach cancer; testicular cancer; thyroid cancer; uterine cancer; cancer of the urinary system, as well as other carcinomas and sarcomas. Some cancer cells are metastatic cancer cells. In some cases, cellular invasion and angiogenesis is aided by extracellular metalloprotinases (MPs) and or serine, threonine, thiol and aspartic proteases either from metastatic cancers or surrounding tissues. Inhibitors of these digesting enzymes and other agents of the cancer degradome are putative targets for anti-cancer and anti-metastatic agents.

In one aspect, known substrates for digestion are pre-immobilized onto a biosensor and are subjected to an amount of test digesting agents contained in cell lysate or test tissue extract. The test extracts or lysates can be treated for digestion agent(s) purification by a number of means such as chromatography, affinity capture, flow cytometry, sedimentation, filtration and the like. The amount of digesting agents in either cell lysates or cell extracts can be standardized or monitored by a number of means including but not limited to dilution, cell number, optical density, reference to control substrates with robust digestion profiles. Digestion signatures of the digesting agent(s) in the cell lysates-or extracts over a given time period are measured. The magnitude and or rate of the digestion of these components are compared to a control cell lysate or tissue extract. Computational sorting of individual degradation rates are possible. For high density data analysis several informatics tools may be used including, but not limited to, hierarchical clustering algorithms, self organizing map node clusters, support vector machine, principle component analysis, k-n means, k-nearest neighbor (KNN), mantel tests, Euclidean geometry, Bayesian neural networks and the like. Auxiliary, supportive data may also be used to assist in data interpretation and classification including, but not limited to, clinical data, western blot data, gene expression data, peptide mass spectrometric data, metabolomic data, comparative genomic hybridization data, nucleotide polymorphisms, DNA methylation, extra-chromosomal DNA, microRNA and 2 dimensional gel electrophoresis.

In another aspect, the sample to be digested are not pre-immobilized but are captured by an affinity capture agents such as antibodies or aptamers located directly on the sensor in order to extract individual components from a test sample onto a biosensor. In another aspect, the immobilized bioentity is not affinity captured but obtained from a pre-purified preparation or extract. The magnitude or rate of digestion for the extracted substrate is measured using a known control digesting agent. A relative comparison between the test and control components can be obtained. In yet another aspect, the sample to be immobilized on the biosensor are subject to chromatography prior to immobilization or capture.

Using the techniques described above, changes in refractive index due to digestion or chemical cleavage of immobilized bioentities can be measured and recorded for various samples. In various aspects, it is desirable to score the difference of the change in refractive index to screen the cell population for a particular proteolytic phenotype or degradomic signature. Several statistical methods can be used to identify the characteristics of the differences between two different proteolytic signatures or degradomes. For example, algorithms are known in the art for combining and analyzing data from replicate screens derived from a plurality of samples. The techniques disclosed in U.S. published application nos. 2003/0017481 and 2004/0009495, which are incorporated by reference, can be used for data scoring and analysis.

The methods described above can be used to generate libraries of data that can be used as (1) a diagnostic or research tool (e.g., indicate disease state); (2) prognostic (e.g., indicate what is the patient outcome for a given therapy); and (3) therapeutic (e.g., what disease based digestion targets are good and likely candidates for therapeutic targets in a drug discovery platform). In one aspect, described herein are databases that represent a library of proteolytic signatures of biological samples for which the database is tangibly embodied on a computer-readable medium comprising one or more proteolytic signatures of the biological samples, wherein each proteolytic signature represents a difference in degradation (e.g., digestion) activity as measured by refractive index between a sample biological sample and a control biological sample. In another aspect, described herein are databases representing a library of a degradome of biological samples wherein the database is tangibly embodied on a computer-readable medium comprising one or more degradomes of biological samples, wherein each degradome represents a difference in degradation activity (e.g., digestion) as measured by refractive index between a sample biological sample and a control biological sample.

The methods, steps, systems, and system elements described above may be implemented using a computer system, such as the various embodiments of computer systems described below, to produce libraries of data. The methods, steps, systems, and system elements described above are not limited in their implementation to any specific computer system described herein, as many other different machines may be used. Such a computer system may include several known components and circuitry, including a processing unit (i.e., processor), a memory system, input and output devices and interfaces, transport circuitry (e.g., one or more busses), a video and audio data input/output (I/O) subsystem, special-purpose hardware, as well as other components and circuitry, as described below in more detail. Further, the computer system may be a multi-processor computer system or may include multiple computers connected over a computer network. The computer systems disclosed in U.S. published application no. 2004/0009495, which is incorporated by reference, can be used herein.

Classification of cellular phenotype, cellular origin, outcome prediction or response to drug therapy can be obtained through comparative degradomic signatures. Sets of digestive targets can be analyzed. Alternatively, complex mixtures of extracts or serum containing digestion agents can be analyzed. The fitted rate of digestion data or endpoint digestion data can be used for data measure. Sorting the degree to which these digestion elements in a collective degradomic signature(s) in a sample correlate to classification distinction of a sample can be done through pattern recognition, self-organizing maps; threshold based weighted voting schemes, support vector analysis and principal component analysis and artificial neural networks. For example, for complex data sets the data can be analyzed through neighborhood analysis, Pearson correlation routine, or Euclidean distance routine that comprises defining an idealized degradomic pattern of said digesting elements. Classifier models for the degradomic signature can be built from known control samples. In addition, training sets and leave-one-out cross validation schemes can be used to aid on the scoring of classification.

The methods described above allow for subjects to be screened and potentially characterized according to their ability to respond to a plurality of drugs. For instance, cells of a subject, e.g., cancer cells, can be removed and exposed to a plurality of putative therapeutic compounds, e.g., anti-cancer drugs, in a high throughput manner. These techniques can be used to optimize therapies for a particular subject. For instance, a particular anti-cancer therapy may be more effective against a particular cancer cell from a subject. This could be determined by analyzing the changes in the digestion profile for sets of immobilized bioentities on the biosensor caused by the cell in the presence of the compound. The compound can be a drug, a small organic molecule, an inorganic molecule, a putative pro-drug, a metabolite or a complex combination or admixture of the compounds mentioned. Additionally, this type of analysis can be used to identify subjects for less aggressive, more aggressive, and generally more tailored therapy to treat a disorder.

The methods described herein are also useful for determining the effect of multiple drugs or groups of drugs on a cellular degradomic phenotype. For instance it is possible to perform combined screens to identify a synergistic or other combined effect arising from combinations of drugs. For example, one set of drugs can induce a first conformational change, while another drug induces a second conformational change. When the two sets of drugs are combined they may act to achieve a collective phenotypic change, -exemplified by a third set of conformational changes. Additionally the methods could be used to assess complex multi-drug effects on cell types. For instance, some drugs when used in combination produce a combined toxic effect. It is possible to perform the screen to identify conformational changes associated with the toxic phenotype (e.g., ADME Tox studies).

Thus, the methods of the invention are useful for screening multiple compounds. For instance, the methods are useful for screening libraries of molecules, FDA approved drugs, and any other sets of compounds. In certain aspects, the methods are used to screen at least 20, 30, or 50 compounds. In some aspects, the methods are used to screen more than 96, 384, or 1536 compounds at a time.

In one aspect, the methods are useful for screening FDA approved drugs. An FDA approved drug is any drug that has been approved for use in humans by the FDA for any purpose. This is a particularly useful class of compounds to screen because it represents a set of compounds that are believed to be safe and therapeutic for at least one purpose. Thus, there is a high likelihood that these drugs will at least be safe and possibly be useful for other purposes. FDA approved drugs are also readily commercially available from a variety of sources.

A "library of molecules" as used herein is a series of molecules displayed such that the compounds can be identified in a screening assay. The library may be composed of molecules having common structural features that differ in the number or type of group attached to the main structure or may be completely random. Libraries are meant to include but are not limited to, for example, phage display libraries, peptides-on-plasmids libraries, polysome libraries, aptamer libraries, synthetic peptide libraries, synthetic small molecule libraries and chemical libraries. Methods for preparing libraries of molecules are well known in the art and many libraries are commercially available. Libraries of interest include synthetic organic combinatorial libraries. Libraries, such as, synthetic small molecule libraries and chemical libraries are possible. The libraries can also comprise cyclic carbon or heterocyclic structure and/or aromatic or polyaromatic structures substituted with one or more functional groups. Libraries of interest also include peptide libraries, randomized oligonucleotide libraries, and the like. Degenerate peptide libraries can be readily prepared in solution, in immobilized form as bacterial flagella peptide display libraries or-as phage display libraries. Peptide ligands can be selected from combinatorial libraries of peptides containing at least one amino acid. Libraries can be synthesized of peptoids and non-peptide synthetic moieties. Such libraries can further be synthesized which contain non-peptide synthetic moieties that are less subject to enzymatic degradation compared to their naturally-occurring counterparts.

Small molecule combinatorial libraries may also be generated. A combinatorial library of small organic compounds is a collection of closely related analogs that differ from each other in one or more points of diversity and are synthesized by organic techniques using multi-step processes. Combinatorial libraries include a vast number of small organic compounds. One type of combinatorial library is prepared by means of parallel synthesis methods to produce a compound array. A "compound array" as used herein is a collection of compounds identifiable by their spatial addresses in Cartesian coordinates and arranged such that each compound has a common molecular core and one or more variable structural diversity elements. The compounds in such a compound array are produced in parallel in separate reaction vessels, with each compound identified and tracked by its spatial address. Examples of parallel synthesis mixtures and parallel synthesis methods are provided in U.S. Pat. No. 5,712,171.

The proteolytic or degradomic profiles obtained by the biosensor can be used either as a stand alone informational tool or may be aided by other biological information. The other biological information can include, but is not limited to, genomic single nucleotide polymorphisms, gene expression data, chromosomal aberration data such as deletions or translocations within chromosomal structure, cellular structure analysis via fluorescence microscopy, comparative genomic hybridization (i.e. CGH), metabolomic profiles by NMR or mass spectroscopy, peptidomic profiles by mass spectroscopy, haplotype mapping, mitochondrial phenotypes, chemical genomic profiling, ribotyping and the like.

VIII. Kits-

In one aspect, described herein are kits comprising (1) a biosensor that can detect a change in refractive index, wherein one or more bioentities are immobilized on the surface of the biosensor, and (2) one or more agents that can induce a degradation (e.g., digestion) change of the immobilized bioentity on the biosensor. Depending upon the assay to be performed, it is possible to immobilize one or more bioentities on the surface of the biosensor. In one aspect, a plurality of the same bioentity can be immobilized on the surface of the biosensor to screen a host of drugs or small molecules. In another aspect, a plurality of different bioentities can be immobilized on the surface of the biosensor to analyze the presence of a target compound in a sample. In one aspect, the biosensor comprises a microarray or a microplate.

Any of the agents described above that can induce a conformational change (e.g., a degrading agent, a denaturing agent, a degrading catalyst, a modifying agent, a probe, or any combination thereof) can be part of the kit and present as solutions in vials. The selection and concentration of the agents can be optimized based on the particular assay to be performed. The selection of the solvent used to prepare agent solutions can also be selected to achieve particular bulk refractive index levels. It is contemplated that once the biosensor is has been exposed to the particular agent and target molecule, the biosensor can be inserted into a device that can detect a change in refractive index to produce a refractive index signature or pattern that can be compared to patterns or signatures associated with known conformational changes of the bioentity immobilized on the biosensor.

EXAMPLES

The following examples are put forth so as to provide those of ordinary skill in the art with a complete disclosure and description of how the materials, articles, and methods described and claimed herein are made and evaluated, and are intended to be purely exemplary and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions.

Example 1

Degradation Assays

In this method, the rate or extent of chemical (e.g. CNBr) or enzymatic (e.g. proteases; Trypsin, chymotrypsin or nucleases; DNAse I) degradation was used to assess the interaction between two or more molecules. A target protein human serum albumin (H.S.A.) was immobilized on an Epic™ System biosensor. In a microplate format, one well on the biosensor was used to measure the rate of degradation of the target in the absence of the partner "binder" molecule as a control. The assay can be run as inter-well or as intra-well assay (with printed protein or peptide controls that normalize digestion rates or with blocking agents on one portion of the sensor that enable in well detection of the digestion process). The rate of degradation was measured as a loss of mass or decrease in refractive index on the surface. Conformational changes in/on the surface of the immobilized target molecule translate into either enhancement or reduction in the rate of degradation.

In FIG. 1, each trace represents the average of a single time trace for trypsin digestion of human serum albumin on the biosensor surface. As the trypsin digests the protein off the surface of the biosensor there is a corresponding decrease in mass on the surface. The traces are corrected relative to other wells that contained only PEG amine immobilized (polyethylene glycol with primary amines) and gave no digestion signal. The data indicates several properties. First that digestion rates that are protein specific can be detected with the biosensor. Secondly, that the addition of a known small molecular weight drug (warfarin=308 Dalton) causes a detectable reduction in trypsin digestion. When this same experiment was run for a generic protein such as rabbit IgG plus warfarin or even a standard fluorescent substrate like BZIP plus warfarin (Molecular Probes Inc./Invitrogen Inc.) no such reduction in digestion rate was observed. Hence, the reduction in digestion rate appears to be H.S.A. specific and directly due-to binding by the warfarin.

Example 2

Catalytic Digestion

Figure 2:
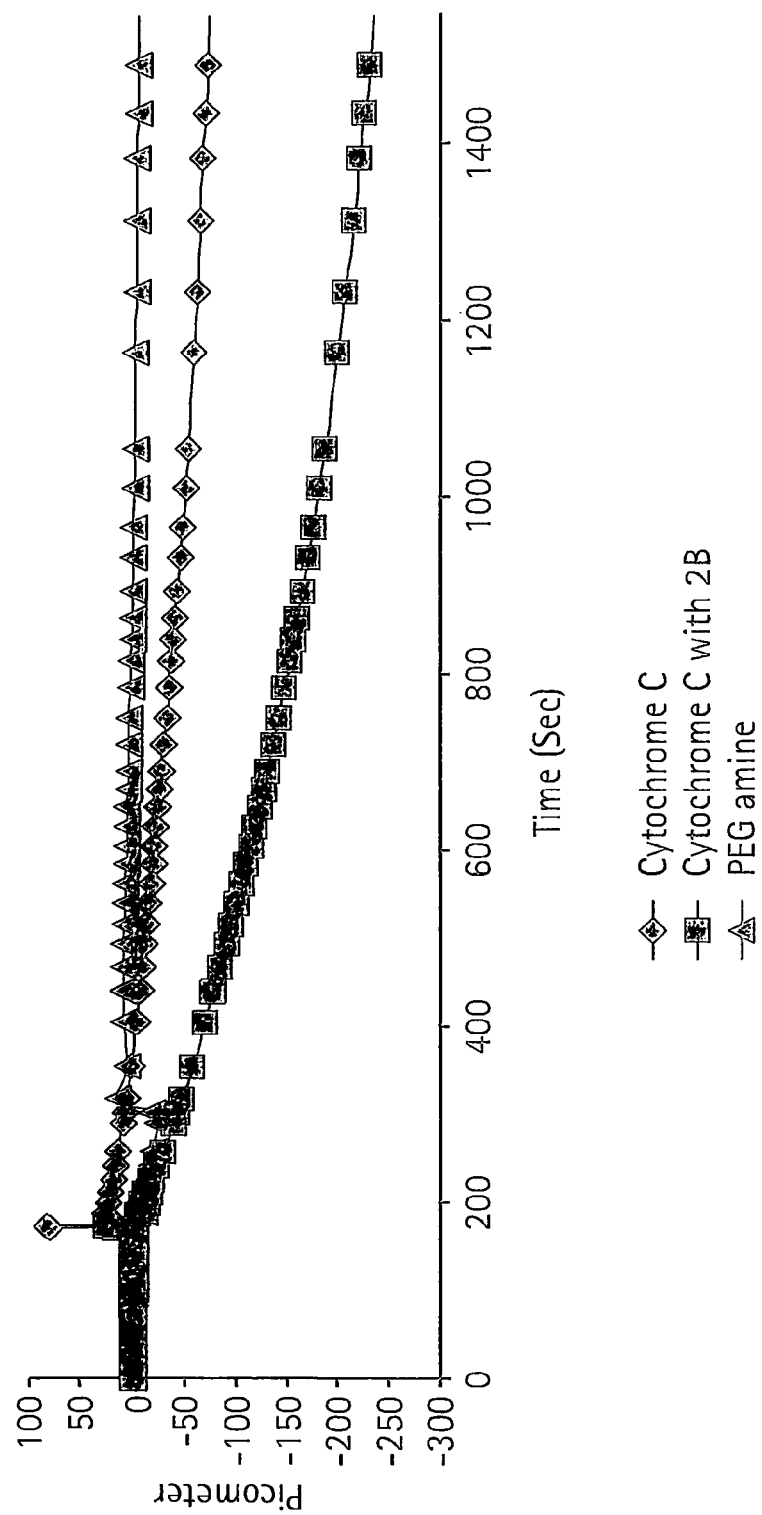
FIG. 2 shows the catalytic proteolysis of cytochrome C.

In order to prove that catalytic digestion can be performed on a biosensor (Epic™ System), copper (II) tetra-(4-carboxyphenyl)porphyrin was synthesized using the techniques disclosed in Groves et al., *J. Am. Chem. Soc.*, 2004, 126:12833-12842 and tested as a degrading catalyst. On the Epic™ System, equine cytochrome C was chemically immobilized onto the EMA surface. The comparative trypsin digestion on the Epic™ system was measured. Referring to FIG. 2, the black arrow points to the digestion trace for the copper II porphyrin and demonstrates a significant enhancement of digestion. In these assays, 15 units of trypsin were used in each well. No titration was done for the enzyme, the cytochrome protein or the copper II porphyrin.

Example 3

Conformational Assays

Figure 3:
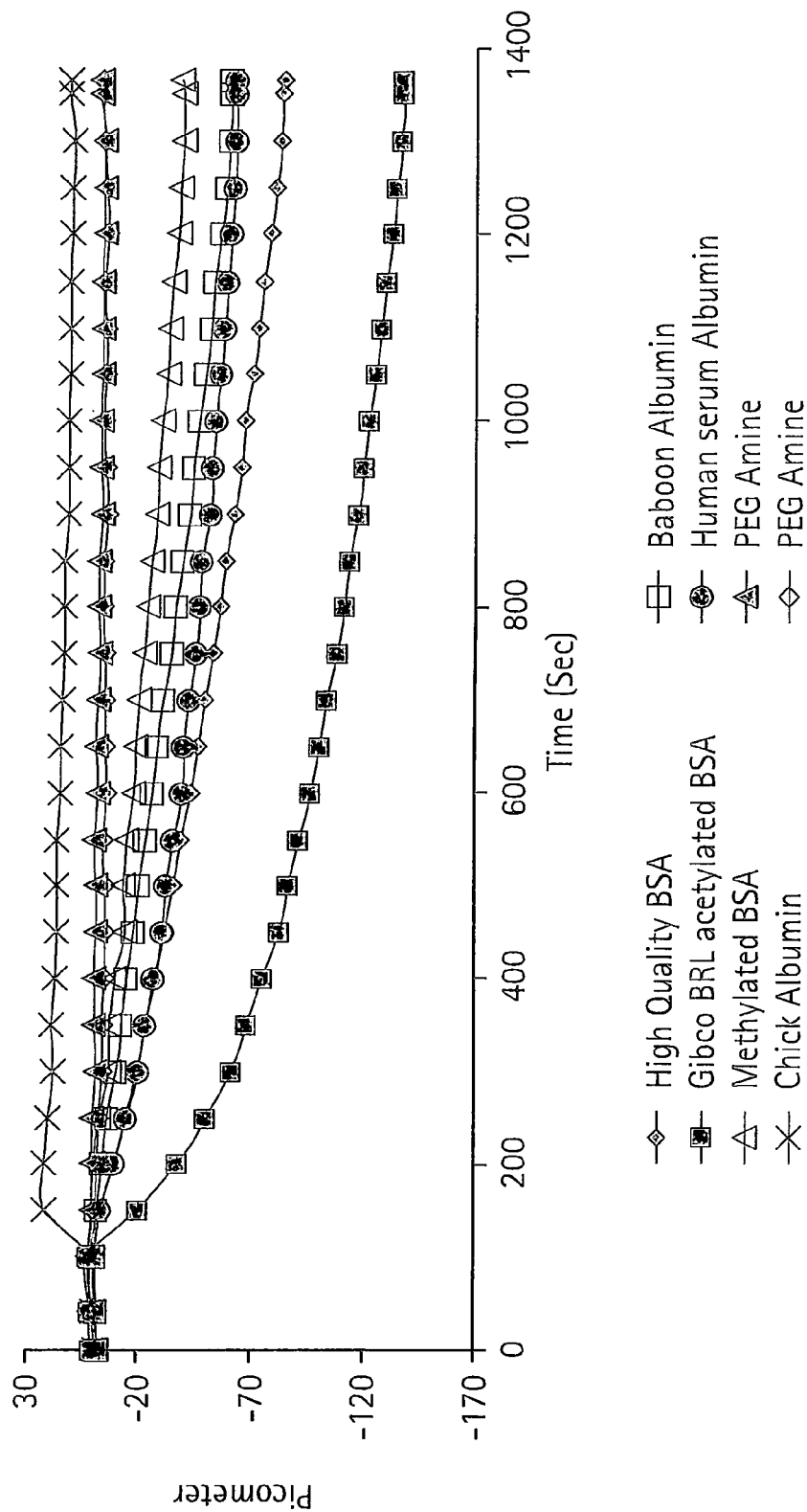
FIG. 3 shows the digestion of various blood serum albumins with trypsin.
Figure 4:
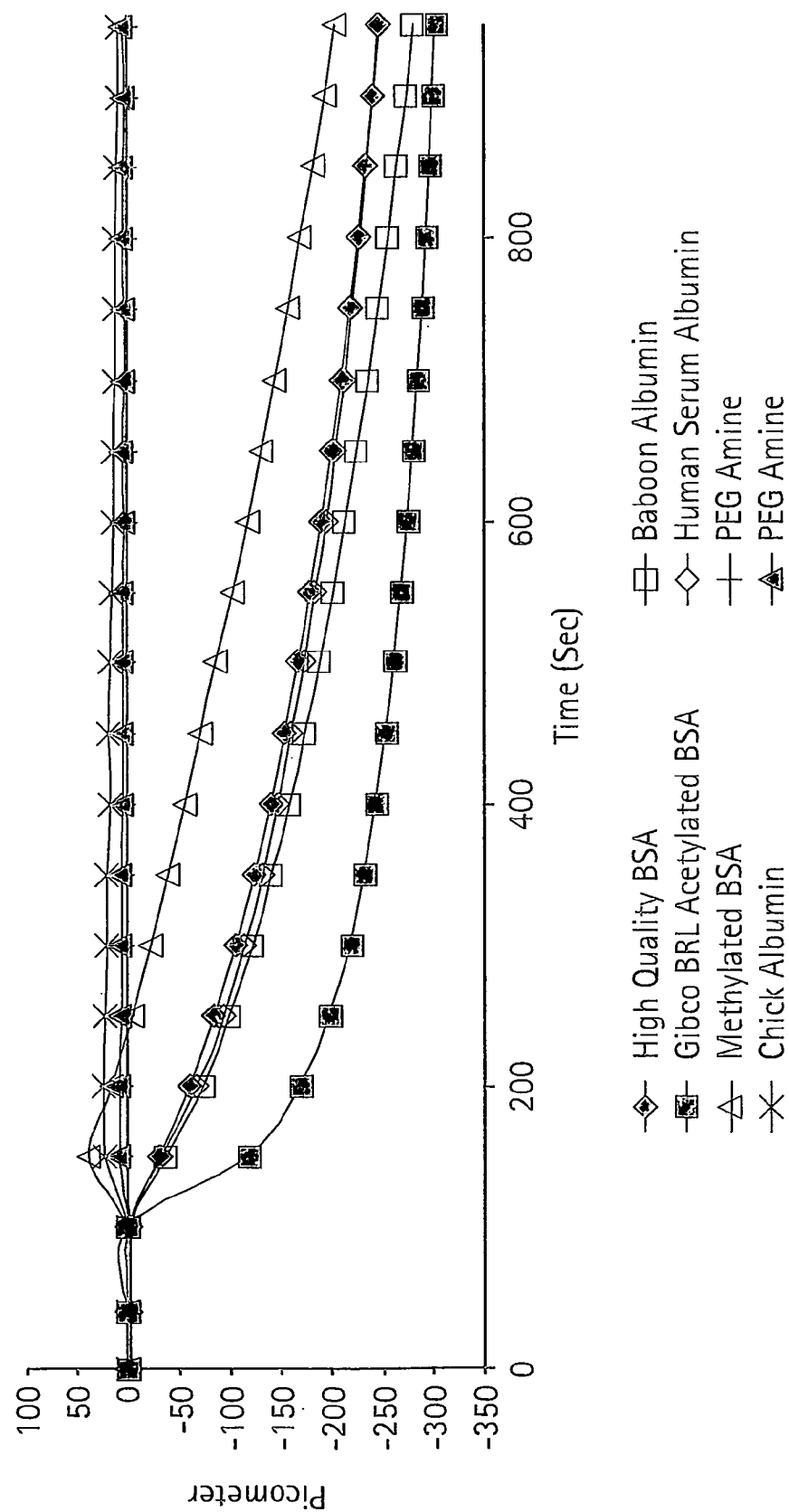
FIG. 4 shows the digestion of various blood serum albumins with chymotrypsin.

In this assay, it was determined whether or not a label-independent detection assay can distinguish between different albumins by digestion with either trypsin or chymotrypsin on the Epic™ system. In this assay, digestion of BSA, acetylated BSA, methylated BSA, human serum albumin, baboon albumin and chicken albumin was examined, and the results are depicted in FIGS. 3 and 4. The acetylated BSA gave a dramatic enhanced digestion profile relative to normal BSA, while methylated BSA gave a dramatic reduction in digestion rates. With trypsin digestion (FIG. 3), the acetylated BSA may be more denatured than the other BSA. Human, baboon and normal BSA yielded closely similar digestions but not identical. In short, the digestion profiles were unique to several different protein sequences and chemical modifications. Chymotrypsin rates (FIG. 4) were not equal to trypsin digestion rates. This is not surprising since it is known that the two enzymes possess very different catalytic digestion properties. These profiles were well maintained across many columns suggesting both reproducibility and that the profiles are real and not erroneous. These digestion signatures are informative in that they can be used to correlate function with structural integrity.

Example 4

Conformational Mode Locking on a Biosensor

Figure 5:
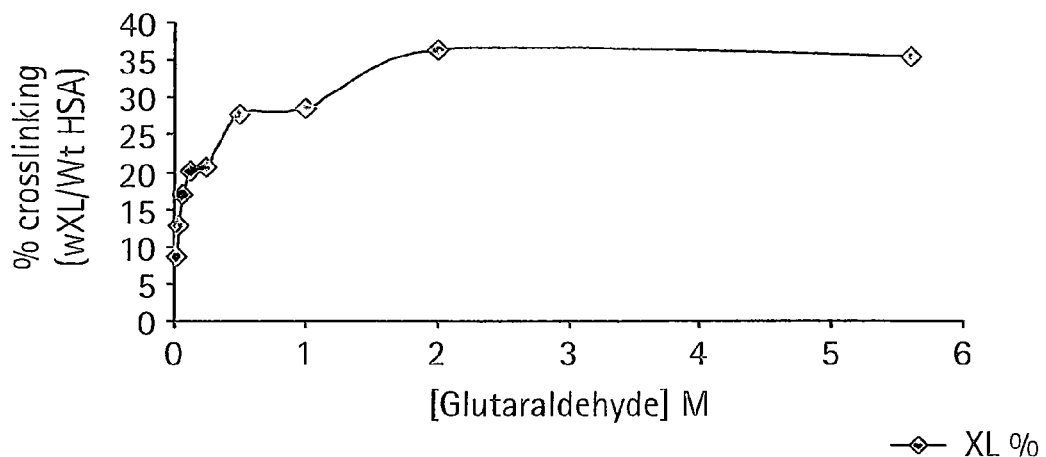
FIG. 5 shows the percent of crosslinking of H.S.A. as a function of glutaraldehyde concentration.

The use of covalent chemical crosslinking as a way of assaying conformational states or transitions of bioentities was investigated. H.S.A. was immobilized on an Epic™ sensor. The protein was crosslinked with glutaraldehyde under a variety of conditions (FIG. 5). Glutaraldehyde is a small molecular weight organic chemical (100 Dalton). It can undergo a variety of chemical crosslinking events with either itself or several amino acids. For this study, 10% glutaraldehyde in 0.1 M phosphate pH 7 was used. This was done to avoid the possibility of polymeric glut from forming. The amount of protein immobilized on the surface was also measured as well as the amount of chemical crosslinking and trypsin digestion. It was shown that proteolytic digestion was dramatically inhibited/attenuated by chemical crosslinking. This effect was expected since crosslinking should affix the protein to the surface and render mass loss incapable. This finding should permit the ability to immobilize affinity capture molecules like antibodies and streptavidin and after crosslinking prevent their digestion. These crosslinked capture structures can then be used to specifically orient their antigens for antigen specific digestion.

Example 5

Percent Crosslinking of a Protein

Figure 6:
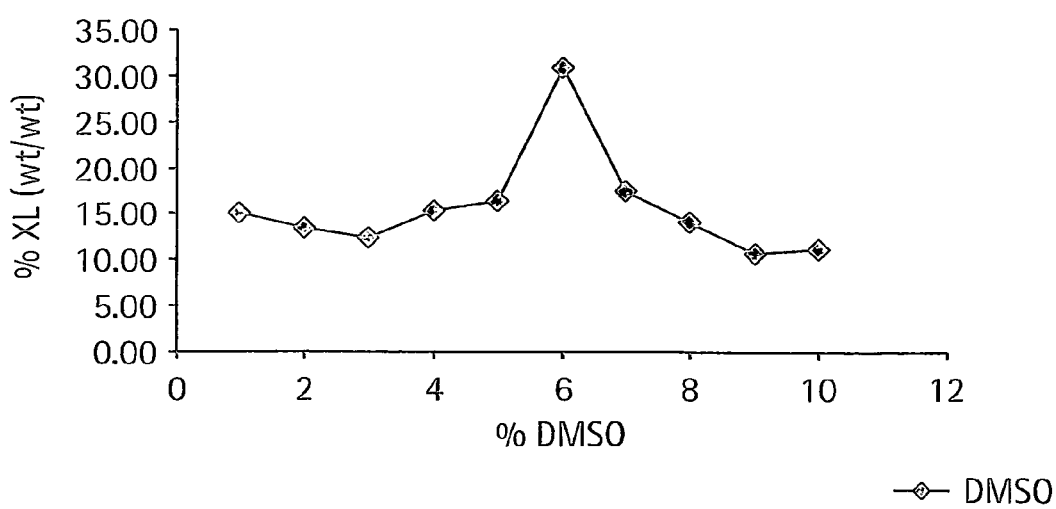
FIG. 6 shows the effect of DMSO has when crosslinking H.S.A. with glutaraldehyde.
Figure 7:
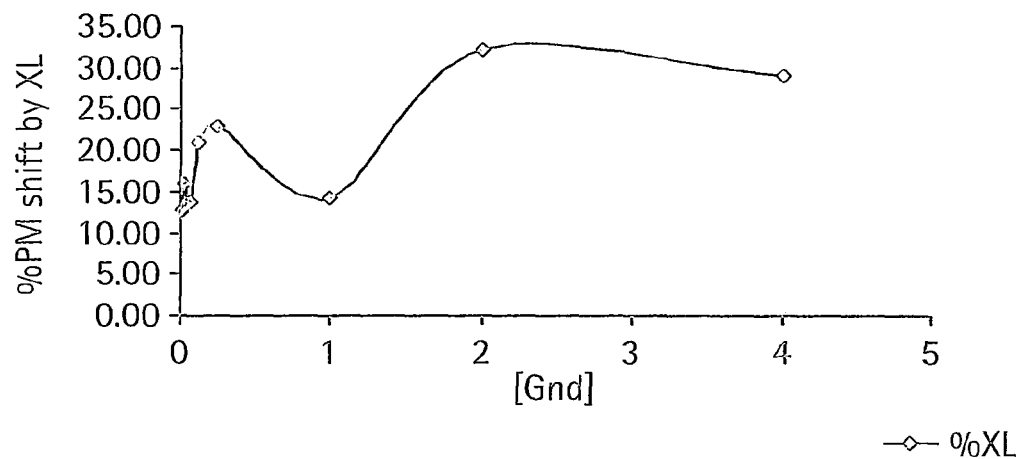
FIG. 7 shows the effect of guanidine HCl on crosslinking H.S.A. with glutaraldehyde.
Figure 8:
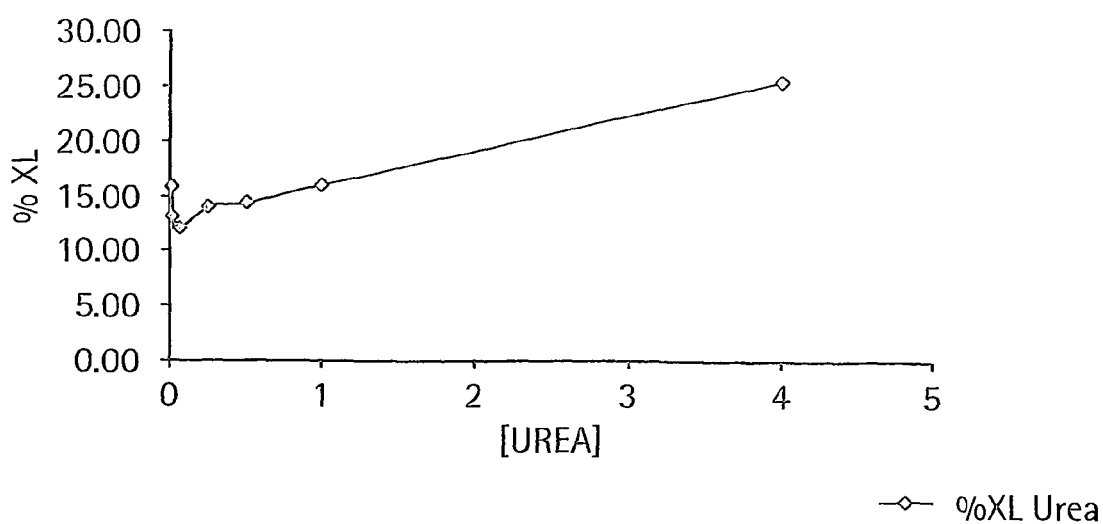
FIG. 8 shows the effect of urea on crosslinking H.S.A. with glutaraldehyde.
Figure 9:
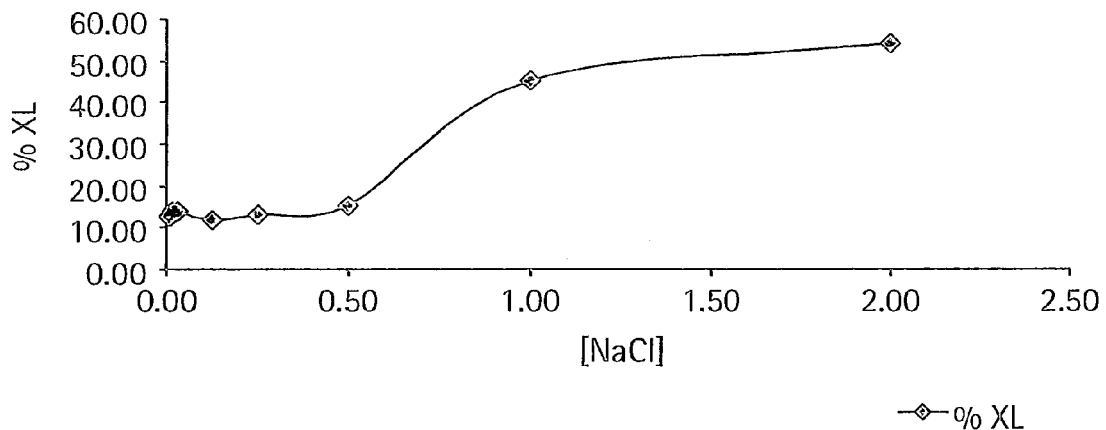
FIG. 9 shows the effect of NaCl on crosslinking H.S.A. with glutaraldehyde.
Figure 10:
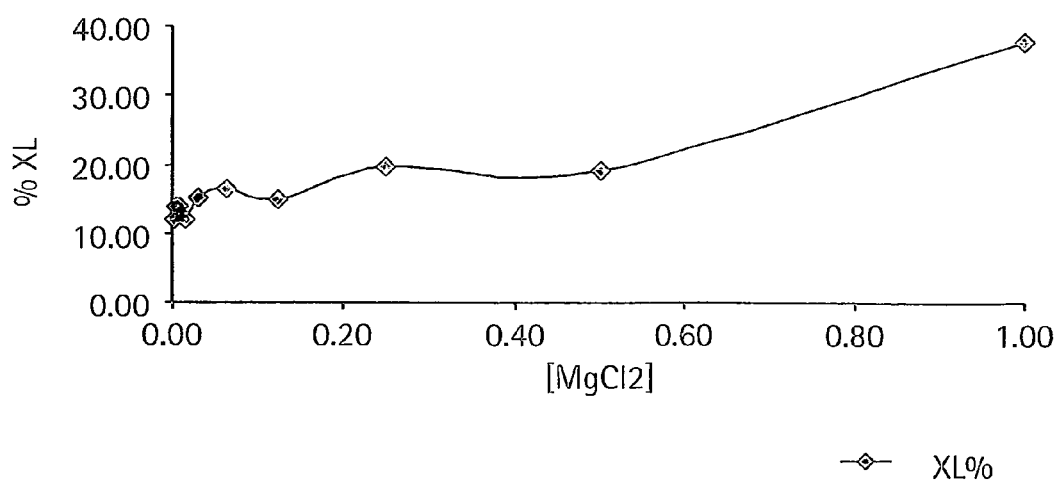
FIG. 10 shows the effect of $MgCl_2$ on crosslinking H.S.A. with glutaraldehyde.

The fractional amount of chemical crosslinking was measured by taking the ratio of added crosslinker attached to the protein relative to amount of initial protein on the sensor. Initially, protein is immobilized and washed on the Epic™ sensor and then measured for amount of immobilized protein. The protein is exposed to glutaraldehyde with a specified solution condition. The mass change that resulted from crosslinking is recorded again on the Epic™ system. The ratio of picometer change by crosslinker (due to mass increase) to mass of protein immobilized (as measured by initial change in picometer due to protein immobilization) is referred to as the fractional amount of crosslinking (% XL or % crosslinking), which is depicted in FIG. 6. This mass change by chemical crosslinking provides a "snap shot" of the conformational state accessible to cross linker. A number of conformational perturbation effects were demonstrated. FIG. 6 shows the effect of DMSO has when crosslinking H.S.A. with glutaraldehyde.

As a protein or bioentity is denatured it should unfold and thereby increase the number of available sites for crosslinking. This general effect was in fact measured for a number of known denaturants. Urea, guanidine HCL (Gnd), NaCl, and MgCl for the most part showed increasing percent crosslinking as the concentration of denaturing agent increased. This is depicted in FIGS. 7-10.

Example 6

Surrogate Binding

In this assay, the detection of macromolecular events whose mass changes are below detection due to sparingly low refractive index changes on a biosensor are consequentially assayed through surrogate associations that are then detectable by refractive index changes (i.e., any event (ion or not) which conveys a signature through association and is assayable on a biosensor).

Calmodulin (CAM) is a classic calcium binding protein. It binds four calcium ions per protein. At saturation, four ligands at a mass of 40 Daltons equals 160 Dalton is produced. This mass is expected to be below normal direct bind detection. However, upon calcium binding CAM undergoes a dramatic conformational transition. The physical changes by CAM play a crucial role in the functioning of this molecule in vivo. Fluorescent probes that sense hydrophobic transitions have been used for more than a decade. Two fluorescent hydrophobic probes that have been used routinely are 8-anilinonaphthalene-6-sulfonic acid (316.38 Da, Sigma A3125 ANS) and 4,4'-dianilino-1,1'-binaphthyl-5,5'-disulfonic acid, dipotassium salt (672.87 Da, Sigma D4162, bis-ANS). These probes have been used to demonstrate a calcium specific conformational change in calmodulin. Calmodulin was chosen as the model system for the concept of surrogate direct binding because the binding of calcium to this protein should not be readily detectable on a biosensor (4×40 Dalton for calcium=160 Da). Hence, only indirect conformational changes of calmodulin can be assayed.

Figure 11A:
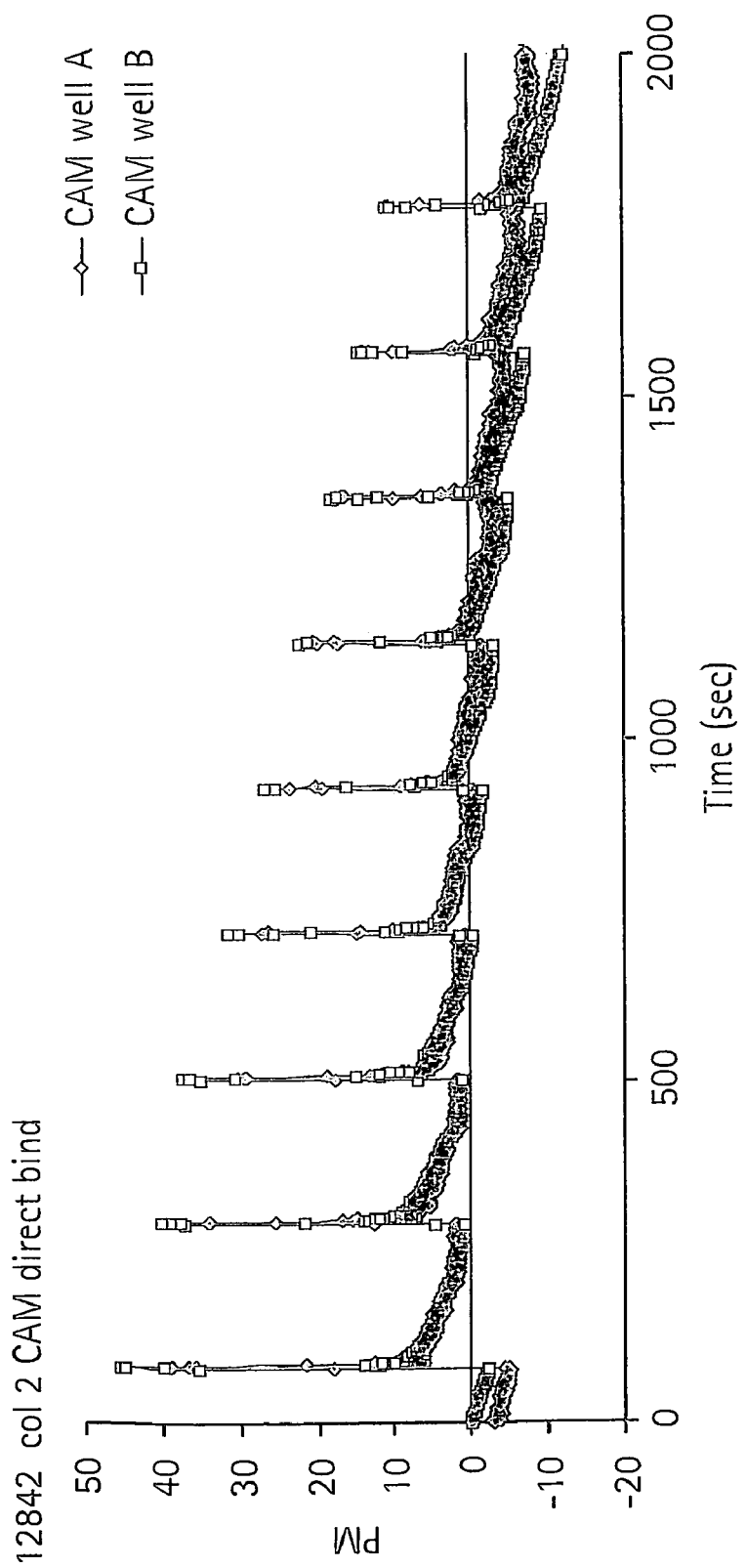
FIG. 11 shows the direct binding of calcium ions with CAM, where little to no binding data was observed.
Figure 11B:
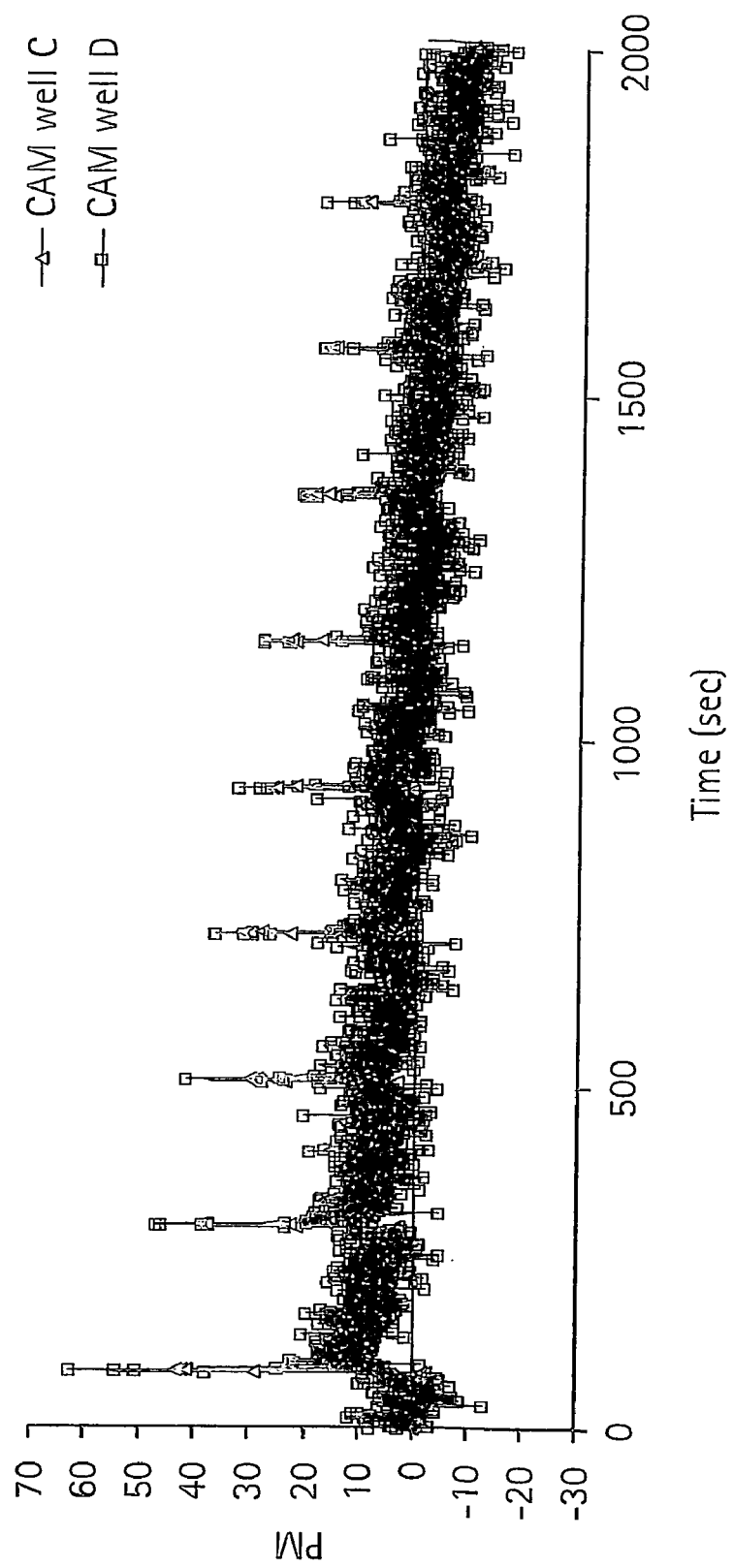
Figure 12A:
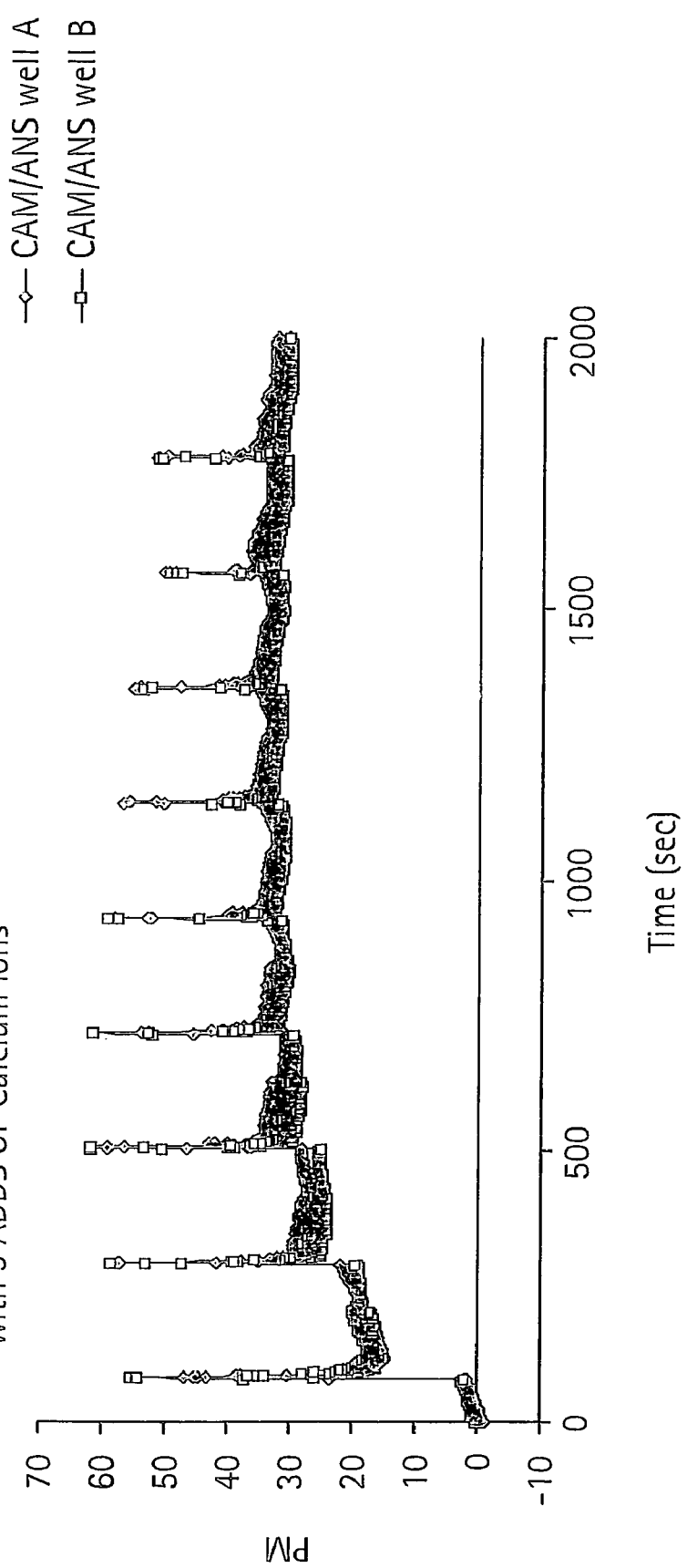
FIG. 12 shows the direct binding of calcium ions with CAM in the presence of ANS, where binding data was observed.
Figure 12B:
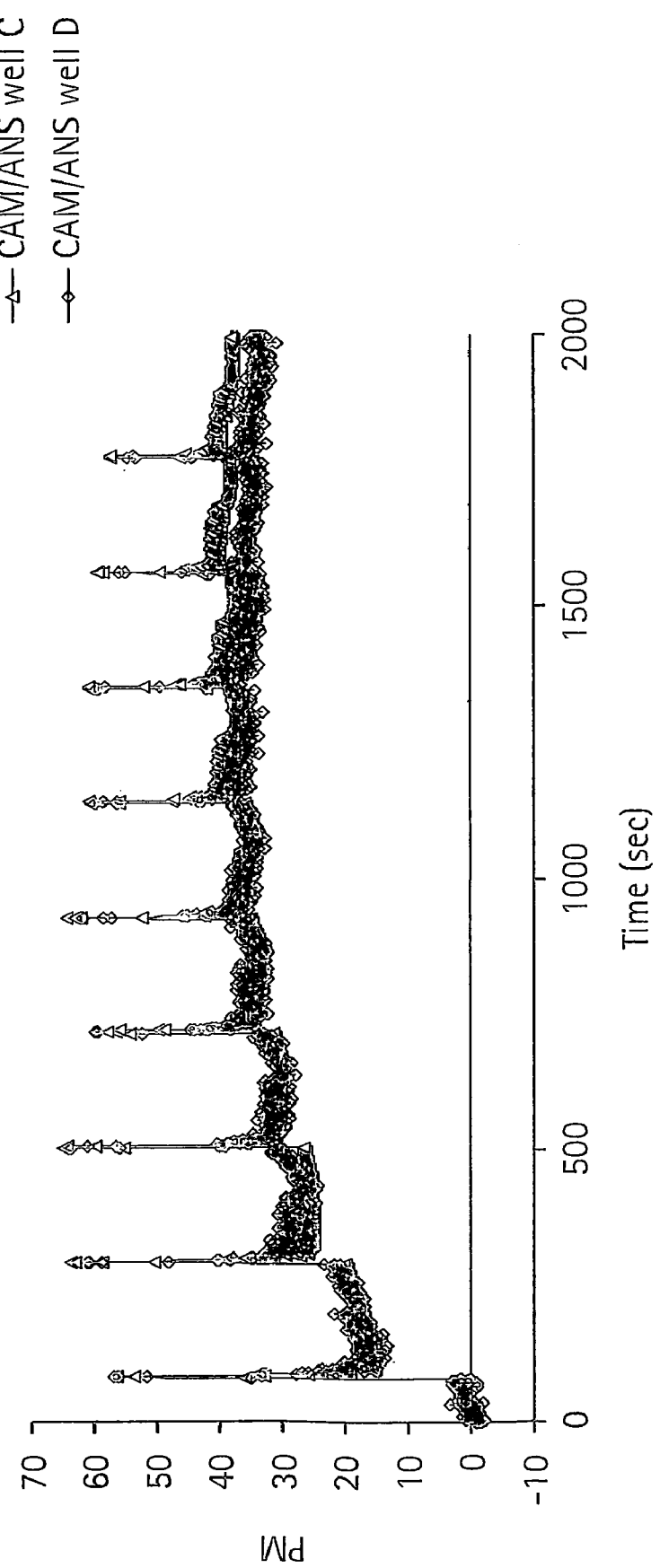
Figure 12D:
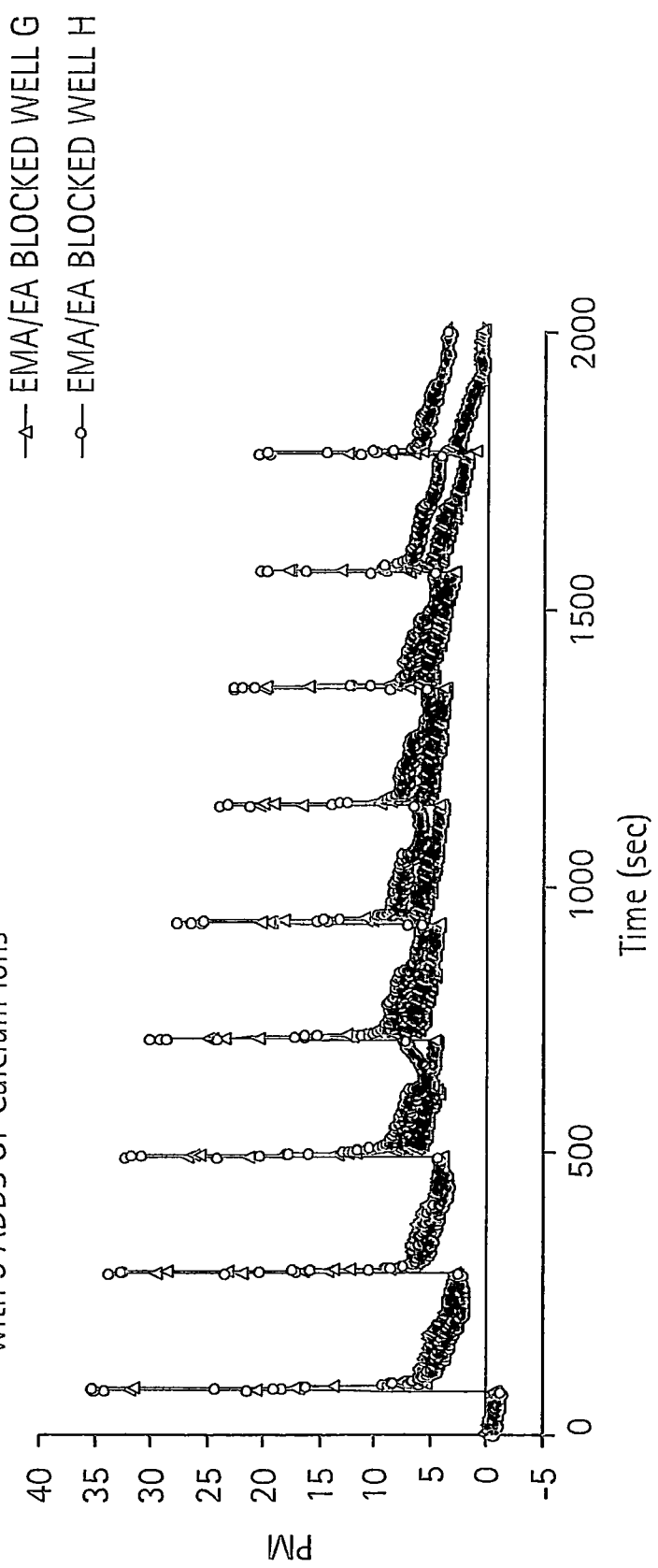

CAM was ordered through Upstate cell signaling solutions (Cat #14-368). In the following experiment CAM was immobilized on the Epic™ biosensor in wells A-F while wells G and H contained ethanolamine blocked EMA polymer only coated sensors (for columns 2 and 4). Column 2 contained only CAM in 1×PBS while column 4 contained a solution of 100 µM ANS (8-anilinonaphthalene-6-sulfonic acid (316.38 Da, Sigma A3125 ANS=hydrophobic probe). To each column, nine consecutive additions of 200 µM calcium chloride in 1×PBS were added. The additions are demarcated by spikes due to mixing (FIGS. 11 and 12). The biosensor data revealed a binding event only in the column 4 assay that contained the hydrophobic probe ANS, while the direct bind assay for calcium additions gave no binding data relative to the blocked wells (G&H) (FIGS. 13 and 14). As can be seen from FIGS. 11-14, the net difference from the initial starting point for direct bind detection is not useful for observing the calcium interacting with the calmodulin on the biosensor. Yet, when a hydrophobic probe is employed (a surrogate direct bind probe), a calcium modulation interaction is detected.

Example 7

Heme Insertion in Apo-Proteins

Heme proteins are evolutionarily designed to specifically retain the heme moiety. Hemin or heme is a 20 carbon macrocyclic compound of 651.96 Dalton. This organometalic molecule, which contains and iron atom, is capable of facilitating oxygen transport in blood. Insertion of heme into the heme pocket of a heme-protein is known to be stable and relatively irreversible. The removal of heme from human alpha and beta hemoglobin results in a dramatic conformational change in the apoprotein structure (Waks et al., JBC. 1973. 248:6462-6470). That is, roughly 50% of the alpha helical structure of the protein is lost. This is not surprising since the alpha and beta chain subunits of human hemoglobin have 18 and 20 atomic contacts with the heme molecule (Fermi and Perutz, Haemoglobin & Myoglobin, Phillips, D. C and Richards, F. M., Eds. Clarendon Press, Oxford, 1981). For these reasons, this molecular system was chosen as a model to examine the effects of conformational changes induced by binding of a small organic molecule.

Heme Removal

The apoglobin form of the human hemoglobin and horse myoglobin were made using the acid-acetone methods of Rossi-Fanelli (BBA. 30:608-615. 1958) and Ascoli et al., Methods in Enzymology, 76:72-87, 1981). The extent of heme removal was confirmed spectrophotometrically. This process generated human apohemoglobin (an alpha beta dimmer) and horse apomyoglobin.

Immobilization of Heme and Apoheme Proteins

The heme containing and apoheme proteins were immobilized on an Epic™-biosensor. The extent of protein immobilization was determined by comparison of picometer changes on the waveguide before and after immobilization (wash of excess protein was also done). The graph in FIG. 15 demonstrates that the proteins used in this study were efficiently immobilized on the biosensor and gave between 600 to 1,400 picometers of protein specific shift.

Heme Insertion

Figure 16:
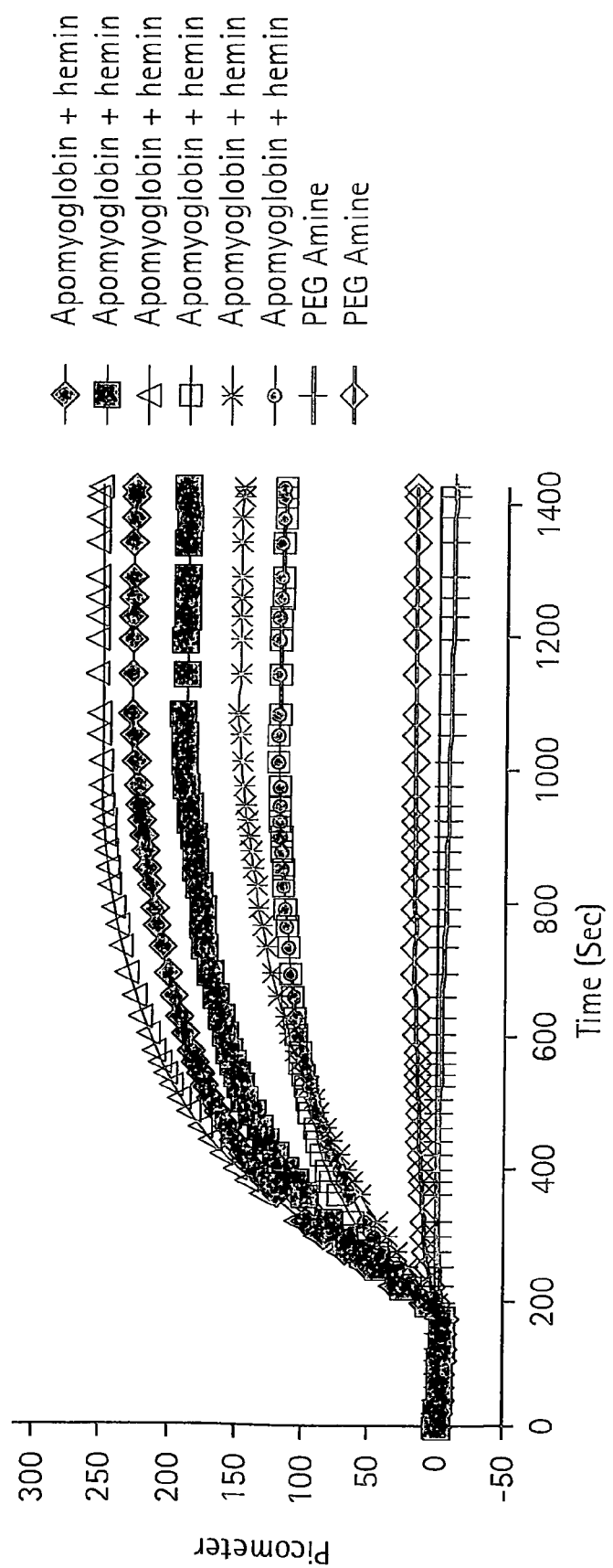
FIG. 16 shows traces for heme insertion into apomyoglobin.
Figure 17:
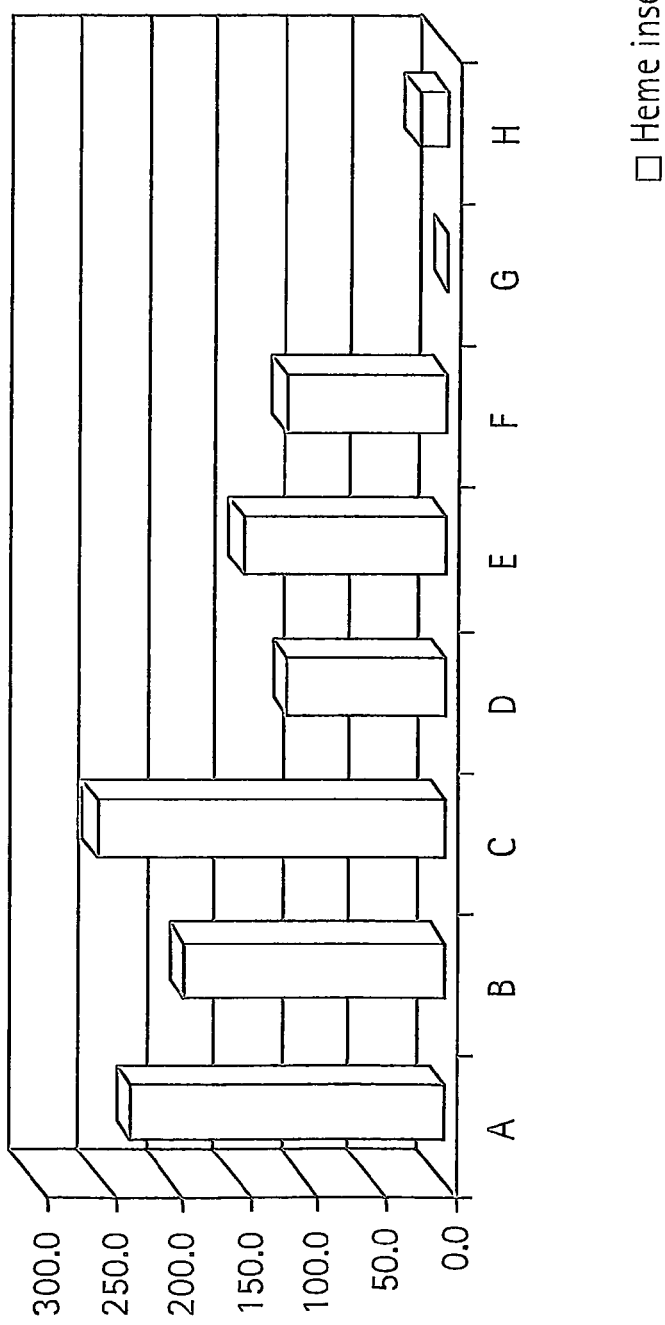
FIG. 17 is a bar graph showing heme insertion into apomyoglobin.

Selected apoprotein wells on the LID microplates were exposed to 2 µM hemin and then washed after 30 minutes. An example of heme insertion into apomyoglobin is shown in FIGS. 16 and 17. The range of 116 to 220 pm shift occurred for the heme insertion into apomyoglobin. Under these experimental conditions, the heme moiety will remain inside the heme pocket of the heme protein as essentially irreversible. The wells that underwent heme insertion were washed and replaced with 1×PBS buffer.

Comparative Digestion on Epic™ System.

The heme inserted wells as well as the apoprotein and myoglobin wells were digested using 15 units of trypsin in 1× PBS. The digestion process was allowed to proceed for approximately 23 minutes with continuous monitoring of refractive index changes on the LID system. The hierarchy of digestion followed the following order; myoglobin (−250 pm)<apomyoglobin with heme (−350 pm)<apomyoglobin (−500 pm) (FIGS. 18 and 19). Apomyoglobin gave the highest degree of digestion, suggesting that many of its cleavable sites were accessible to trypsin. The data also suggests that insertion of the 652 Dalton molecule into the heme free protein resulted in a shielding of residues from protolytic attack and thereby causing a 140 picometer reduction in digestion. The difference between the native myoglobin and the heme inserted apomyoglobin may be a result of slight denaturation effects that were introduced in the preparation of the apomyoglobin protein. This heme insertion study suggested that digestion assays on the Epic™ system can be used as an indirect means of assaying small molecular weight binding events into a large complex bioentities.

Example 8

Digestion Inhibition Assays

In this type of assay, the digestion signal can be used as a means for screening large compound libraries for modulators of digestion (i.e. inhibitors or enhancers). The digestion inhibitors could be directed against-any lytic agent including but not limited to peptidases (as in the Caspase assay), proteases, nucleases, glucuronidase, glucosidase, lipases and the like. The assay is capable of detecting small molecule inhibitors of digestion of any molecular weight size. The data shows that the addition of trypsin inhibitor causes a significant and measurable reduction in the digestion of human serum albumin. The extent to which an inhibitor can prevent digestion is assayed. In FIG. 20, it can also be seen that the digestion is effected by chemical modification of an immobilized bioentity. The bar in FIG. 20, labeled 2,3-butanedione represents the net tryptic digestion of H.S.A. after a 5 minute treatment of 2,3-butanedione. The chemical 2,3-butanedione is an effective chemical modifier of amino acids such as lysine or arginine and is known in the art as an effective inhibitor of trypsin digestion via target modification.

Throughout this application, various publications are referenced. The disclosures of these publications in their entireties are hereby incorporated by reference into this application in order to more fully describe the compounds, compositions and methods described herein.

Various modifications and variations can be made to the materials, methods, and articles described herein. Other aspects of the materials, methods, and articles described herein will be apparent from consideration of the specification and practice of the materials, methods, and articles disclosed herein. It is intended that the specification and examples be considered as exemplary.

REFERENCES

1. Groves et al. "Catalytic unfolding and proteolysis of cytochrome c induced by synthetic binding agents" *J. Am. Chem. Soc.* (2004) 126:12833-12842.
2. Park, C. and Marqusee, S., "Pulse proteolysis: A simple method for quantitative determination of a protein stability and ligand binding" *Nature Methods* (March 2005), Vol. 2., No. 3., 207-212.
3. Chah et al., "Gold nanoparticles as colorimetric sensor for protein conformational changes" *Chem. & Biol.* (2005) Vol. 12, 323-328,
4. Moazed et al. "Specific protection of 16 S rRNA by translational initiation factors" *J Mol Biol.* (Apr. 28, 1995), 248(2), 207-210.
5. Shelton, C. J. et al. "Enymatic and chemical footprinting of anthracycline antibiotics and related saccharide side chains" *Biochem.*, (1996), 35 (24): 7974-82
6. Jones et al., "Screening protein refolding using surface plasmon resonance" *Proteomics* (2004), 4, 1007-1013.
7. Gestwicki et. al., "Using receptor conformational change to detect low molecular weight analytes by surface plasmon resonance" *Anal. Chem.*, (2001), 73: 5732-5737.
8. Juarez-Gonzalez V R et al., "Directed evolution, phage display and combination of evolved mutants: a strategy to recover the neutralization properties of the scFv version of BCF2 α neutralizing monoclonal antibody specific to scorpion toxin Cn2" *J Mol Biol.* (Mar. 11, 2005);346(5):1287-97. Epub) (Jan. 16, 2005).
9. Yamaguchi et al., "Measuring adsorption of a hydrophobic probe with a surface plasmon resonance sensor to monitor conformational changes in immobilized proteins," *Biotechnol. Prog.*, (2003), 19, 1348-1354.
10. Myers et al. "Denaturant m values and heat capacity changes: relation to changes in accessible surface areas of protein unfolding" *Protein Science* (1995), 4:2138-2148.
11. Waldron et al. "Stabilization of proteins by ligand binding: application to drug screening and determination of unfolding energetics" *Biochem.* (2003), 42, 5058-6064.
12. Sota et al. "Detection of conformational changes in an immobilized protein using surface plasmon resonance" *Anal. Chem.* (1998), 70, 2019-2024.
13. Chah et al. "Denaturation and renaturation of self-assembled yeast iso-1-cytochrome c on Au" *Anal. Chem.* (2004), 76, 2112-2117.
14. Raitman et al. "Integration of polyaniline/poly(acrylic acid) films and redox enzymes on electrode supports: an in situ electrochemical/surface plasmon resonance study of the bioelectrocatalyzed oxidation of glucose or lactate in the integrated bioelectrocatalytic systems" *J. Am. Chem. Soc.*, (2002) 124, 6487-6496.
15. O'Brien, P. and Herschlag, D., "Catalytic promiscuity and the evolution of new enzymic activities" *Chemistry & Biology*, (1999) 6:R91-R105.
16. Overall et al., "Protease degradomics: mass spectrometry discovery of protease substrates and the CLIP-CHIP, a dedicated DNA micoarray of all human proteases and inhibitors" *Biol. Chem.*, (2004), Vol. 385, pp 493-504.
17. Lee et al., "Regulation of muscle protein degradation: coordinated control of apoptotic and ubiquitin-proteasome systems by phosphatidylinositol 3 Kinase" *J. Am. Soc. of Nephrol.*, (2004), 15,1537-1545.
18. Cal et al., "Polyserase-I, a human polyprotease with the ability to generate independent serine protease domains from a single translation product" *PNAS*, (2003), Vol. 100, No. 16, 9185-9190.
19. Overall, "Dilating the degradome: matrix metalloproteinase 2 (MMP-2) cuts to the heart of the matter," *Biochem. J.* (2004), 383, e5-e7.
20. U.S. Pat. No. 6,576,430
21. U.S. Pat. No. 6,569,628
22. U.S. Pat. No. 6,503,721
23. U.S. Pat. No. 6,331,392
24. U.S. Pat. No. 5,585,277
25. U.S. Pat. No. 5,679,582
26. U.S. Published Application No. 20040191765A1
27. U.S. Published Application No. 20040009495A1
28. U.S. Published Application No. 20030017481A1
29. U.S. Published Application No. 20020055123A1
30. U.S. Published Application No. 20020031778A1
31. U.S. Published Application No. 20020064793A1

What is claimed is:

1. A method for identifying the ability of a binding molecule to inhibit or enhance protein degradation, comprising:
   a. immobilizing the protein on each of a separated first surface and second surface of a biosensor that can detect a change in the surface refractive index;
   b. binding a binding molecule to the protein immobilized on the first surface of the biosensor but not to the protein immobilized on the second surface of the biosensor;
   c. exposing the immobilized protein to one or more degrading agents such that the immobilized protein on the first surface and second surface of the biosensor reacts with the degrading agent;
   d. measuring the first surface refractive index of the immobilized protein on the first surface and the second surface refractive index of the immobilized protein on the second surface of the biosensor; and
   e. comparing the first surface refractive index and the second surface refractive index, wherein (1) when the second surface refractive index is less than the first surface refractive index, the binding molecule inhibits degradation of the protein, and (2) when the second surface refractive index is greater than the first surface refractive index, the binding molecule enhances degradation of the protein.

2. The method of claim 1, wherein the binding molecule is a small molecule selected from the group consisting of a pharmaceutical drug, a metabolite, a supramolecular assembly, a nanoparticle, a polymer, and a bioentity having a molecular weight less than 300 Da.

3. The method of claim 1, wherein the biosensor comprises a glass substrate with a layer of gold deposited on the surface of the substrate, a hafnium oxide-coated glass surface, a grating-coupled biosensor, a Fabry Perot cavity sensor, a zero-mode waveguide, a fluorescent enhanced SPR sensor, a cantilever biosensor, an impedance-based electrode detection, or a high Q whispering mode gallery cavity resonator.

4. The method of claim 1, wherein the degrading agent comprises a protease.

5. The method of claim 4, wherein the protease comprises a natural or synthetic protease, an extracellular protease, a metalloproteinase, or a mixture thereof.

6. The method of claim 1, wherein the degrading agent comprises a degrading catalyst.

7. The method of claim 1, further comprising monitoring the exposing step (c), monitoring the resultant products produced during step (c), or both by multi-mode detection.

8. The method of claim 1, wherein in step (c), the immobilized protein is exposed to a selected degrading agent having a known concentration.

* * * * *